(12) United States Patent
Moon et al.

(10) Patent No.: US 7,670,774 B2
(45) Date of Patent: Mar. 2, 2010

(54) PROBE OF HUMAN PAPILLOMAVIRUS AND DNA CHIP COMPRISING THE SAME

(75) Inventors: Woo-Chul Moon, Busan (KR); Myung-Ryurl Oh, Suwon-si (KR); Su-Bin Yim, Seoul (KR); Tae-Han Eum, Seoul (KR); Eun-Hae Jung, Chuncheon-si (KR); Jung-Eun Ko, Seongnam-si (KR); Jae-Han Bae, Daegu (KR)

(73) Assignee: Goodgene Inc., Seoul (KR)

( * ) Notice: Subject to any disclaimer, the term of this patent is extended or adjusted under 35 U.S.C. 154(b) by 54 days.

(21) Appl. No.: 11/664,549

(22) PCT Filed: Mar. 18, 2005

(86) PCT No.: PCT/KR2005/000775

§ 371 (c)(1),
(2), (4) Date: Apr. 3, 2007

(87) PCT Pub. No.: WO2006/038753

PCT Pub. Date: Apr. 13, 2006

(65) Prior Publication Data

US 2007/0248968 A1    Oct. 25, 2007

(30) Foreign Application Priority Data

Oct. 4, 2004  (KR) ............. 10-2004-0078685

(51) Int. Cl.
*C12Q 1/64* (2006.01)
*C12M 1/00* (2006.01)

(52) U.S. Cl. ............... 435/6; 435/283.1; 435/975

(58) Field of Classification Search ............ None
See application file for complete search history.

(56) References Cited

U.S. PATENT DOCUMENTS 6,482,588 B1 * 11/2002 Van Doorn et al. ............ 435/5
6,582,908 B2 * 6/2003 Fodor et al. ............. 506/9

FOREIGN PATENT DOCUMENTS

| EP | 0774518 A2 | 5/1997 |
|---|---|---|
| KR | 10-2003-0027178 A | 4/2003 |
| KR | 10-2003-0041212 A | 5/2003 |
| KR | 10-2006-0029836 A | 4/2006 |
| WO | WO 9522626 A1 * | 8/1995 |
| WO | 01/68915 A1 | 9/2001 |

OTHER PUBLICATIONS

New England Biolabs 1998/99 Catalog.*
Korean Patent Abstracts English translation of abstract for Korean Patent Publication No. 10-2006-0029836, published Jul. 7, 2006 (2 pages).
Korean Patent Abstracts English abstract for Korean Patent Publication No. 10-2003-0027178, published Jul. 7, 2003 (2 pages).
Korean Patent Abstracts English abstract for Korean Patent Publication No. 10-2003-0041212, published May 27, 2003 (2 pages).
Notice of Grounds for Rejection issued by the Korean Intellectual Property Office on Mar. 10, 2006 in related Korean Patent Application No. 10-2004-0078685, with English translation (5 pages).
Notice of Grounds for Rejection issued by the Korean Intellectual Property Office on May 29, 2006, in related Korean Patent Application No. 10-2004-0078685, with English translation (6 pages).
Notice of Grounds for Rejection issued by the Korean Intellectual Property Office on Aug. 10, 2006, in related Korean Patent Application No. 10-2204-0078685, with English translation (3 pages).
Decision for Patent Grant issued Aug. 29, 2006, by the Korean Intellectual Property Office in related Korean Patent Application No. 10-2004-0078685, with English translation (3 pages).
International Search Report issued Jul. 12, 2005, by the Korean Intellectual Property Office, in related Korean Patent Application No. PCT/KR2005/000775 (3 pages) (Note: A copy of this Search Report was filed with the USPTO with the original Application filed on Apr. 3, 2007.).

* cited by examiner

*Primary Examiner*—Christopher M. Babic
(74) *Attorney, Agent, or Firm*—Osha • Liang LLP

(57) ABSTRACT

Oligonucleotide probes for analyzing 40 types of HPV were synthesized, and DNA chips were produced by using the oligonucleotide probes. The synthesis of the oligonucleotide probes is based on clones of L1 and E6/E7 genes of 35 types of HPV obtained from cervical cell specimens from 4,898 Korean adult women and tissue specimens from 68 cervical cancer cases in addition to information based on American and European cases. The DNA chips can analyze the 40 types of HPV found in cervical, diagnose complex infection by at least one type of HPV, and have excellent diagnostic sensitivity and specificity on HPV genetic type up to 100% and reproducibility. Also, the DAN chips are superior to conventional analytic method, and very economical, since they can analyze numerous specimens in shortest time. Accordingly, the DNA chips are useful for predicting cervical cancer and precancerous lesion.

15 Claims, 27 Drawing Sheets

[Fig. 1]
[Fig. 2]
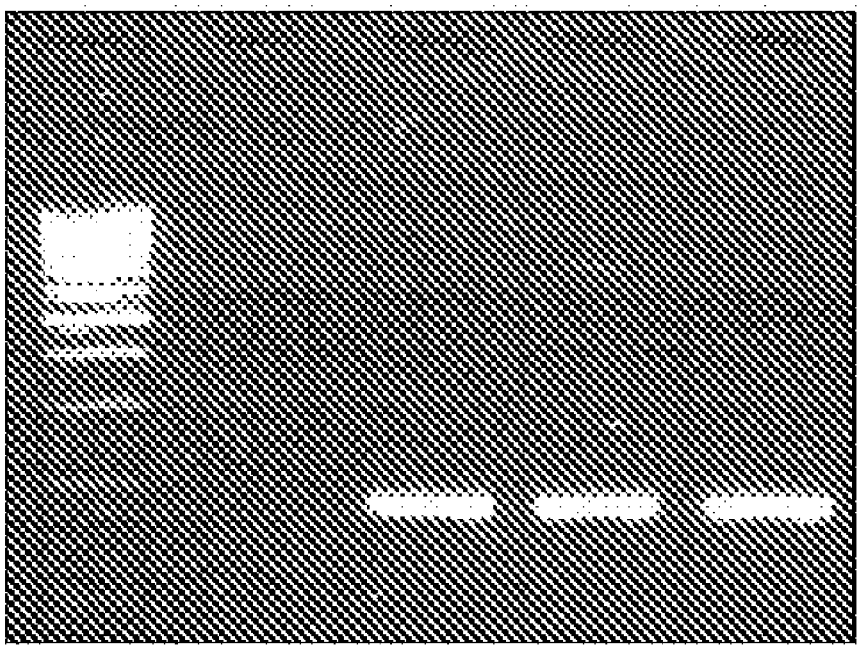

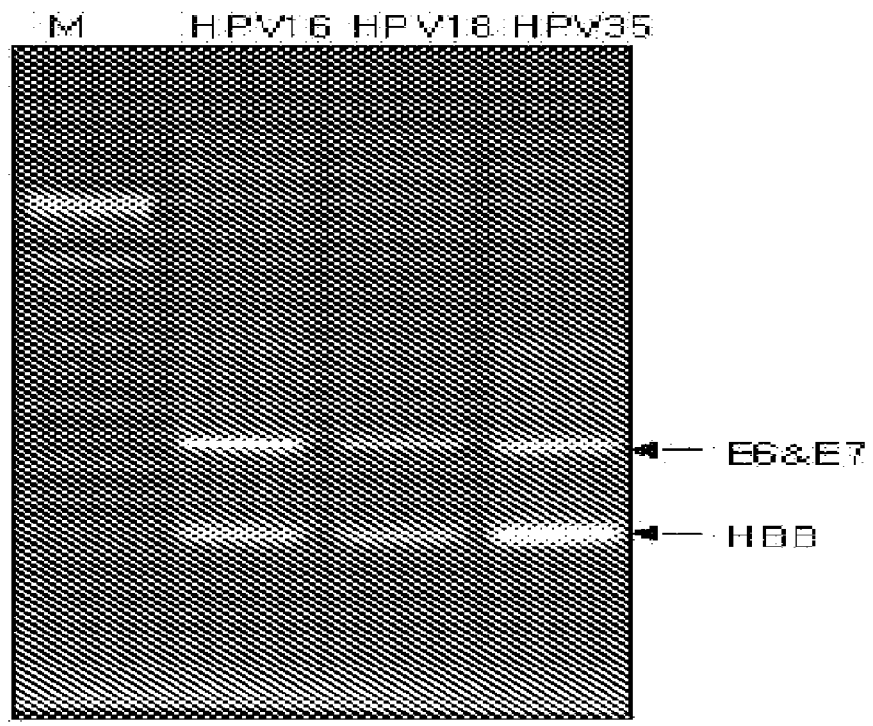
[Fig. 3]
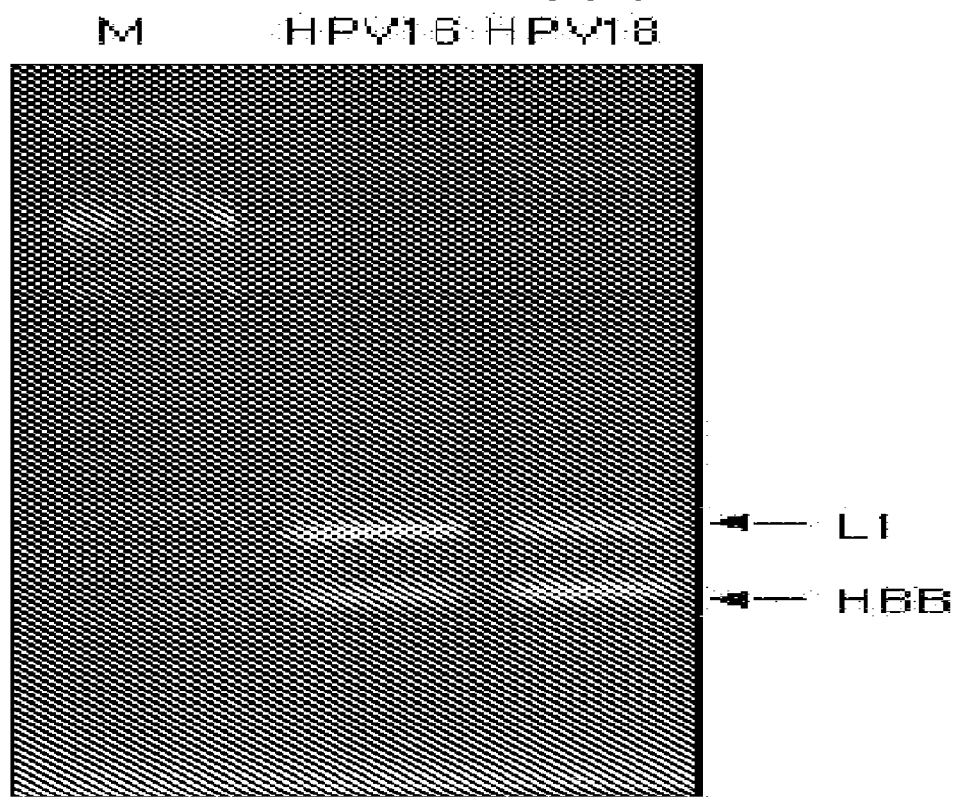
[Fig. 4]

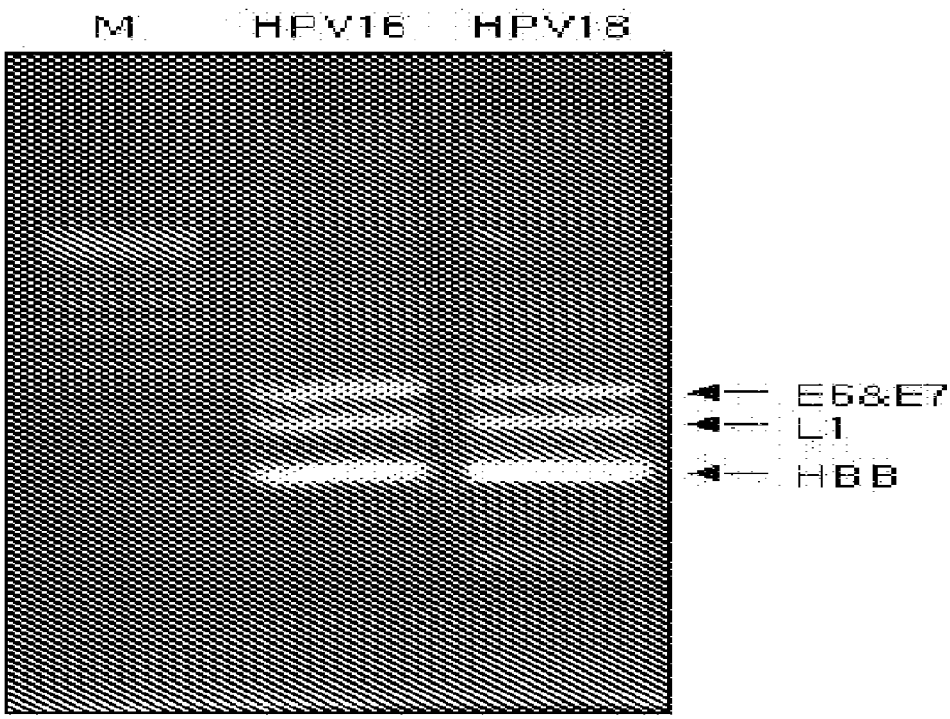
[Fig. 5]
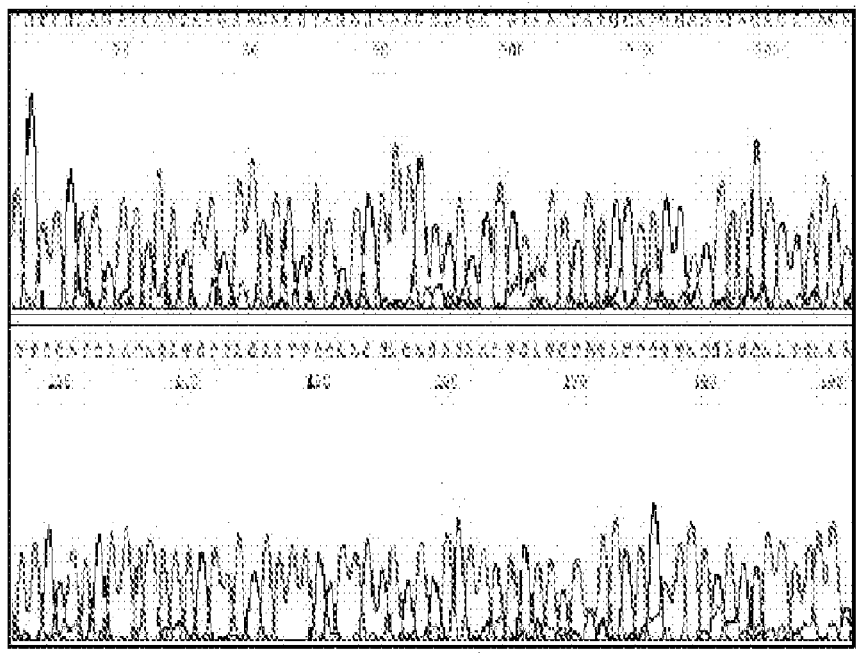
[Fig. 6]

[Fig. 7]
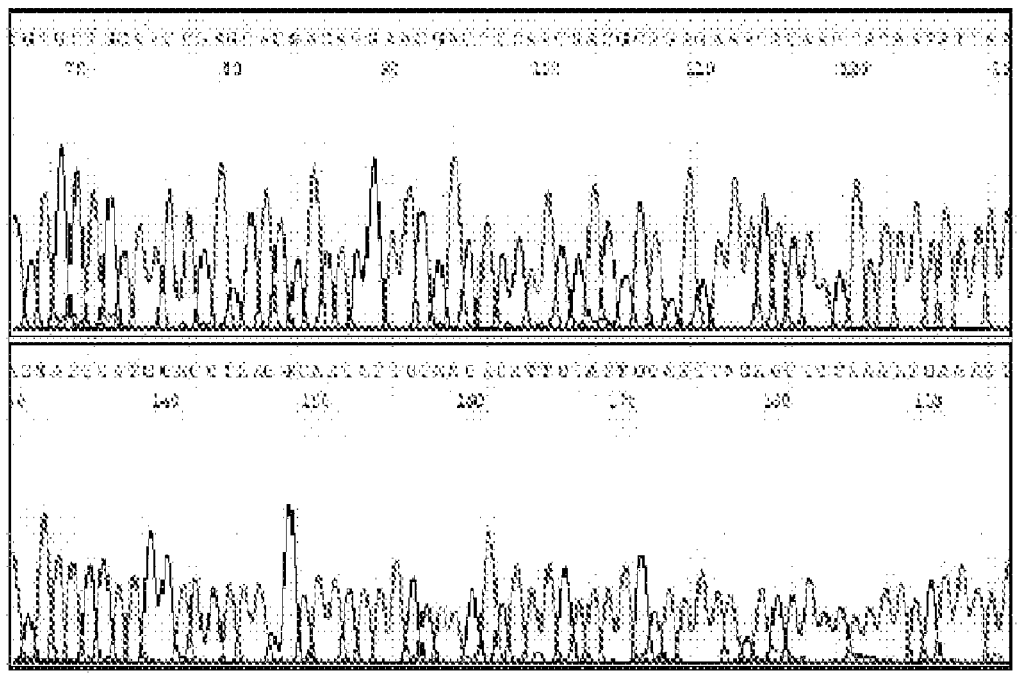
[Fig. 8]
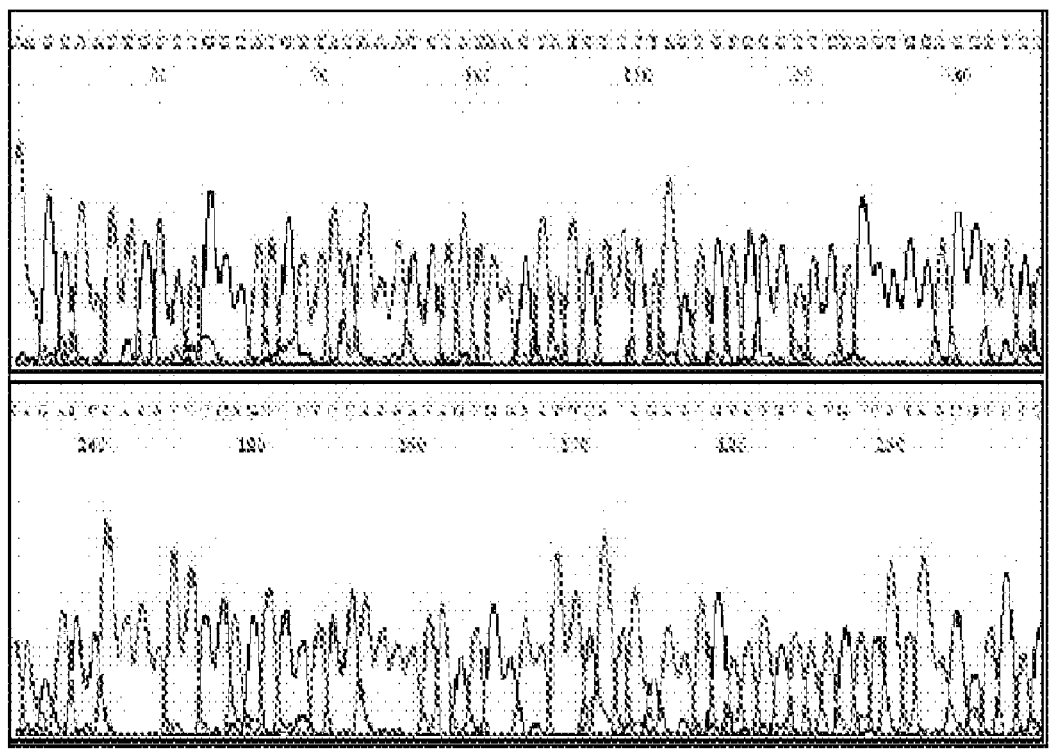

[Fig. 9]
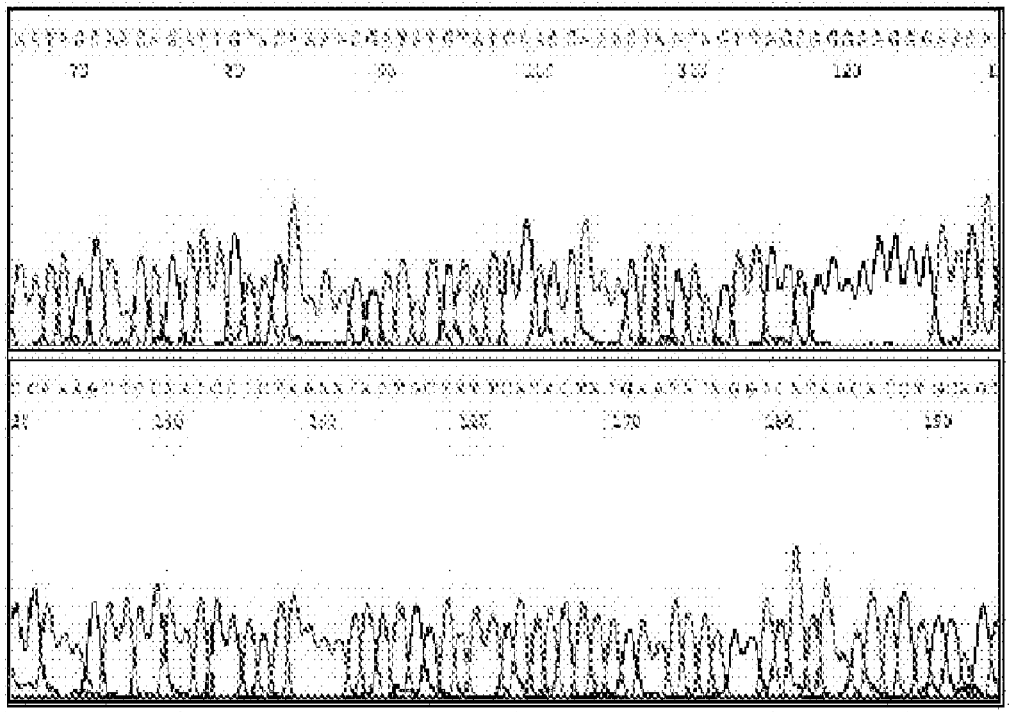
[Fig. 10]
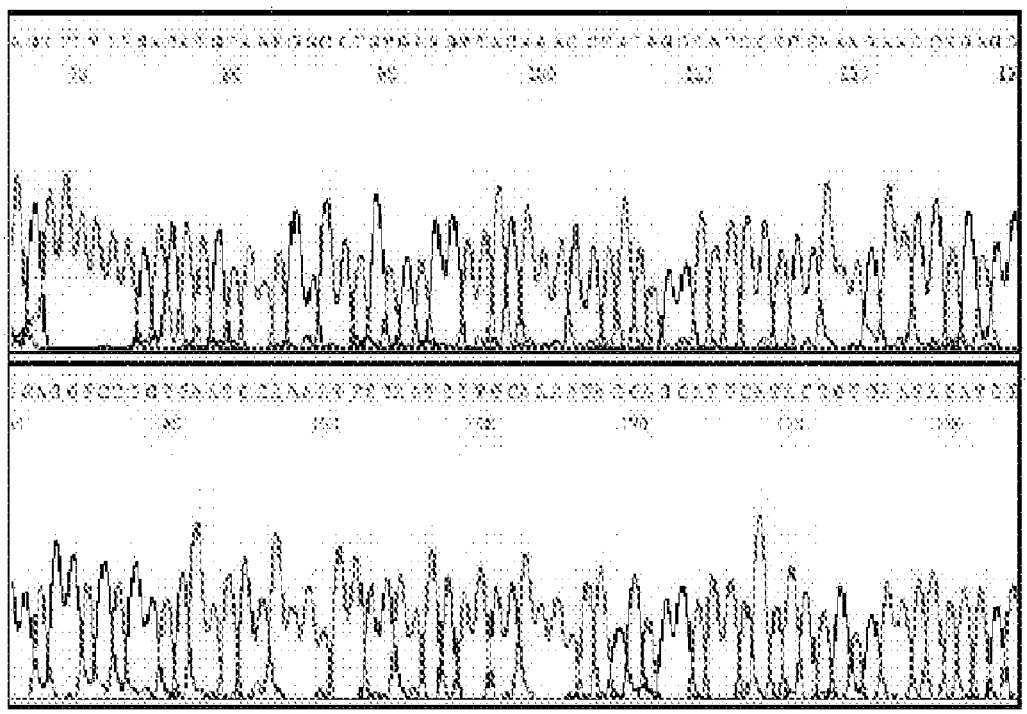

[Fig. 11]
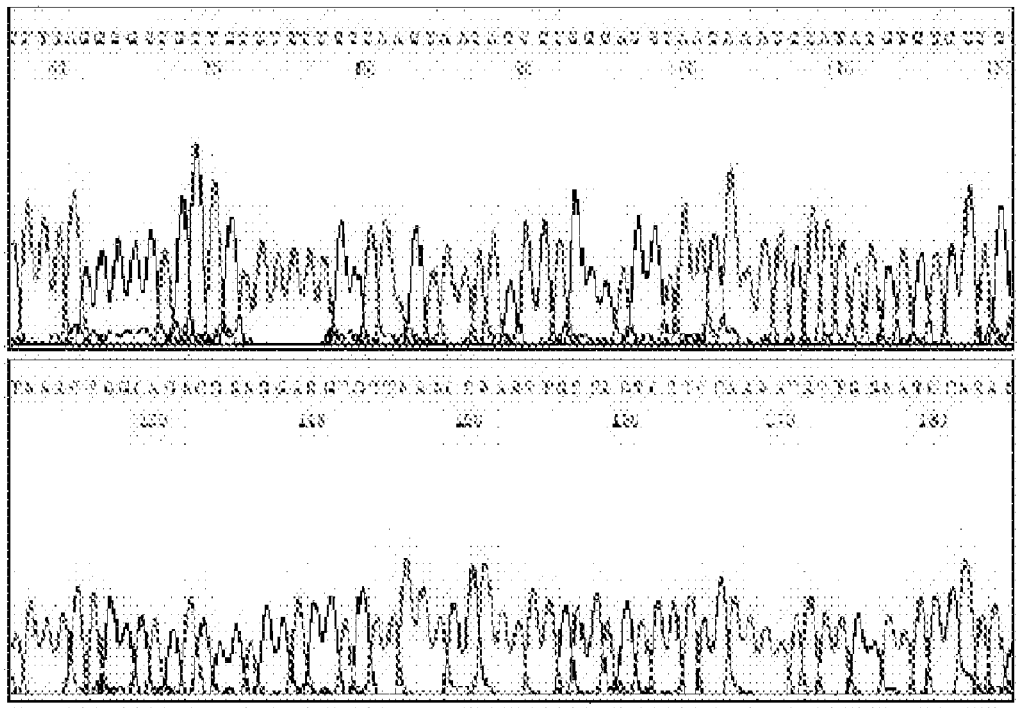
[Fig. 12]
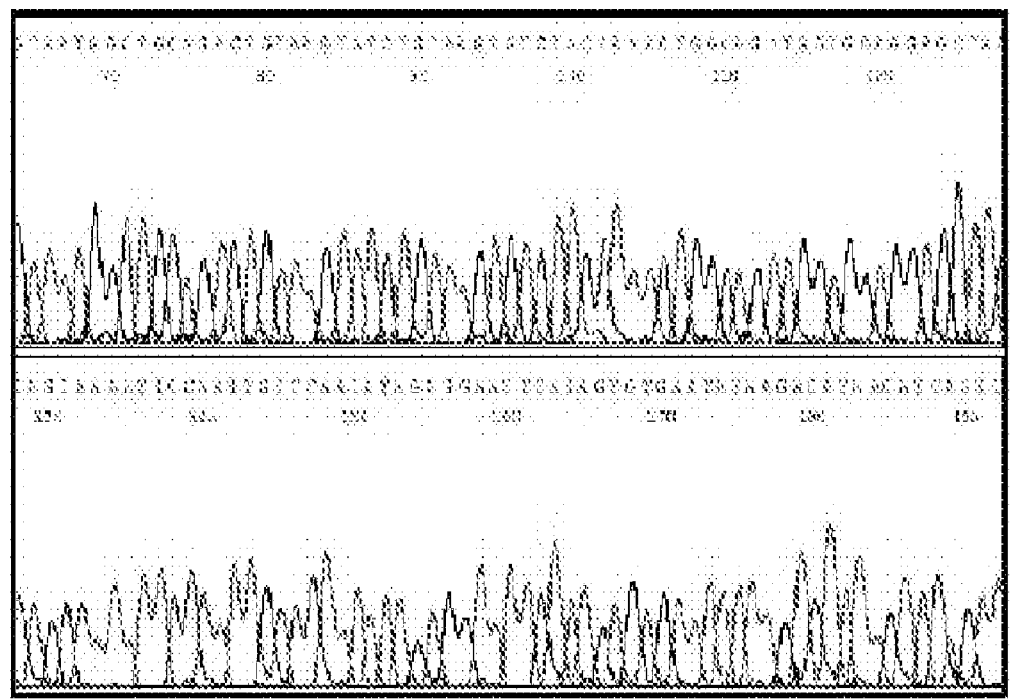

[Fig. 13]
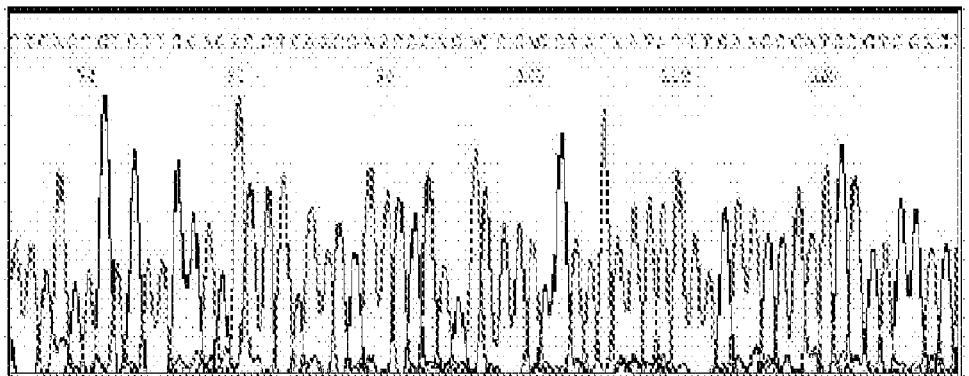
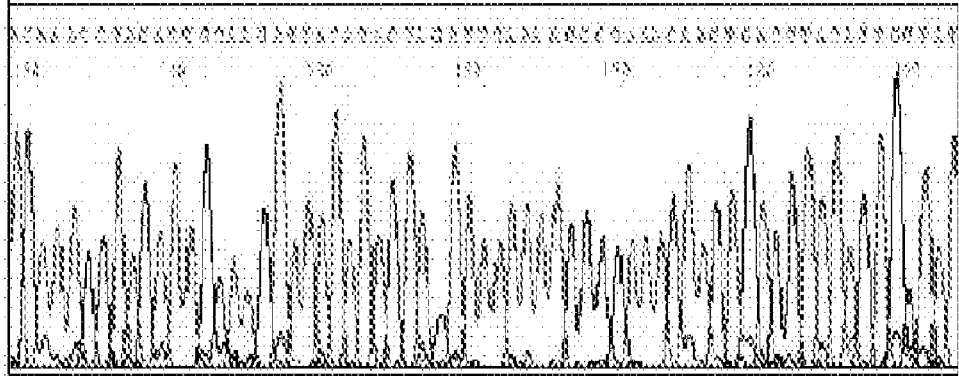
[Fig. 14]
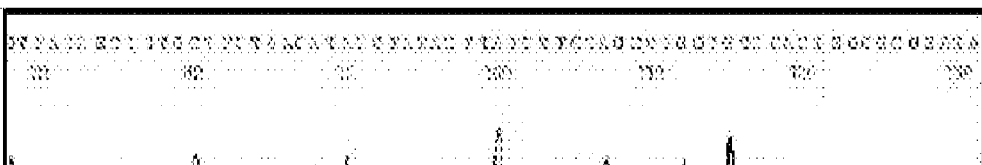
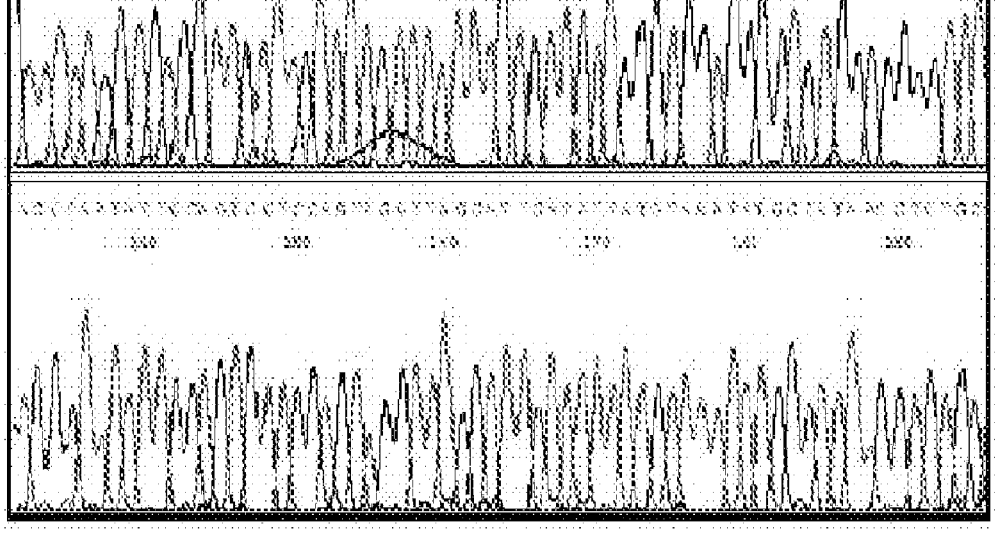

[Fig. 15]
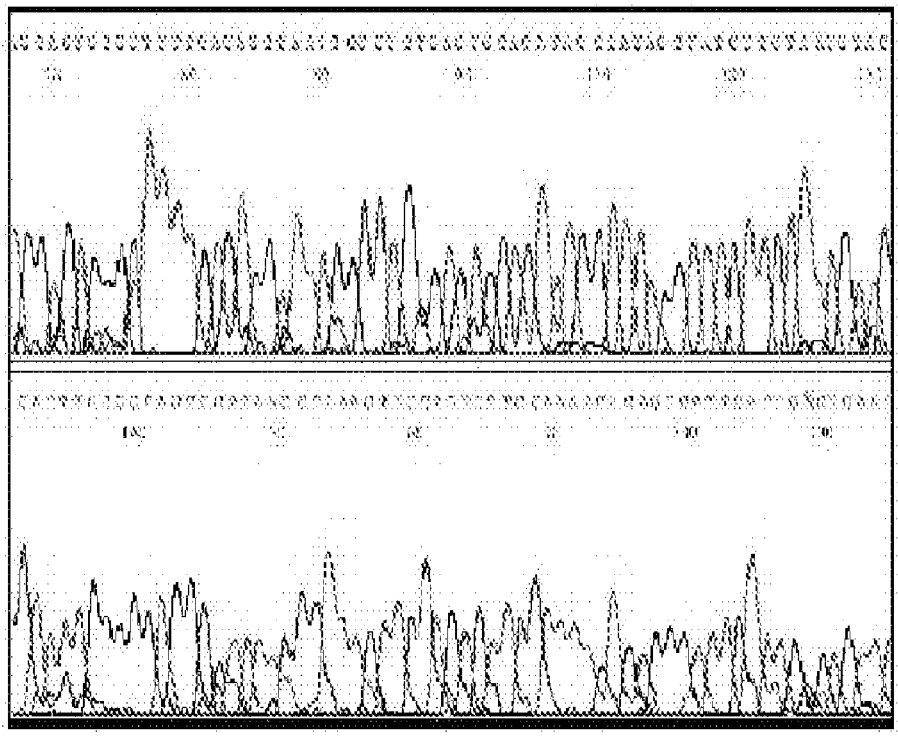
[Fig. 16]
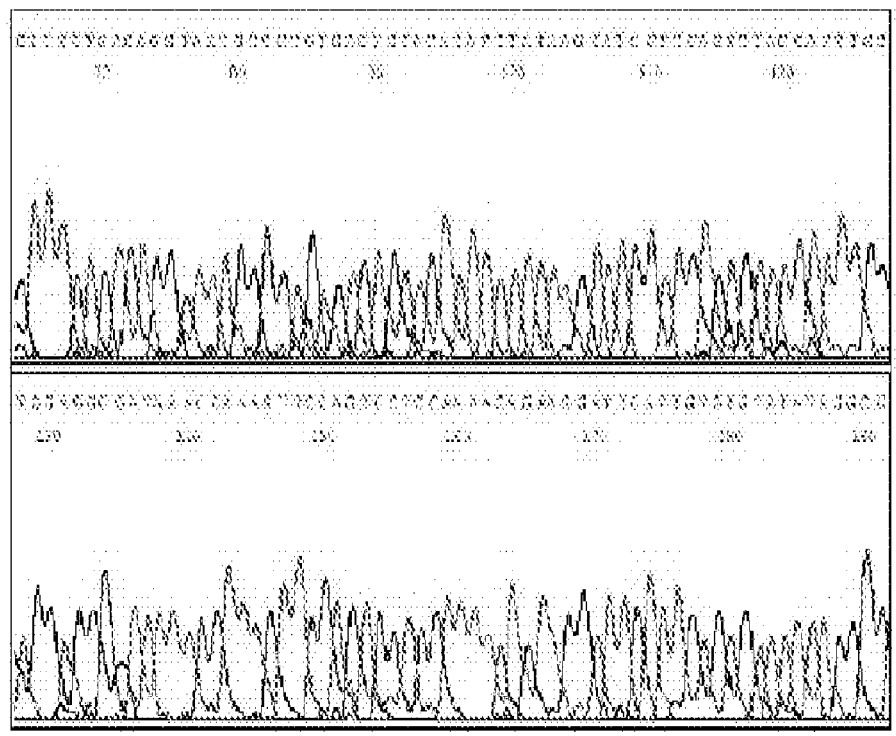

[Fig. 17]
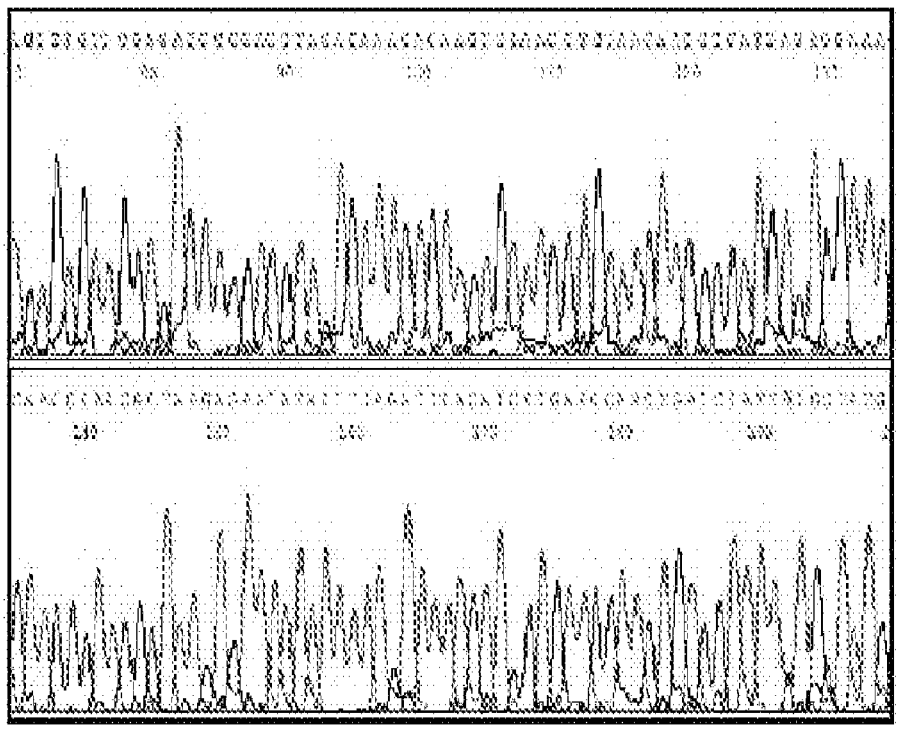
[Fig. 18]
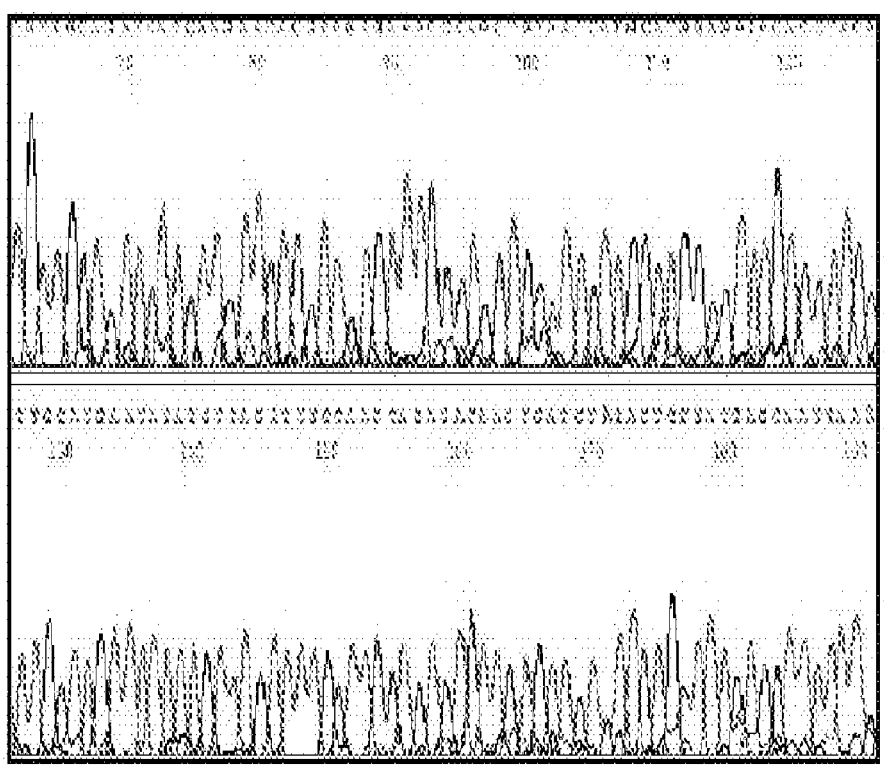

[Fig. 19]
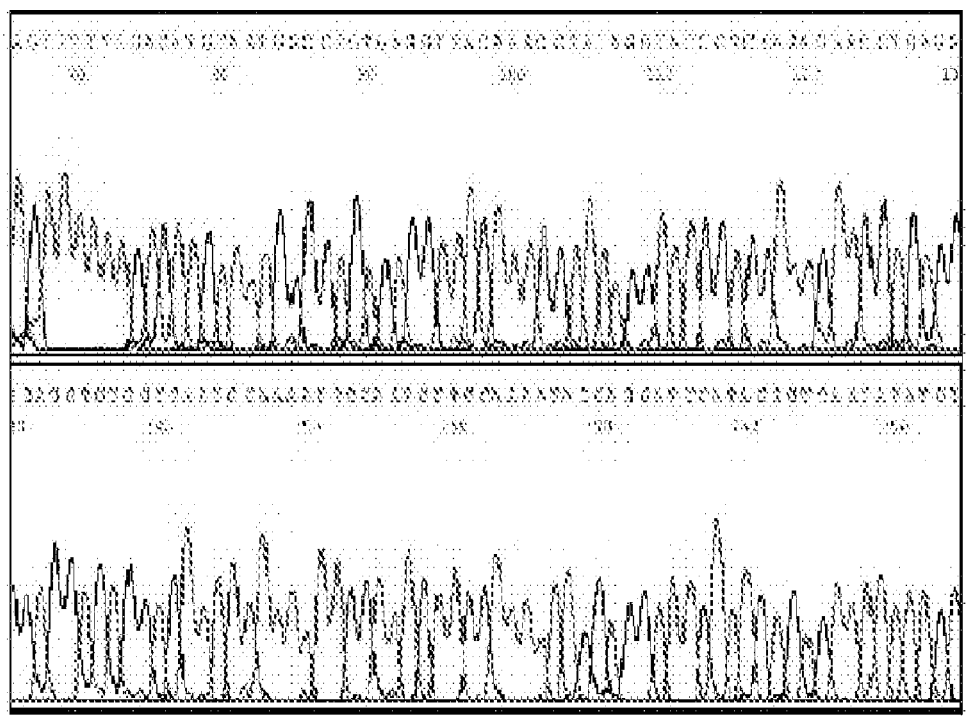
[Fig. 20]
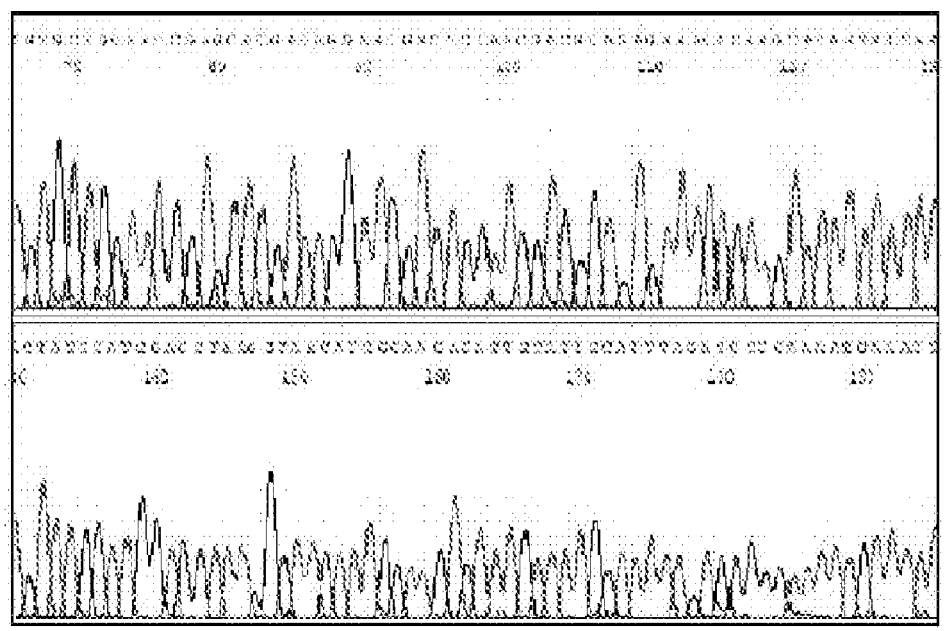

[Fig. 21]
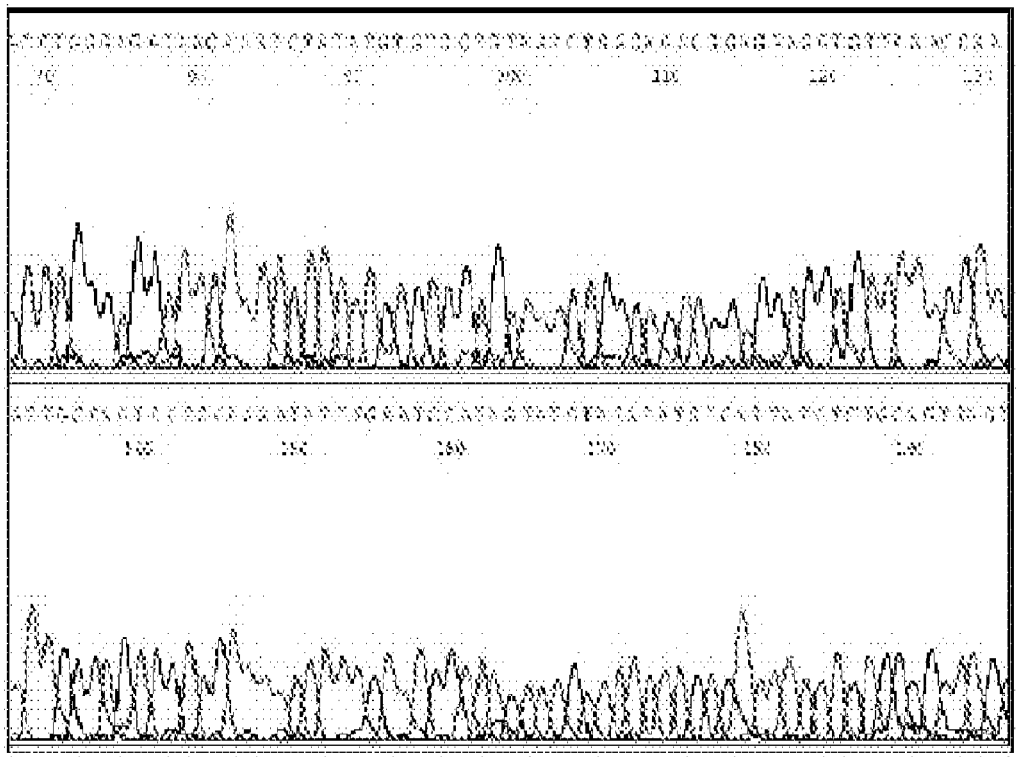
[Fig. 22]
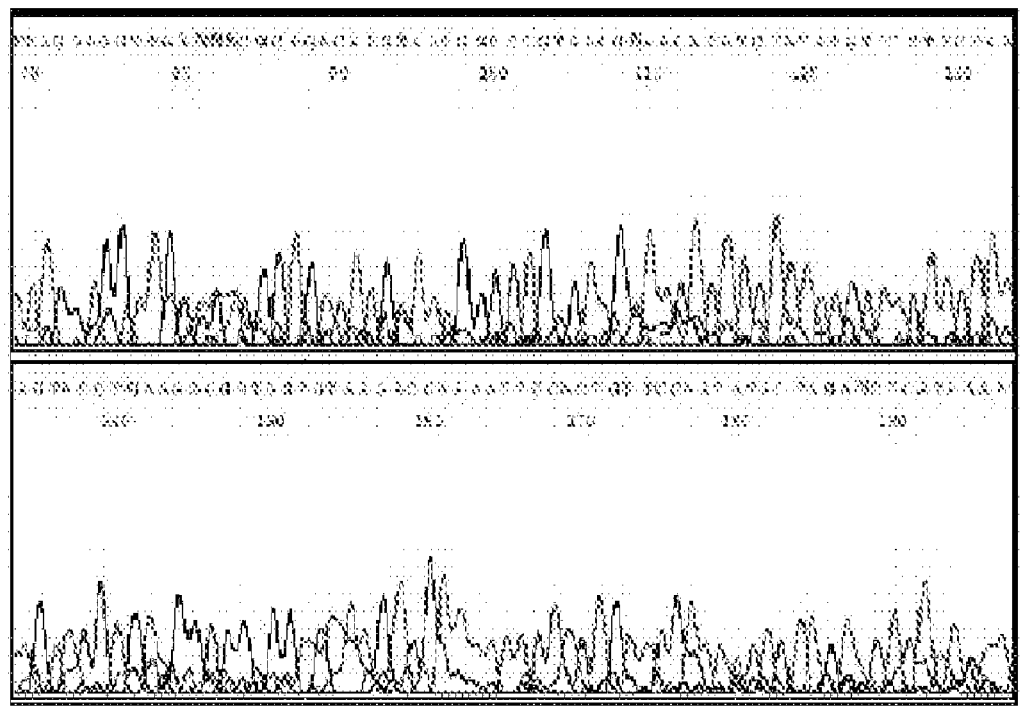

[Fig. 23]
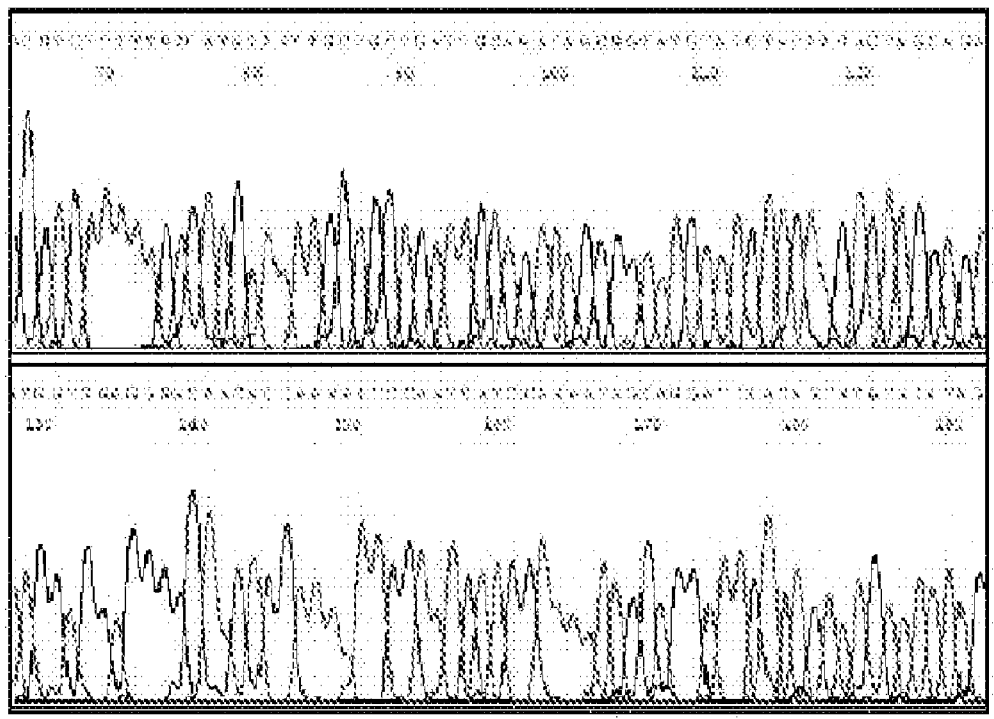
[Fig. 24]
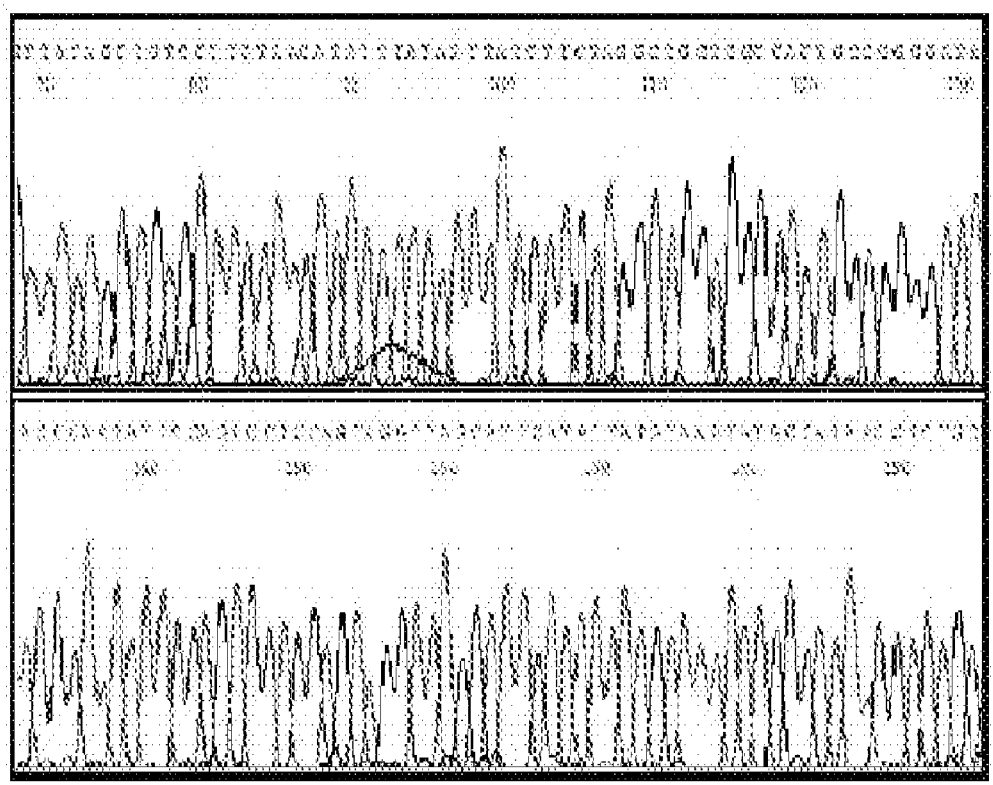

[Fig. 25]
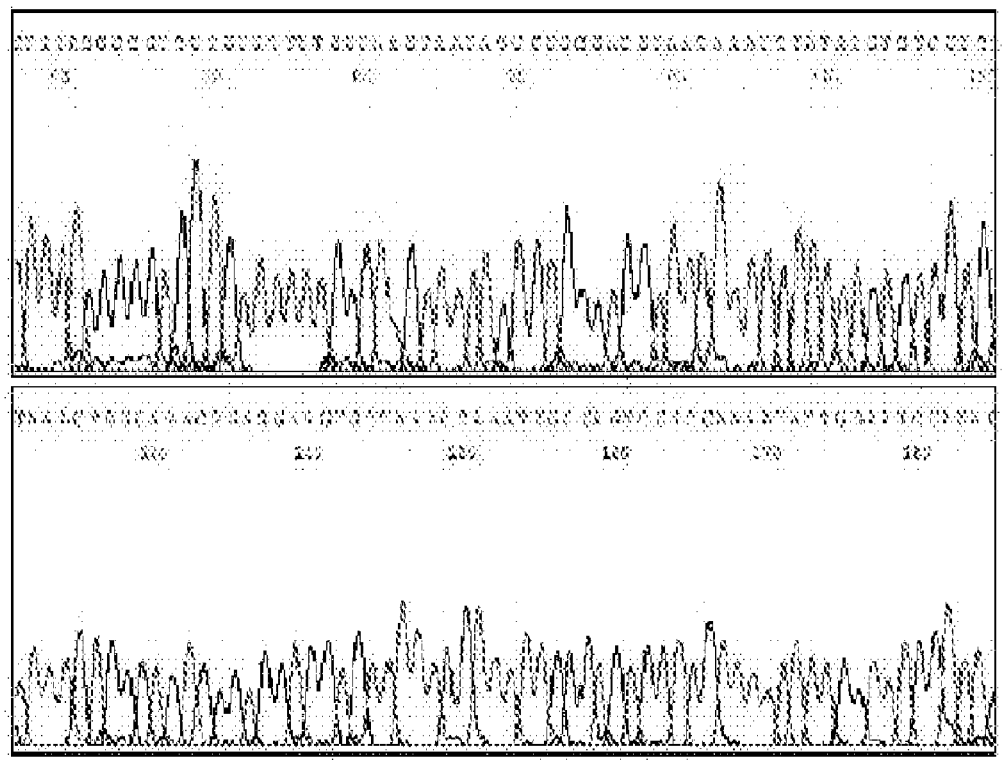
[Fig. 26]
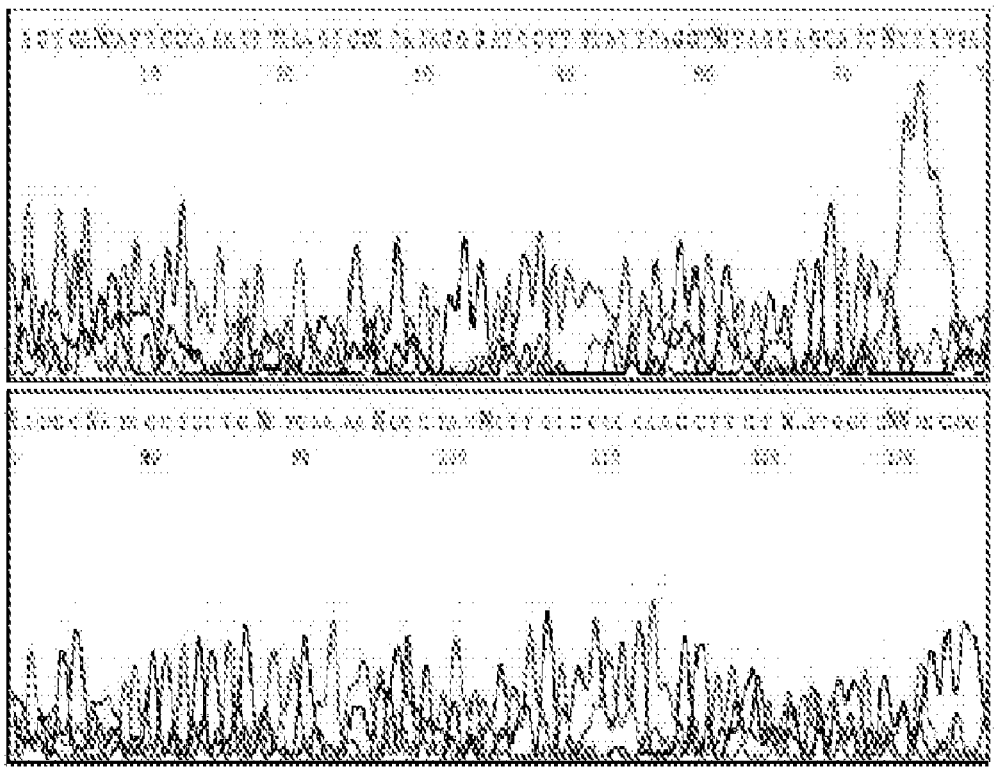

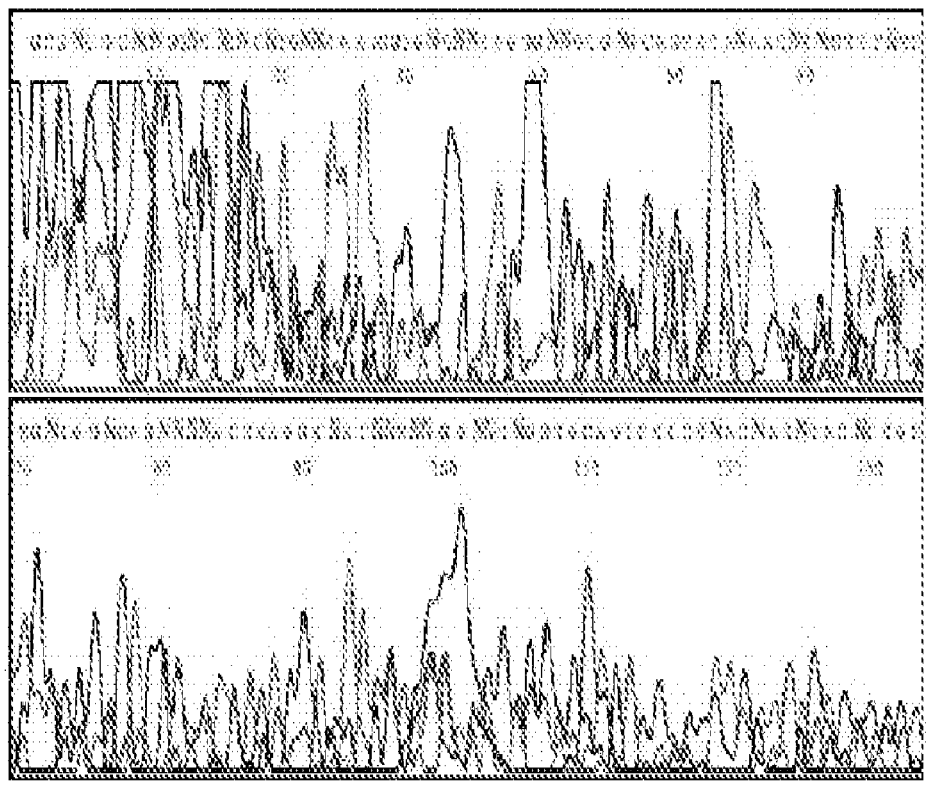
[Fig. 27]
[Fig. 28]

[Fig. 29]
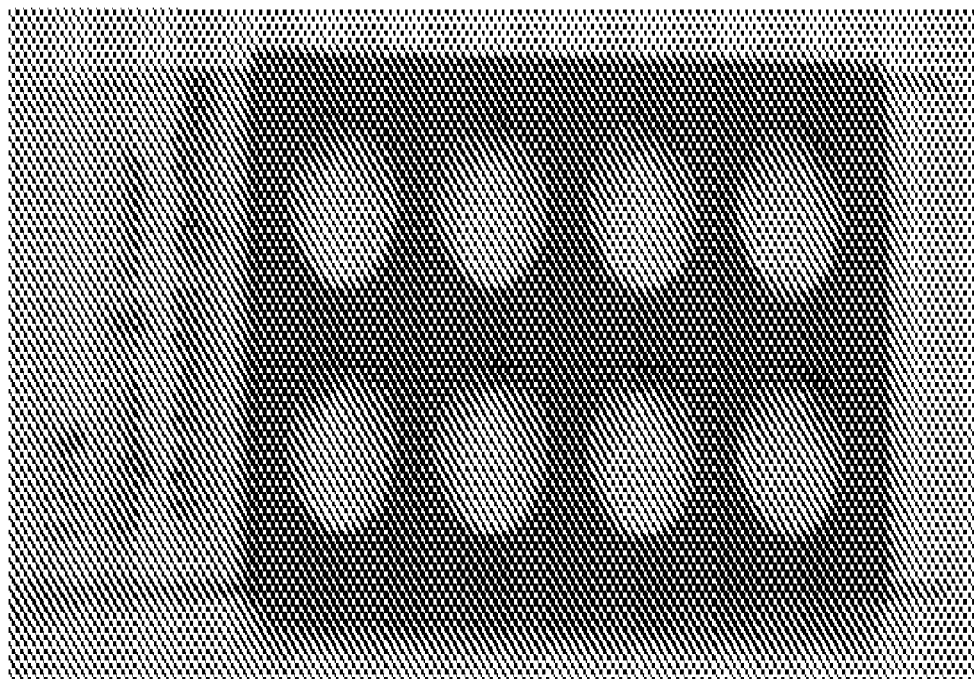
[Fig. 30]
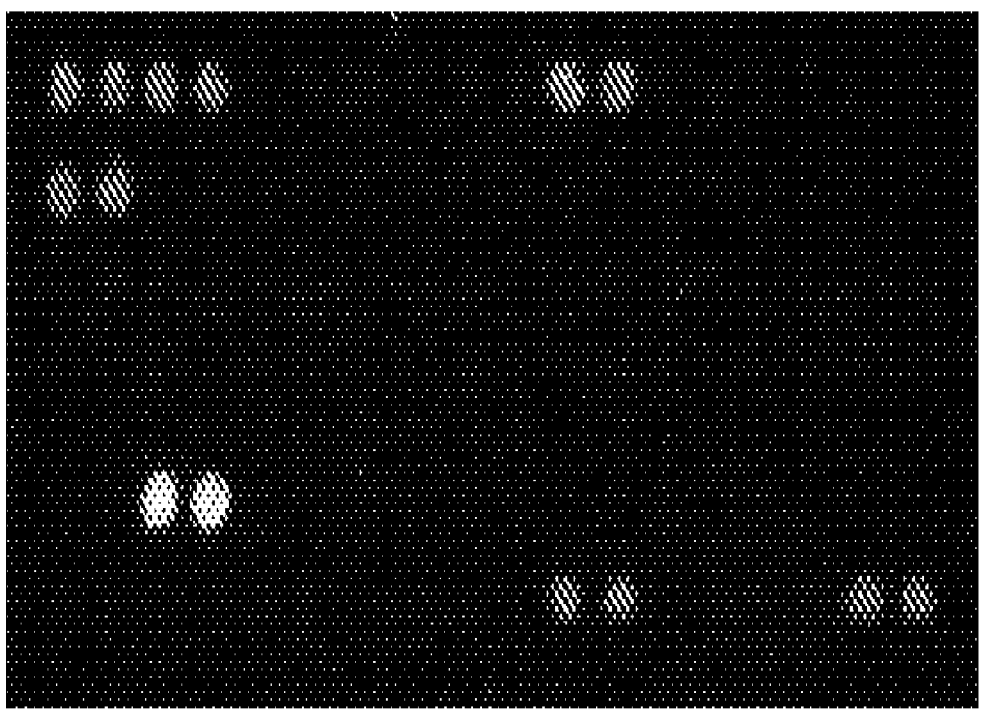

[Fig. 31]
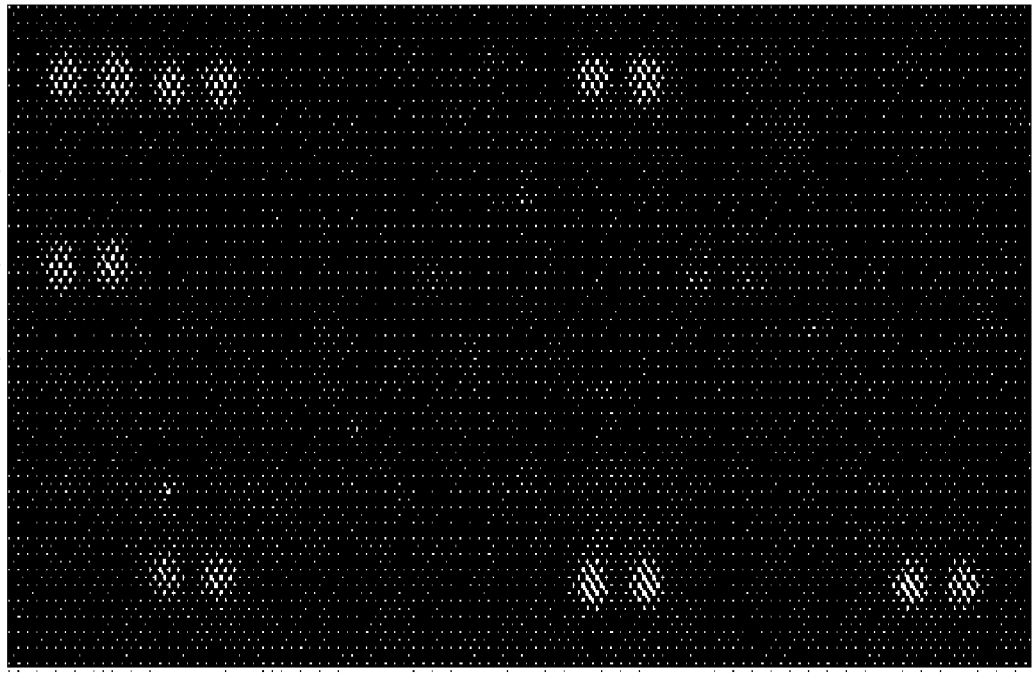
[Fig. 32]
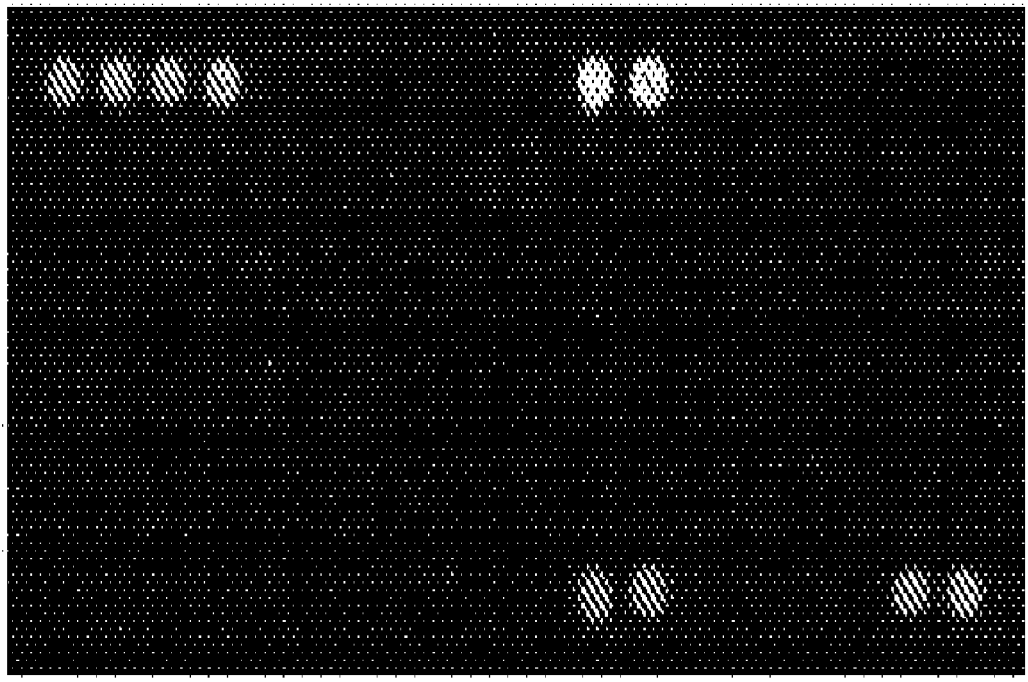

[Fig. 33]
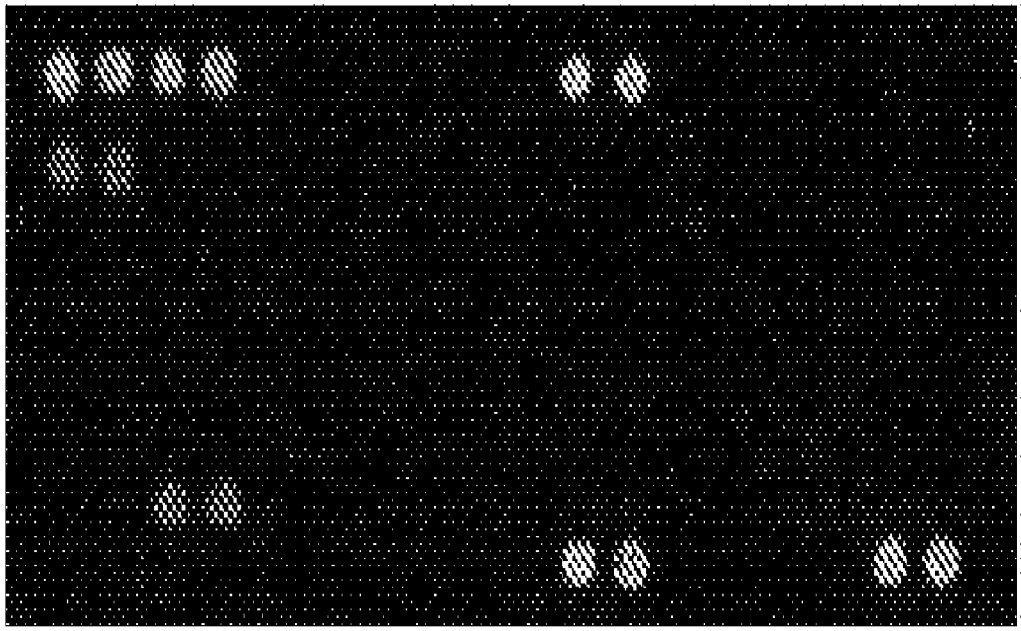
[Fig. 34]
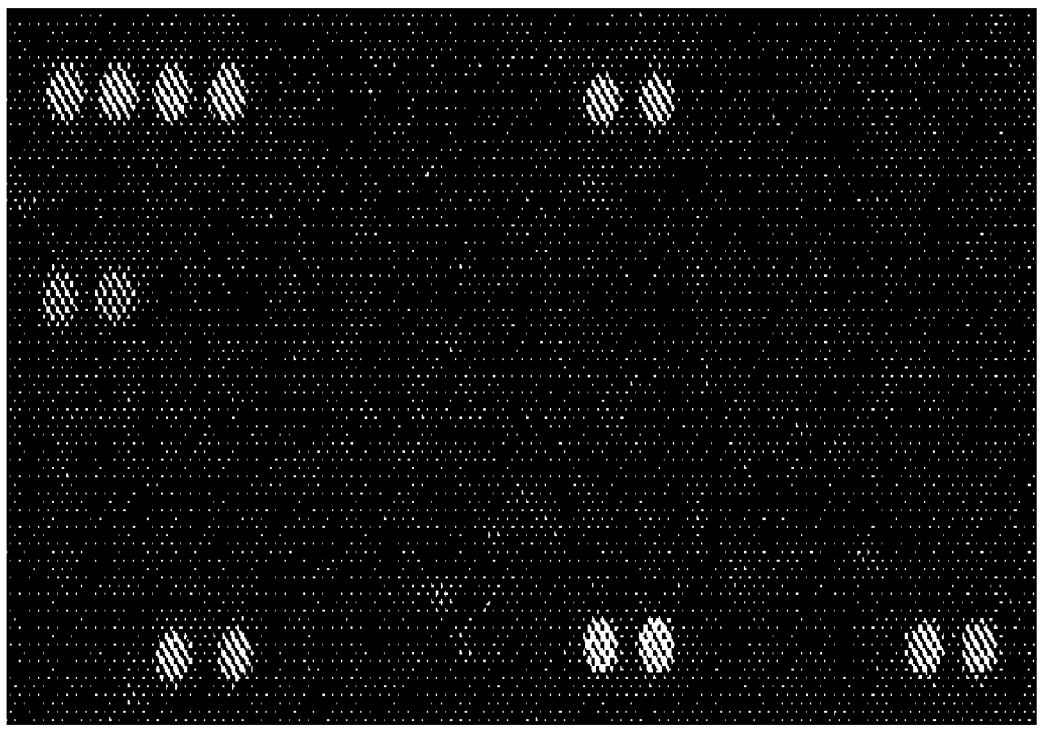

[Fig. 35]
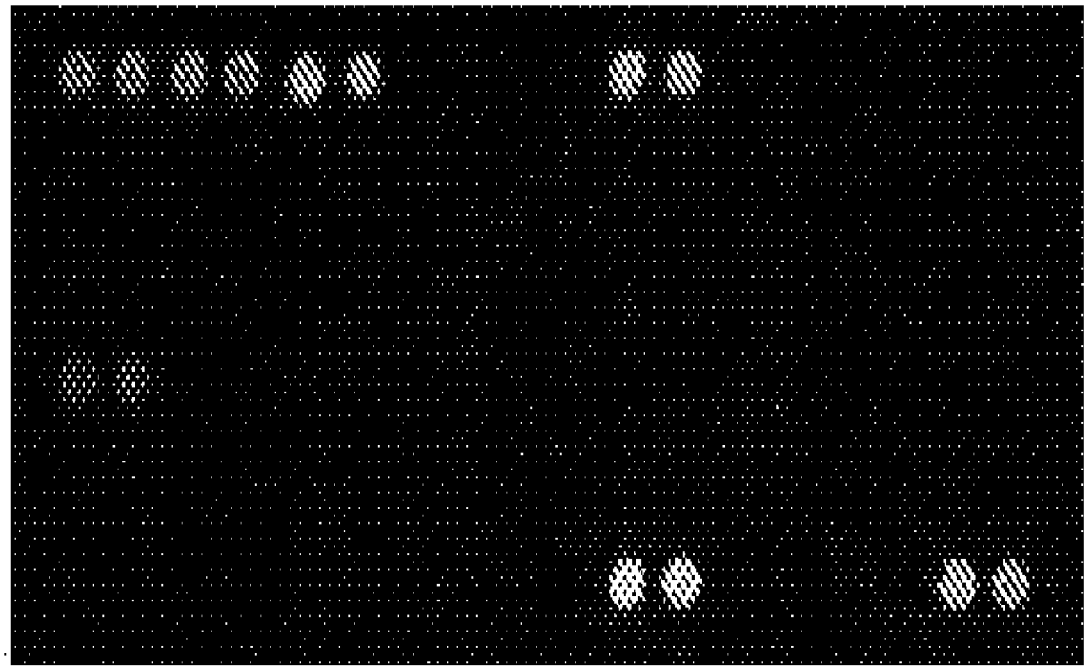
[Fig. 36]
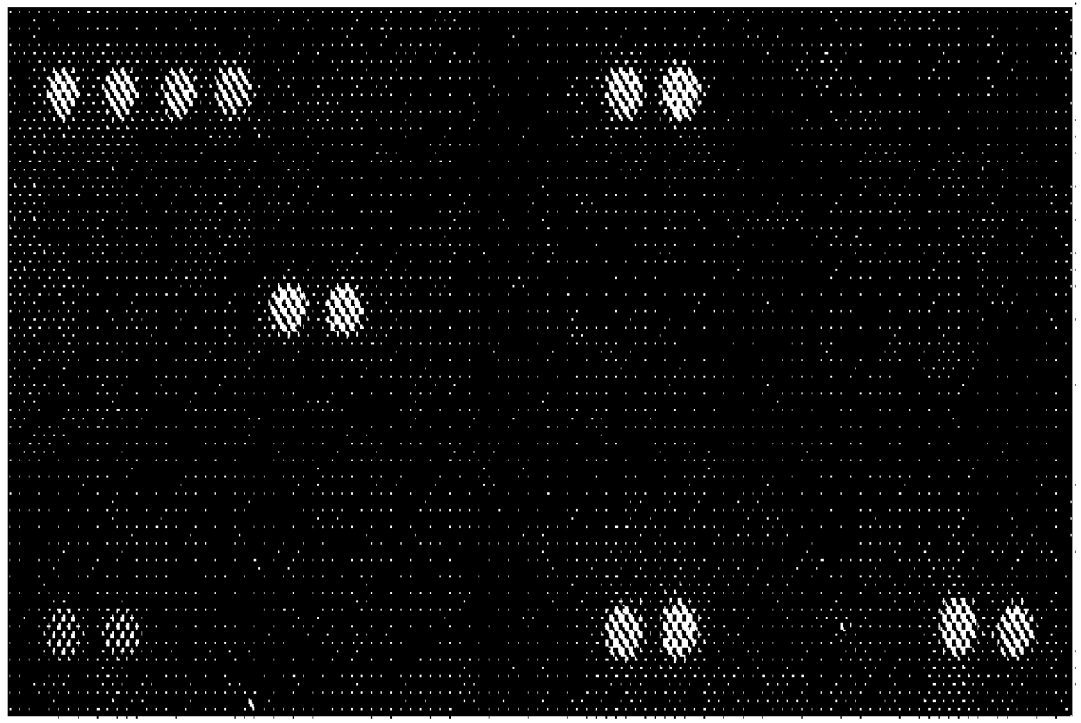

[Fig. 37]
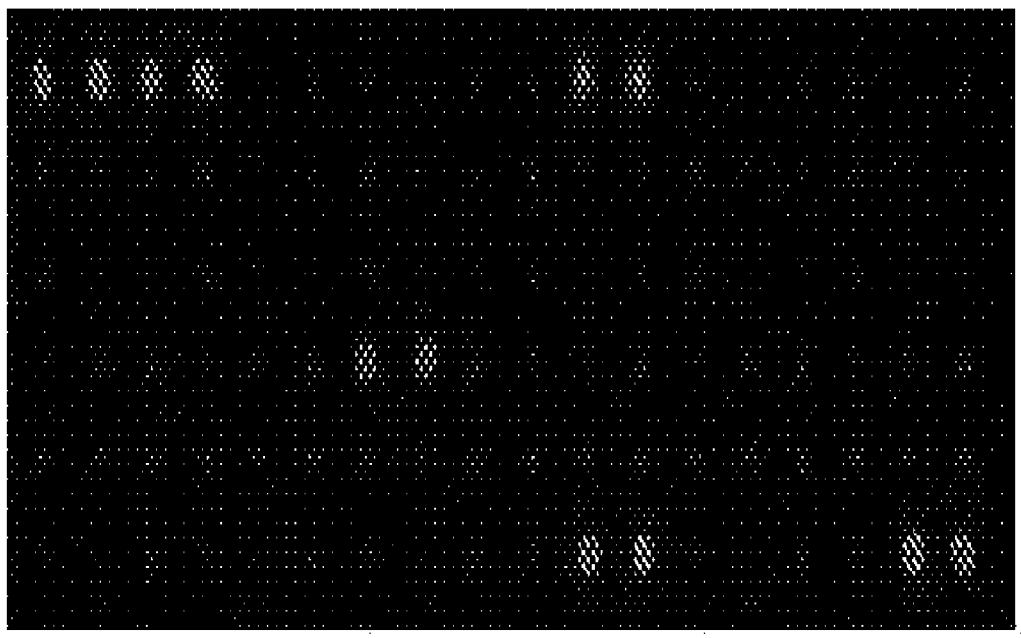
[Fig. 38]
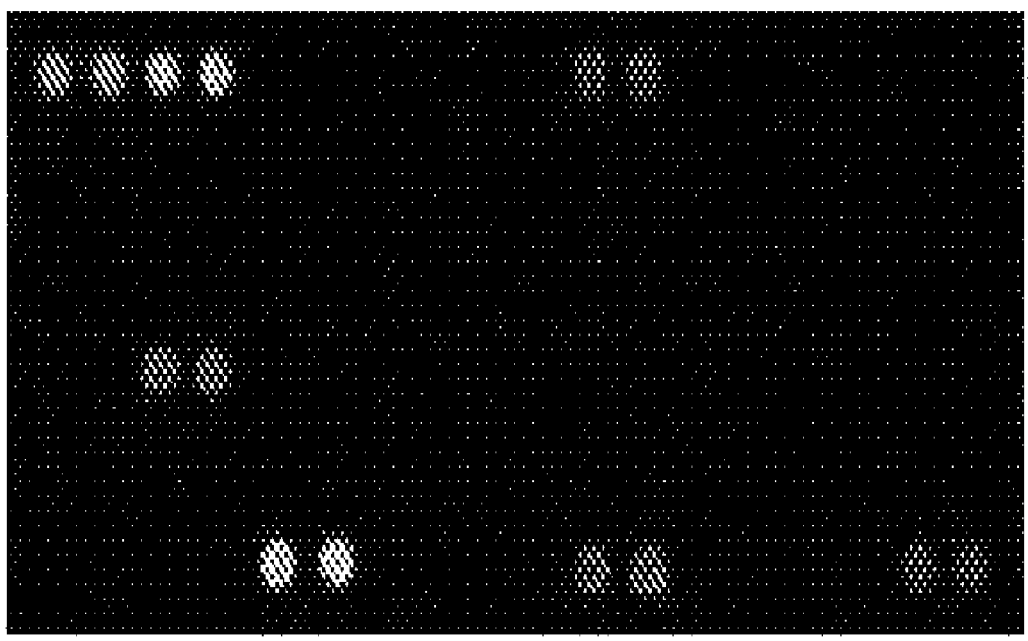

[Fig. 39]
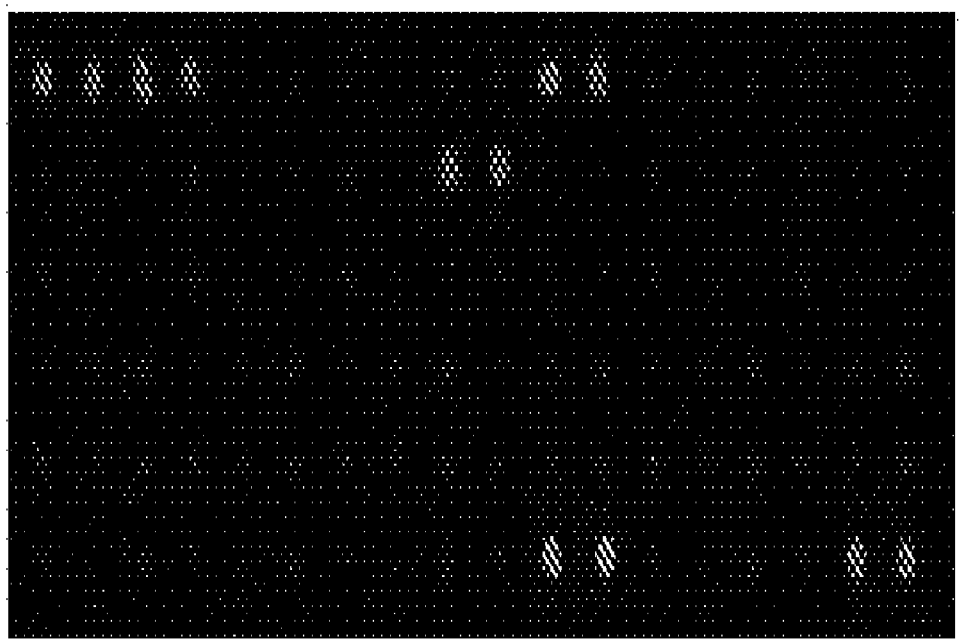
[Fig. 40]
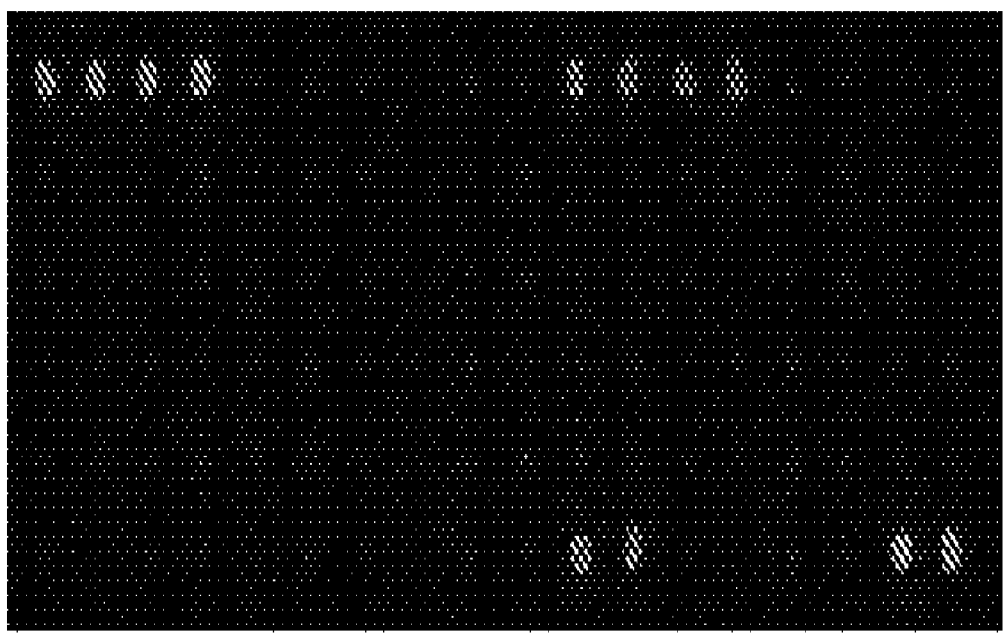

[Fig. 41]
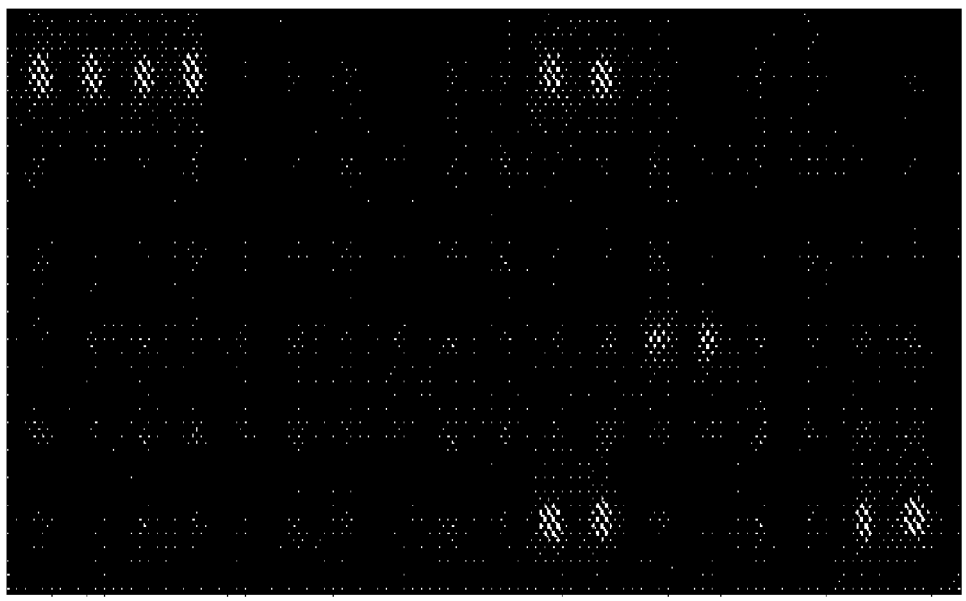
[Fig. 42]
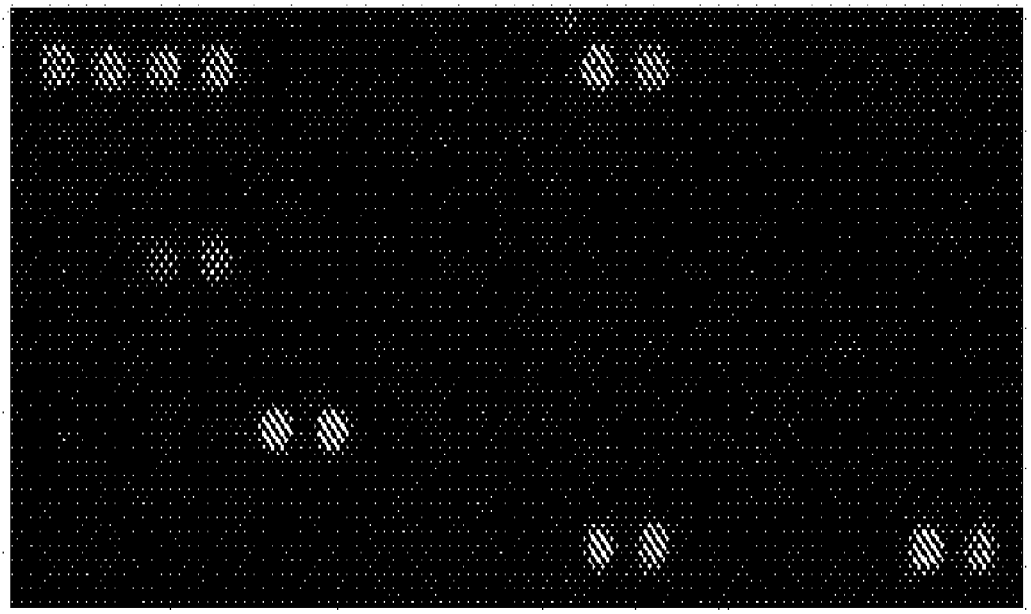

[Fig. 43]
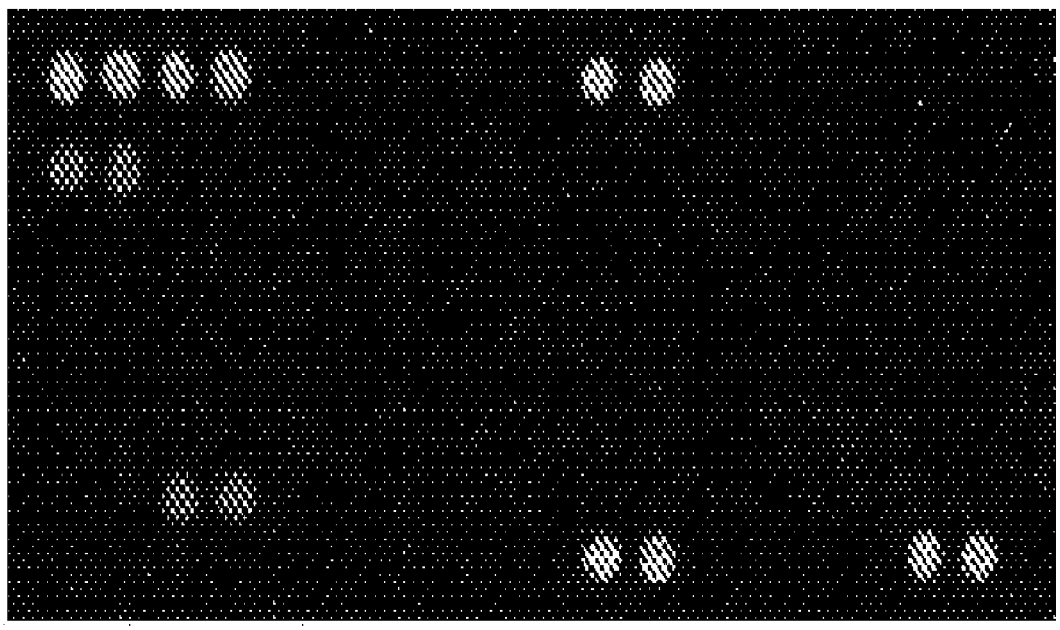
[Fig. 44]
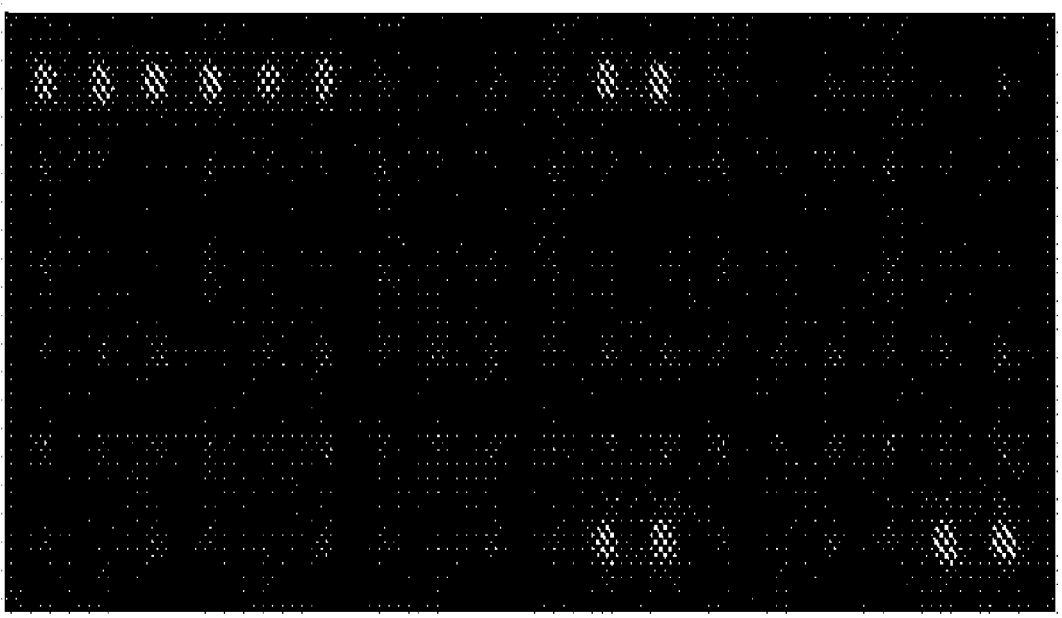

[Fig. 45]
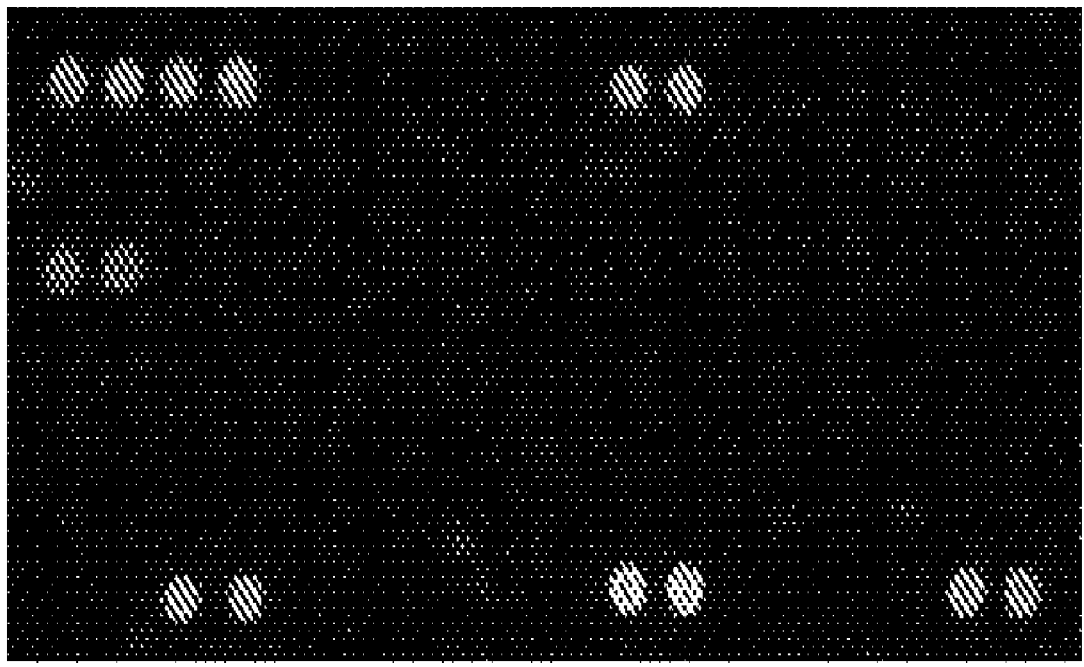
[Fig. 46]
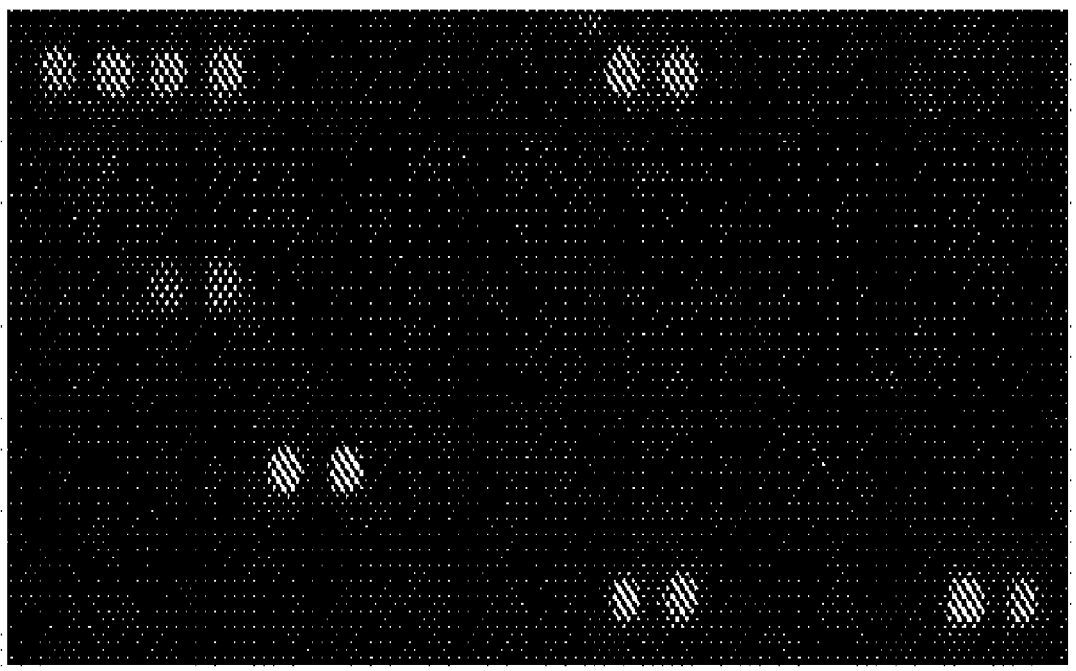

[Fig. 47]
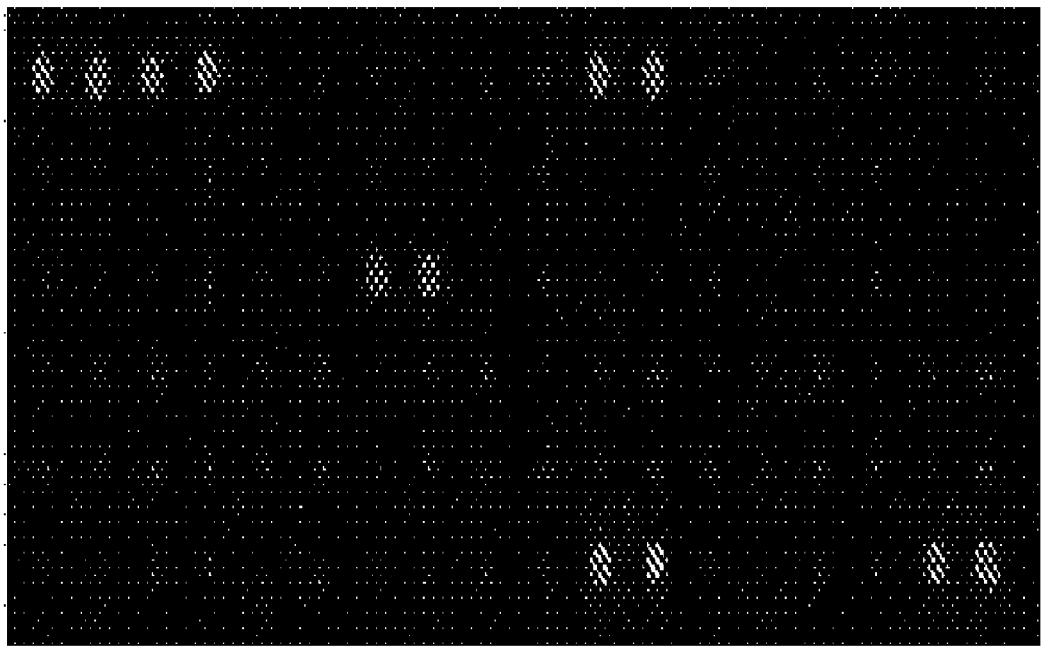
[Fig. 48]
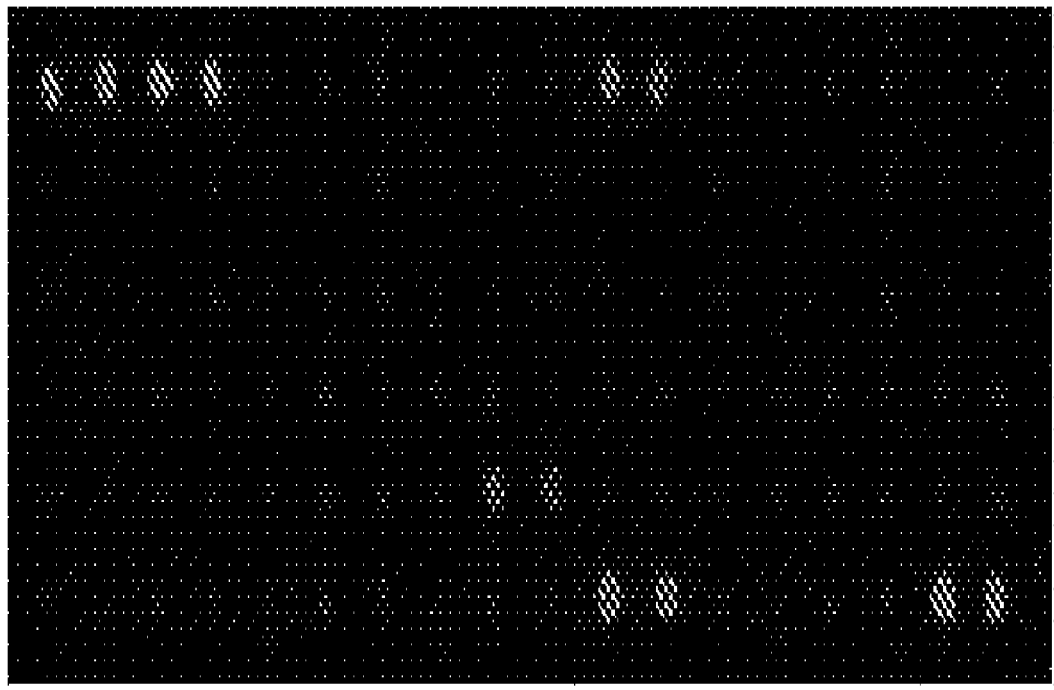

[Fig. 49]
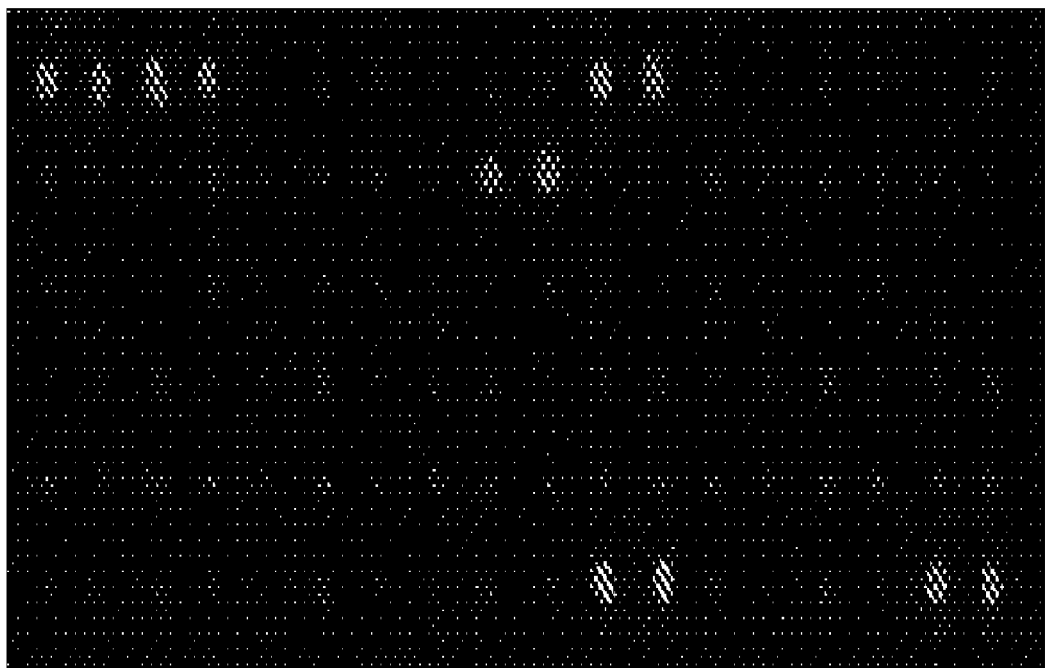
[Fig. 50]
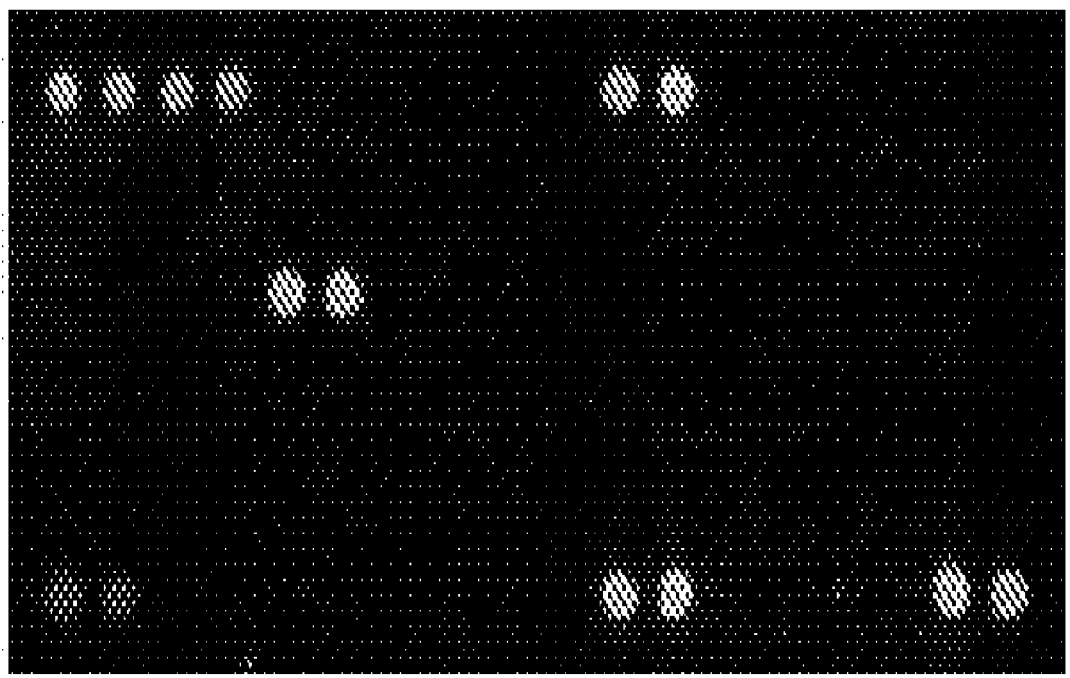

[Fig. 51]
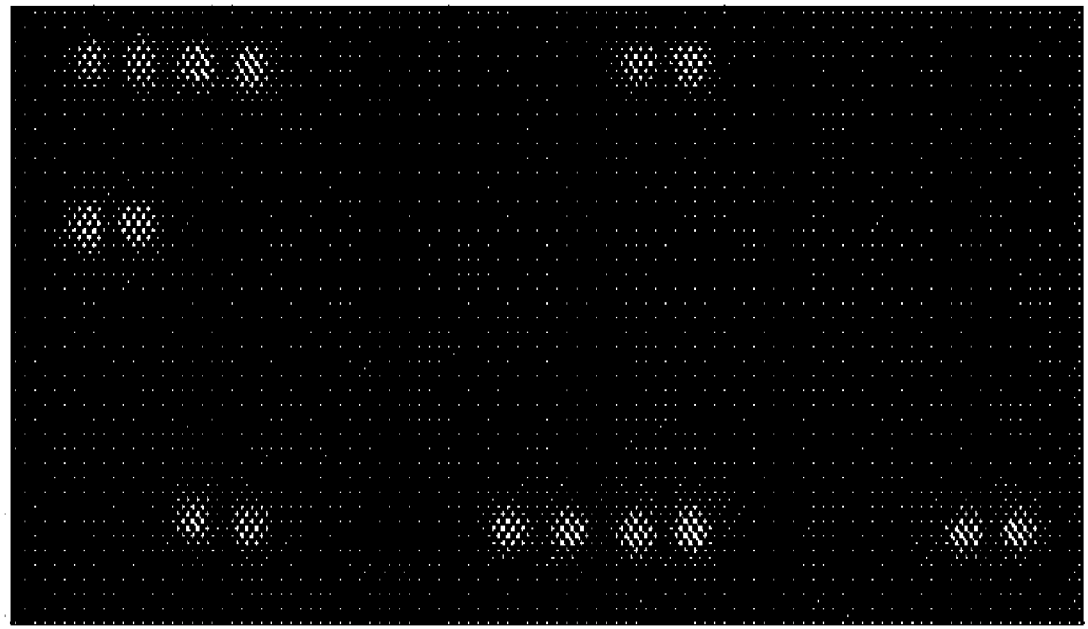
[Fig. 52]
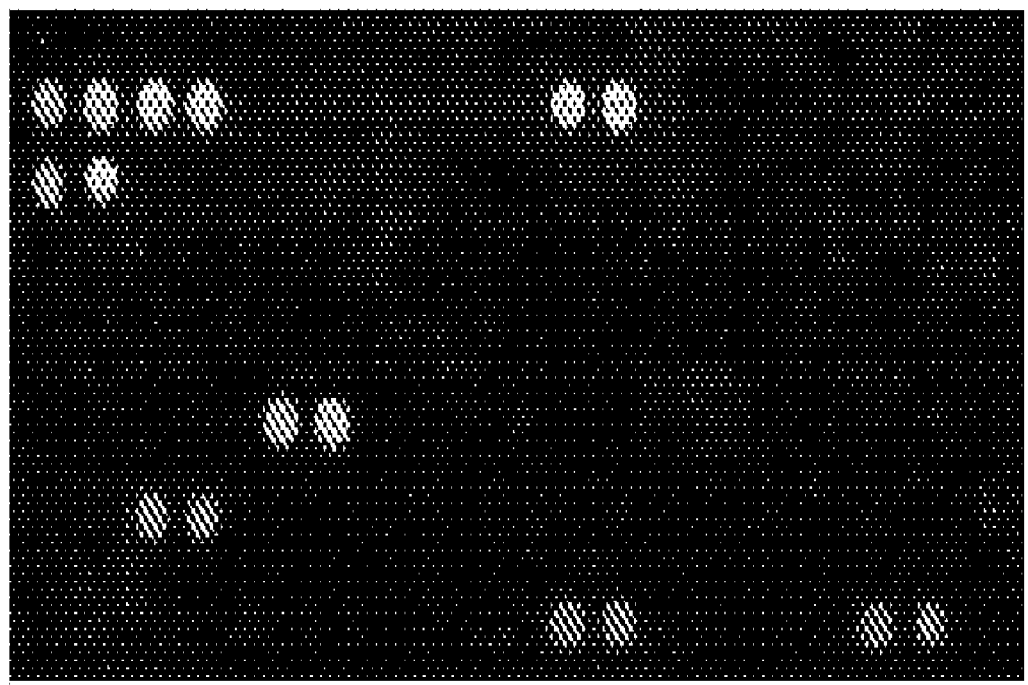

[Fig. 53]
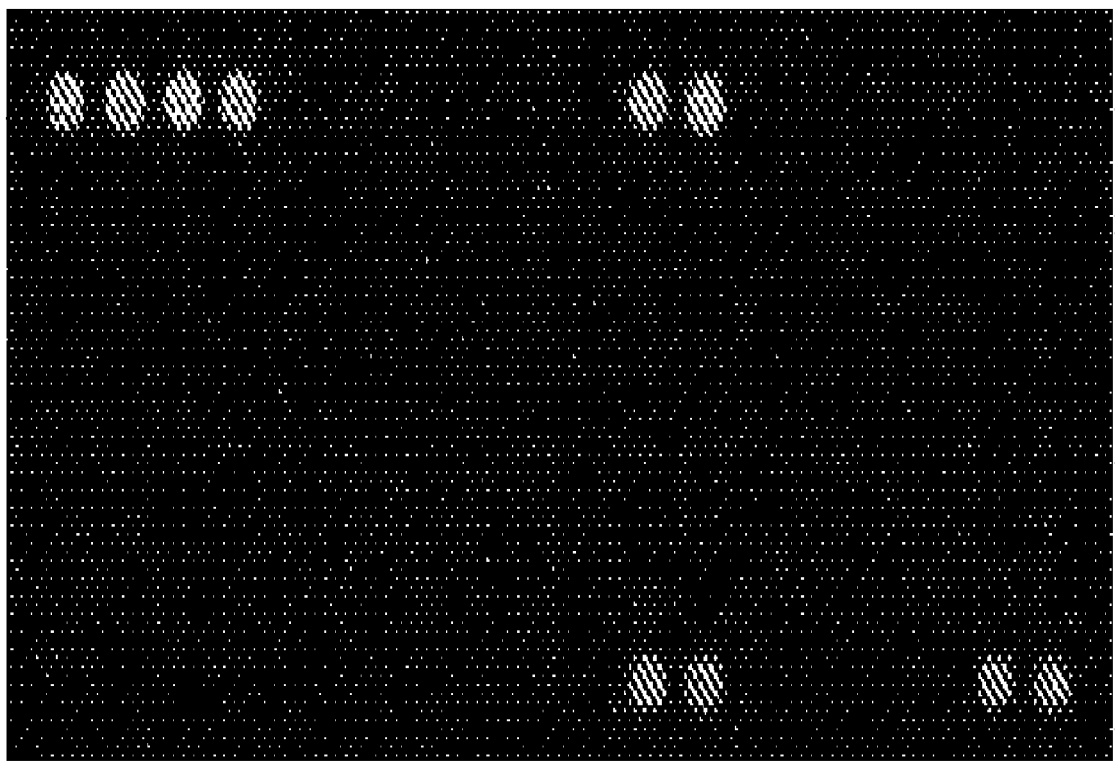

PROBE OF HUMAN PAPILLOMAVIRUS AND DNA CHIP COMPRISING THE SAME

TECHNICAL FIELD

The present invention relates to probes which binds complementarily to the nucleic acid of human papillomavirus (HPV) which is major cause of cervical cancer and which is the most common sexually transmitted disease, a DNA chip or microarray comprising the probe, a diagnosis kit for analyzing genotypes of HPV using them and a method for detecting presence or absence of HPV infection and analyzing genotypes thereof.

BACKGROUND ART

Human papillomavirus (HPV) is a virus that a capsid surrounds double-stranded DNA of genome, and its shape resembles golf ball. HPV is important to human in terms of two viewpoints. Firstly, HPV is the most common sexually transmitted disease (STD). It is reported that 50% or more of all adult women is infected with HPV at least one during their whole life. Secondly, HPV is infected to the human epithelial cell, and induces hyperproliferation. Mostly, such hyperproliferation is a benign tumor such as simple skin wart, condyloma accuminata around external genital organ or anus and the like. However, HPV can be cause of inducing cancer, and actually nearly all cervical cancer, majority of head and neck tumor and numerous anal cancers are induced by HPV (Howley P M. *Virology*. Vol 2, 1996, 2045-2109; Murinoz N et al., *N Engl J Med*, 2003, 348:518-27).

HPV can be classified into following two types. One is a type that invades skin; the other is an anogenital type that invades boundary of skin and mucous membrane of external genital organ or anus. Depending on base sequence of genome, namely phylogenic tree or genotype), HPV can be classified specifically into approximately 120 types. Among them, 45 types of HPV including HPV 16 type (HPV-16), HPV-31, HPV-33, HPV-35, HPV-52, HPV-58, HPV-67, HPV-40, HPV-43, HPV-7, HPV-32, HPV-42, HPV-6, HPV-11, HPV-74, HPV-44, HPV-55, HPV-13, HPV-61, HPV-72, HPV-62, HPV-2, HPV-27, HPV-57, HPV-3, HPV-28, HPV-29, HPV-10, HPV-54, HPV-18, HPV-39, HPV-45, HPV-59, HPV-68, HPV-70, HPV-26, HPV-69, HPV-51, HPV-30, HPV-53, HPV-56, HPV-66, HPV-34, HPV-64 및HPV-73 invade external genital organ and anus. Anogenital types of HPV can be classified into high-risk type and low-risk type and/or middle-risk type depending on ability to induce cervical cancer. High-risk type of HPV includes 22 types of HPV, that is HPV-16, HPV-18, HPV-26, HPV-30, HPV-31, HPV-33, HPV-35, HPV-39, HPV-45, HPV-51, HPV-52, HPV-53, HPV-56, HPV-57, HPV-58, HPV-59, HPV-61, HPV-67, HPV-68, HPV-70, HPV-73, And HPV-82. Among them, the most common high-risk type of HPV is HPV-16, and next is HPV-18, HPV-45, HPV-31, HPV-33, HPV-52 and HPV-58, although there is a difference in worldwide. Low-risk types of HPV includes approximately 20 types of HPV such as HPV-2a, HPV-3, HPV-6, HPV-10, HPV-11, HPV-32, HPV-34, HPV-40, HPV-42, HPV-43, HPV-44, HPV-54, HPV-55, HPV-61, HPV-66, HPV-69, HPV-70, HPV-72, HPV-81, and HPV-CP6108 (Murinoz N et al., *N Engl J Med*, 2003, 348: 518-27).

Genome structure of HPV can be divided roughly into early transcription region E (early gene region), late transcription region L (late gene region), and non-expression region LCR (long control region). Genome structure of HPV affects outbreak type, risk and prognosis of HPV greatly. Particularly, E6 and E7 genes of the E region are integrated in the genome of infected cell, maintained and expressed, thereby played an important role to induce cancer. High-risk types of HPV such as HPV-16, HPV-18 and the like react with the most important tumor suppressor genes in human such as p53, E6AP, retinoblastoma (Rb, P105RB), P107, and P130 and the like and inactivate the tumor suppressor genes. As a result, the infected cell is transformed to cancer cell due to disorder of cell cycle regulation and apoptosis control mechanism. On the contrary, since low-risk types of HPV have low ability to react p53 or Rb tumor suppressor genes and inactivate the tumor suppressor genes, low-risk types of HPV is difficult to induce cervical cancer. Meanwhile, the largest gene of HPV genes is L1. L1 is present in similar preservative base sequence in most HPV types. L1 protein composes primarily of HPV capsid protein, and its antigenecity is the highest (Schneider A. *Science* 1993; 281:263-5; zur Hausen H. *Semin Cancer Biol* 1999; 9:405-11).

Once, cervical cell transformed by HPV is advanced to, so called, carcinoma in situ via precancerous lesion or dysplasia, cervical intraepithelial neoplasma (CIN), or squamous intraepithelial lesion (SIL). If the carcinoma in situ invades base layer under the epithelium cell, it becomes so called carcinoma or invasive carcinoma. 90% or more of HPV infected women removes HPV by means of immune system in body naturally. However, HPV is maintained in 10% of high-risk types of HPV infected women, and it induces cervical cancer. About 8% of precancerous lesions are advanced to carcinoma in situ, and about 20% of carcinoma in situ is developed to cancer. That is, in case that high-risk types of HPV in HPV infected patients are maintained for 10-20 years or more, the high-risk types of HPV induce cervical cancer, and the frequency is estimated to about 0.16%. Since the outbreak of cervical cancer is needed so long time period, and is induced by stages, it is possible to treat or prevent cervical cancer by early examining precancerous lesions in the middle stage of the outbreak. That is, it is possible to block carcinogenesis by removing precancerous lesions with preservative medical operation. Recently, the clinical test regarding vaccine against L1, the major antigen of HPV is in advancing. Also, an attempt to treat cervical precancerous lesions by using vaccines against E6 and E7 of HPV which are major causes inducing cervical cancer is advanced actively. However, for HPV vaccines, it is needed to prepare fixed vaccine by recognizing genotypes of each HPV (Bosch F X et al., *J Clin Pathol*, 2002, 55:244-65. Wallin K et al., *N Engl J Med*, 1999, 341:1633-8; Koutsky L A et al., *N Engl J Med*, 2002, 347: 1645-51).

Since it is very difficult to culture HPV and diagnose it in immunological examination or serum examination, the study regarding HPV is in stepping condition. However, with development of genetic examination method during past 20 years, an attempt to examine genotypes of HPV, thereby developing vaccines for diagnosis, prevention and treatment of HPV and screening cervical cancer using the results of the examination, is in advanced actively.

Particularly, the gene chip (or DNA chip or DNA microarray) was developed in recent by means of the combination of molecular biology and electronics, which can examine from tens to tens of thousands of genes on only one microscopic slide simultaneously. Such DNA chip is a new analytic system, which is applicable to analysis of gene expression, gene diagnosis, gene mutation diagnosis, drug screening and disease screening, and accurate diagnosis of bacteria and virus and the like. Accordingly, development of HPV DNA chip to detect rapidly and accurately high-risk types of HPV related to cervical cancer is attempted in worldwide.

Cervical screening is a conventional examination method used to screen primarily cervical cancer and prelesions thereof. Cervical screening is carried out by swabbing or scraping cervical cell with a tool of which a brush is attached to the tip of the tool, for example cotton stick, and then examining cytological type of the cell. Readout of the cervical screening is classified into normal, atypical squamous cell of unknown significance (ASCUS), low-risk type or low-grade squamous intraepithelial lesion (LSIL), high-risk type or high-grade squamous intraepithelial lesion (HSIL), carcinoma in situ or cancer. The cervical screening is also referred to papanicolou smear examination (Pap smear) according to the inventor. Pap smear examination has been used from 1940s and played an important role to reduce significantly mortality due to cervical cancer. However, Pap smear has disadvantage that false negative rate is high of 30-40%. Such high false negative rate is due to sampling error of sampler or readout error of inspector. Therefore, to avoid sampling error and reduce readout error, liquid based cytology examination, which is also referred to Thin Prep, is attempted in recent. Nevertheless, the false negative rate is still high. Accordingly, in recent ten years an attempt to recognize high-risk types of HPV and predict outbreak risk of cervical cancer by examining presence or absence of HPV infection and genotypes thereof has been accomplished. It is believed that HPV examination has higher screening accuracy than that of Pap smear.

It is recently reported that only one HPV examination can diagnose nearly all high-risk types of prelesions, and one HPV examination has higher accuracy than that of two Pap smear or colposcopic examinations. In addition, a combination of HPV examination and Pap smear can improve both screening sensitivity and specificity, since the combinational examination can solve the problems of Pap examination. Also, the combinational examination has an advantage that time interval of screening examination can be extended from 1 year (for only Pap smear) to 3-4 years. Accordingly, FDA recommends the combinational examination of Pap smear and HPV examination (Ledger W J et al., *Am J Obstet Gynecol*, 2000, 182: 860-5; Wright T C Jr et al., *JAMA*, 2001, 287:2120-9; Wright T C Jr et al., *New Engl J Med*, 2003, 348:6-7; Sherman M E et al., *J Natl Cancer Inst*, 2003, 95; 46-52).

Presently, examination of HPV genes can be divided into two methods. One is a method which examines presence or absence of HPV infection and rough type of HPV. The other is a genotyping method which examines presence or absence of HPV infection and rough type of HPV.

Former methods, namely representative methods which can diagnose HPV infection include PCR based method and hybridization based method. PCR based method is carried out by amplifying major virus capsid L1 gene of which its base sequence in genome of external genital organ type HPV is preserved most or E6 and E7 genes using consensus primer and confirming the results by means of electrophoresis and the like. However, this method can confirm only presence or absence of HPV infection, but cannot examine the genotype or even high-risk type or low-risk type of HPV which is presented. In addition, there are risks of false positive and contamination during the amplification. A representative hybridization based method is a hybrid II capture analytic method (Digene Diagnostics, Inc. USA). The hybrid capture method is carried our by extracting HPV DNA from specimen with hybrid capture technology, hybridizing the HPV DNA with high-risk HPV probe cocktail and low-risk HPV probe cocktail and diagnosing presence or absence of HPV infection. However, hybrid capture method has disadvantages that it is not possible to analyzing accurate genotype of HPV and lower sensitivity of examination due to no amplification. Similar method includes a method carrying out by PCR using consensus primer, hybridization with high-risk HPV probe cocktail and observation of enzyme immune response. This method is relatively simple and is useful for recognizing high-risk type of HPV, but cannot recognize low-risk types of HPV and accurate type of HPV (Kornegay J R et al., *J Clin Microbiol*, 2001, 39:3530-6).

The most standard method, which has been used to recognize presence or absence of HPV infection as well as genotypes thereof, is sequencing after PCR. The method is carried out by amplifying the region which base sequence is preserved in L1 gene and E6/E7 genes of external genital organ and base sequence is different depending on each type; and sequencing the base sequence directly or after cloning. The method is the most golden standard test. However, sequencing method has disadvantage that it can examine only one specimen by one or two examination; a plenty of time and cost are needed; it is labor-intensive. Accordingly, it is difficult to apply the sequencing method to clinical test. Also, although cloning is necessary to recognize complex infection of at least one types of HPV, actually such procedures are impossible. Accordingly, following methods are attempted in place of sequencing method.

First method is a method carrying out several PCR using genotype specific primer according to each HPV types. This method is to recognize various sizes of PCR products by means of electrophoresis or southern blotting for each HPV genotypes. The method is simple, but labor-intensive and inefficient. Also, the method has disadvantage that it can recognize minority of HPV types.

Second method is restriction fragment length polymorphism after PCR (PCR-RFLP). This method is carried out by amplifying L1 gene or E6 and E7 genes with PCR using consensus primer; digesting the PCR products with restriction enzyme; and determining the length of the products by means of electrophoresis. The method is conventional and labor-intensive. Also, the method has disadvantage that it can recognize minority of HPV types (Vermon S D et al. *J Clin Microbiol*, 2000, 38:651-5).

Third method is a reverse hybridization line blot detection method, which is used during recent 6-7 years. The method is carried out by preparing nylon membrane strip which genotype specific oligonucleotide probes for each types of HPV are attached thereon; positioning the consensus primer PCR products of HPV; and determining the types exhibiting the strongest response by hybridization. The method is used in the name of PGMY-line blot assay or SFP10 line probe assay and the like (Gravitt P E et al., *J Clin Microbiol*, 1998, 36:3020-7; van Doorn L et al., *J Clin Microbiol*, 2002, 40:979-983). It is reported that these methods can recognize 25-27 types of HPV in maximum. However, these methods are labor-intensive, difficult to be automated, and cannot recognize all genotypes of HPV. In addition, since target region for determination is localized to 50 bases in certain region of L1 gene, PCR amplification cannot be carried out efficiently due to intragenic variations. Also, the method has disadvantages that to recognize gene variants is difficult, and it can not recognize E6 and E7 genes which played a conclusive role to induce cervical cancer.

Finally, recently, oligonucleotide microarray or DNA chip has been developed and used. The DNA chip uses procedures of the reverse hybridization method above, except that microscopic glass slide is used in place of nylon membrane strip (Cho N H et al. *Am J Obstet Gynecol*, 2003, 188:56-62). The DNA chip can be automated readily compared to reverse hybridization method above. However, the DNA chip has same disadvantages as those of the reverse hybridization method. That is, the DNA chip can not recognize all genotypes of external genital organ HPV, and can recognize only 22 types; since target region for determination is localized to 50 bases in certain region of L1 gene, PCR amplification can not be carried out efficiently; to recognize gene variants is difficult; and it can not analyze E6 and E7 genes.

Conditions that are demanded in reasonable HPV genotype examination method are as follows:
(1) It has to be able to diagnose all types of HPV including complex infection of external genital organ HPV;
(2) All of sensitivity, specificity and reproducibility should be closed to 100%;
(3) It has to be able to analyze L1 gene as well as E6 and E7 genes;
(4) It has to be able to analyze wild type base sequence and mutant base sequence of the genes;
(5) Examination procedures and analysis of the examination results should be simple;
(6) It should be automated to analyze a multiplicity of specimens in short time.

As a result, DNA chip is suitable. However, to date, no DNA chip has been commercialized which satisfies the conditions above. Considering the regional characteristics, it is necessary to produce DNA chips based on the database built by obtaining cervical cell specimens from many Korean women; recognizing genotypes and variation of HPV that is present in the cervical cell specimen.

DISCLOSURE

Technical Problem

The present invention is accomplished to solve the problems above, and provide a probe capable of diagnosing genotype of sexual HPV infection with high selectivity and sensitivity automatically and correctly, which is a major cause of cervical cancer and which is one of the commonest reasons of sexually transmitted diseases.

An aspect of the present invention provides oligonucleotide microarray chip (DNA chip) for probing sexual HPV or analyzing genotype thereof.

Another aspect of the present invention provides all in one kit for probing sexual HPV or analyzing genotype thereof, comprising the probe above, all reagents related to the HPV DNA chip, control specimen and the like.

Another aspect of the present invention provides the probe analyzing genotype of HPV and a method for probing sexual HPV or analyzing genotype thereof using oligonucleotide microarray (oligo DNA chip) comprising the probe.

Technical Solution

The present invention will now be described more fully hereinafter with reference to the accompanying figures, in which preferred embodiments of the invention are shown. This invention may, however, be embodied in many different forms and should not be construed as being limited to the embodiments set forth herein. Rather, these embodiments are provided so that this disclosure will be thorough and complete, and will fully convey the scope of the invention to those skilled in the art.

A probe for analyzing HPV, DNA, kit and analyzing method of the present invention is accomplished with 9 steps as follows:

1. Preparation of Standard and Control Specimen

Human cervical cancer cell lines infected with major types of HPV, 68 cervical cancer tissues sampled from Korean women and 4,898 cervical cell specimens sampled from Korean women were prepared. Positive control and negative control specimens were obtained therefrom (example 1).

2. Isolation of DNA

DNA was isolated from the specimens obtained in the step 1 by using suitable techniques (example 2)

3. PCR

Oligonucleotide primers for amplifying E6/E7 genes, L1 gene of HPV and human beta-globulin gene were selected and designed, and suitable PCR conditions were established. PCR conditions were established for single PCR, duplex PCR, and triplex PCR respectively. In addition, PCR for E6/E7 genes, L1 gene of HPV and human beta-globulin gene were carried out using the DNA isolated in the step 2 as a template (example 3).

4. Sequencing Analysis and Establishment of Clones

After the PCR, sequencing reactions were carried out to analyze base sequence of HPV-E6/E7 and HPV L1, and database was built by sorting out the analyzed information. In addition, PCR products of which their HPV type is confirmed were cloned into plasmid vector. Thereafter, these clones were used as standard and control specimens when establishing reaction conditions of DNA chip of the present invention. Clinical DNA specimens were stored, and then used for analyzing degree of accuracy of the DNA chip of the present invention (examples 4 and 5).

5. Probe Design of DNA Chip

Based on database of E6/E7 and L1 of HPV built-up in the clinical specimens for analyzing HPV genotypes of cervical cells sampled from Korean women in the step 4, and foreign HPV-related databases, oligonucleotide probes capable of analyzing L1 and E6/E6 of external genital organ HPV and human beta-globulin respectively on the DNA chip by hybridization reaction (example 6).

6. Production of DNA Chip

Grid was contrived to array or spot the probes designed in the step 5. And then, the probes mixed with suitable buffer were arrayed or spotted on a glass slide for microscope. After appropriate treatments for stabilization and quality control, the slides were stored for future analysis (example 7).

7. Reaction on the DNA Chip and Establishment of Analyzing Conditions

HPV E6/E7 and HPV L1 genes and beta-globulin gene were amplified by multiplex PCR using standard specimens produced by various combinations and concentrations of one, two or three clones of each HPV type established in the step 4. Suitable conditions were established by positioning the PCR products on the DNA chip, carrying out hybridization reaction several times, and then analyzing by fluorescent scanner (example 8).

8. Clinical Specimen Analysis on the DNA Chip

Multiplex PCR amplification was carried out on the DNA of clinical specimens which presence or absence of HPV and if any, genotype thereof were found. And then, after the PCR products were positioned on the DNA chip produce in the step 6, hybridization reaction was carried out under the conditions established in the step 7. After washing, fluorescent scanner analysis was carried out. Sensitivity, specificity and reproducibility of the DNA chip could be analyzed by such procedures. Also, optimum conditions for the DNA chip of the present invention for diagnosing genotypes of HPV were established again (example 9).

9. Analysis of Correlation with Analyzed Clinical Data After Clinical Analysis on DNA Chip Comparing the results obtained by analysis using the DNA chip after PCR in the step 8 with clinical data obtained by cervical screening and the like, to analyze the correlation and whether the DNA chip is useful for predicting cervical cancer or precancerous lesion. It was found that the DNA chip was useful for analyzing genotypes of HPV as well as screening cervical cancer (example 10).

The present invention provides diagnosis kit (all in one kit) using the DAN chip, comprising 1) tools for sampling clinical specimens such as cervical swab and the like and reagents for extracting DNA from the specimen, 2) reagents for PCR amplifying E6/E7 genes and L1 gene of HPV, and beta-globulin gene, 3) plasmid DNA clones to be used as positive control in amplification of HPV genes, 4) oligo DNA chip for analyzing genotypes of HPV, 5) reaction liquid for hybridization reaction using the DNA chip and washing liquid to be used after the hybridization reaction.

DESCRIPTION OF DRAWINGS

The above and other features and advantages of the present invention will become more apparent by describing in detail exemplary embodiments thereof with reference to the attached drawings in which:

FIG. 1 is an electrophoretic photograph of E6 and E7 genes of HPV, obtained by electrophoresis that is carried out on 2% agarose gel. The E6 and E7 genes were obtained by isolating genome DNA from positive control cell line and then amplifying E6 and E7 genes by PCR using the genome DNA as a template (Lane 1(M): 100 bp DNA size marker, lane 2(N/C): negative control, lane 3 (HPV-16): HPV-16 infected positive control cell line (Caski, ATCC CRL-1550), lane 4 (HPV-18): HPV-18 infected positive control cell line (HeLa, ATCC CCL-2), lane 5 (HPV-35): HPV-35 infected positive control cell line (ATCC 40331)).

FIG. 2 is an electrophoretic photograph of L1 gene of HPV obtained by electrophoresis which is carried out on 2% agarose gel. The E6 and E7 genes were obtained by isolating genome DNA from positive control cell line and then amplifying L1 gene by PCR using the genome DNA as a template (Lane 1(M): 100 bp DNA size marker, lane 2(N/C): negative control, lane 3 (HPV-16): HPV-16 infected positive control cell line (Caski, ATCC CRL-1550), lane 4 (HPV-18): HPV-18 infected positive control cell line (HeLa, ATCC CCL-2), lane 5 (HPV-35): HPV-35 infected positive control cell line (ATCC 40331)).

FIG. 3 is an electrophoretic photograph of E6/E7 genes of HPV and human beta-globulin (HBB) genes obtained by electrophoresis which is carried out on 2% agarose gel. The E6/E7 genes and HBB genes were obtained by isolating genome DNA from positive control cell line and then amplifying the E6/E7 and HBB genes by duplex PCR using the genome DNA as a template (Lane 1(M): 100 bp DNA size marker, lane 2(N/C): negative control, lane 3 (HPV-16): HPV-16 infected positive control cell line (Caski, ATCC CRL-1550), lane 4 (HPV-18): HPV-18 infected positive control cell line (HeLa, ATCC CCL-2), lane 5 (HPV-35): HPV-35 infected positive control cell line (ATCC 40331)).

FIG. 4 is an electrophoretic photograph of L1 gene of HPV and human beta-globulin (HBB) genes obtained by electrophoresis which is carried out on 2% agarose gel. The L1 genes and HBB genes were obtained by isolating genome DNA from positive control cell line and then amplifying the L1 and HBB genes by duplex PCR using the genome DNA as a template (Lane 1(M): 100 bp DNA size marker, lane 2 (HPV-16): HPV-16 infected positive control cell line (Caski, ATCC CRL-1550), lane 3 (HPV-18): HPV-18 infected positive control cell line (HeLa, ATCC CCL-2)).

FIG. 5 is an electrophoretic photograph of L1 gene and E6/E7 genes of HPV and human beta-globulin (HBB) gene obtained by electrophoresis which is carried out on 2% agarose gel. The L1 and E6/E7 genes and HBB genes were obtained by isolating genome DNA from positive control cell line and then amplifying the L1, E6/E7 and HBB genes by triplex PCR using the genome DNA as a template (Lane 1(M): 100 bp DNA size marker, lane 2 (HPV-16): HPV-16 infected positive control cell line (Caski, ATCC CRL-1550), lane 3 (HPV-18): HPV-18 infected positive control cell line (HeLa, ATCC CCL-2)).

FIG. 6 is an electrophoretic peak pattern showing that the results of amplified E6/E7 genes analyzed with ABI prism 377 automated sequencer. The amplified E6/E7 genes were obtained by triplex PCR amplifying L1 gene and E6/E7 genes of HPV, and human beta-globulin (HBB) gene using the DNA extracted from Caski, namely HPV-16 infected cervical cancer cell line. As shown in FIG. 6, the genotype of the HPV is HPV-16.

FIG. 7 is an electrophoretic peak pattern showing that the results of amplified E6/E7 genes analyzed with ABI prism 377 automated sequencer. The amplified E6/E7 genes were obtained by triplex PCR amplifying L1 gene and E6/E7 genes of HPV, and HBB gene using the DNA extracted from HeLa, namely HPV-18 infected cervical cancer cell line. As shown in FIG. 7, the genotype of the HPV is HPV-18.

FIG. 8 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from Caski, namely HPV-16 infected cervical cancer cell line. As shown in FIG. 8, the genotype of the HPV is HPV-16.

FIG. 9 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from HeLa, namely HPV-18 infected cervical cancer cell line. As shown in FIG. 9, the genotype of the HPV is HPV-18.

FIG. 10 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical cancer cell finely dissected in cervical cancer tissue of korean women. As shown in FIG. 10, the genotype of the HPV is HPV-31 which is a kind of high-risk type.

FIG. 11 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical cancer cell finely dissected in cervical cancer tissue of korean women. As shown in FIG. 11, the genotype of the HPV is HPV-35 which is a kind of high-risk type.

FIG. 12 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical cancer cell finely dissected in cervical cancer tissue of korean women. As shown in FIG. 12, the genotype of the HPV is HPV-39 which is a kind of high-risk type.

FIG. 13 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical cancer cell finely dissected in cervical cancer tissue of Korean women. As shown in FIG. 13, the genotype of the HPV is HPV-67 which is a kind of high-risk type.

FIG. 14 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical cancer cell finely dissected in cervical cancer tissue of Korean women. As shown in FIG. 14, the genotype of the HPV is HPV-56 which is a kind of high-risk type.

FIG. 15 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing only the positive reactive change in cervical screening. As shown in FIG. 15, the genotype of the HPV is HPV-6b which is a kind of low-risk type.

FIG. 16 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing only the positive reactive change in cervical screening. As shown in FIG. 16, the genotype of the HPV is HPV-11 which is a kind of low-risk type.

FIG. 17 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing only atypical squamous cell of unknown significance (ASCUS) in cervical screening. As shown in FIG. 17, the genotype of the HPV is HPV-58.

FIG. 18 is an electrophoretic peak pattern showing that the results of amplified L1. gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing microinavasive squamous carcinoma in cervical screening and biopsy. As shown in FIG. 18, the genotype of the HPV is HPV-16.

FIG. 19 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing high-grade squamous intraepithelial lesion in cervical screening and biopsy. As shown in FIG. 19, the genotype of the HPV is HPV-31.

FIG. 20 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing HSIL in cervical screening and biopsy. As shown in FIG. 20, the genotype of the HPV is HPV-18.

FIG. 21 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing HSIL in cervical screening and biopsy. As shown in FIG. 21, the genotype of the HPV is HPV-58 which is a kind of high-risk type.

FIG. 22 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing HSIL in cervical screening and biopsy. As shown in FIG. 22, the genotype of the HPV is HPV-34 which is a kind of high-risk type.

FIG. 23 is an electrophoretic peak pattern showing that the results of amplified L1 gene analyzed with ABI prism 377 automated sequencer. The amplified L1 gene was obtained by triplex PCR amplifying L1 gene and E6/E7 genes of HPV, and HBB gene using the DNA extracted from cervical swab specimen of Korean women showing carcinoma in situ in cervical biopsy. As shown in FIG. 23, the genotype of the HPV is HPV-68.

FIG. 24 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing low-grade squamous intraepithelial lesion (LSIL) in cervical screening. As shown in FIG. 24, the genotype of the HPV is HPV-56.

FIG. 25 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing LSIL in cervical screening. As shown in FIG. 25, the genotype of the HPV is HPV-35.

FIG. 26 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing HSIL and then complex infection of HPV-18 and HPV-70 in cervical screening.

FIG. 27 is an electrophoretic peak pattern showing that the results of amplified L1 gene analyzed with ABI prism 377 automated sequencer. The amplified L1 gene were obtained by triplex PCR amplifying L1 gene and E6/E7 genes of HPV, and HBB gene using the DNA extracted from cervical swab specimen of Korean women showing microinavasive squamous carcinoma and then complex infection of HPV-16 and HPV-52 in cervical screening.

FIG. 28 is a schematic diagram illustrating types and positions positioned on the DNA chip according to an embodiment of the present invention.

FIG. 29 is a front photograph of the DNA chip for diagnosing genotype of HPV according to an embodiment of the present invention.

FIG. 30 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene and E6/E7 genes of HPV, and HBB gene using the DNA extracted from Caski, namely cervical cancer cell line. As shown in FIG. 30, the genotype of the HPV is HPV-16.

FIG. 31 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene and E6/E7 genes of HPV, and HBB gene using the DNA extracted from HeLa, namely cervical cancer cell line. As shown in FIG. 31, the genotype of the HPV is HPV-18.

FIG. 32 is a photograph showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene and E6/E7 genes of HPV, and HBB gene using the DNA extracted from K562, namely non-infected negative control cell line.

FIG. 33 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 33, the genotype of the HPV is HPV-16 which is a kind of high-risk type.

FIG. 34 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 34, the genotype of the HPV is HPV-18 which is a kind of high-risk type.

FIG. 35 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 35, the genotype of the HPV is HPV-31 which is a kind of high-risk type.

FIG. 36 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 36, the genotype of the HPV is HPV-35 which is a kind of high-risk type.

FIG. 37 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 37, the genotype of the HPV is HPV-39 which is a kind of high-risk type.

FIG. 38 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 38, the genotype of the HPV is HPV-67 which is a kind of high-risk type.

FIG. 39 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical cancer cell finely dissected in cervical cancer tissue of Korean women. As shown in FIG. 39, the genotype of the HPV is HPV-56 which is a kind of high-risk type.

FIG. 40 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing only positive reactive change in cervical screening. As shown in FIG. 40, the genotype of the HPV is HPV-6b which is a kind of low-risk type.

FIG. 41 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing only positive reactive change in cervical screening. As shown in FIG. 41, the genotype of the HPV is HPV-11 which is a kind of low-risk type.

FIG. 42 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing atypical squamous cell of unknown significance (ASCUS) in cervical screening. As shown in FIG. 42, the genotype of the HPV is HPV-58 which is a kind of high-risk type.

FIG. 43 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing microinvasive squamous carcinoma in cervical screening and biopsy. As shown in FIG. 43, the genotype of the HPV is HPV-16 which is a kind of high-risk type.

FIG. 44 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing high-grade squamous intraepithelial lesion in cervical screening. As shown in FIG. 44, the genotype of the HPV is HPV-31 which is a kind of high-risk type.

FIG. 45 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 45, the genotype of the HPV is HPV-18 which is a kind of high-risk type.

FIG. 46 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 46, the genotype of the HPV is HPV-58 which is a kind of high-risk type.

FIG. 47 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 47, the genotype of the HPV is HPV-34 which is a kind of high-risk type.

FIG. 48 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing carcinoma in situ in cervical screening. As shown in FIG. 48, the genotype of the HPV is HPV-68 which is a kind of high-risk type.

FIG. 49 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing low-grade squamous intraepithelial lesion (LSIL) in cervical screening. As shown in FIG. 49, the genotype of the HPV is HPV-56 which is a kind of high-risk type.

FIG. 50 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing LSIL in cervical screening. As shown in FIG. 50, the genotype of the HPV is HPV-35 which is a kind of high-risk type.

FIG. 51 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 51, the complex infection of HPV-18 and HPV-70 is found.

FIG. 52 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 52, the complex infection of HPV-16 and HPV-52 is found.

FIG. 53 is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing normal evaluation in cervical screening. As shown in FIG. 53, there is not any HPV infection.

BEST MODE

Hereinafter, the present invention will be described by examples. However, the following examples are only exemplifying the present invention, and the present invention is not limited to the following examples.

Example 1

Preparation of Standard and Control Specimens

Firstly, specimens which will be used as standard or reference and control in future genotype examination and analysis were prepared.

First specimen was human cervical cancer cell lines which are confirmed that presence or absence of HPV and type thereof are confirmed, and has been used widely in study of HPV genotype. The human cervical cancer cell lines were purchased from ATCC (Manassas, Va. 20108, USA) and Korea Cell Line Bank (KCLB) (Seoul University Medical center cancer institute, KOREA), and used after monolayer culturing. The specifications of the cell lines are summarized in Table 1.

Second specimens were obtained from the cervical tissues of women who were diagnosed certainly as cervical cancer or carcinoma in situ lesion and were underwent an operation. After formalin fixation of the specimens, tissues which were stored in paraffin-embedded status were cut into 6-10 microsections at 10 μm of thickness, attached to microscopic slide and microdissected only cancer cells. Among 68 cervical cancer lesions, 61 cases were cervical squamous cell carcinoma, and 7 cases were cervical intraepithelial neoplasma, CIN. Average age distribution the women was 32-69 years old, and average age was 49 years old.

Third, 4,898 cervical specimens were obtained from 4,898 women who went to obstetrics clinic in Korea and were received swab and cervical screening from 2003 in Hamchun Diagnosis Center (Seoul, Korea) and Korea Gynecologic Cancer Foundation (Seoul, Korea). Average age distribution of the women is that 16-19 years old holds 0.2%; twenties hold 18%; thirties hold 38%; forties hold 32%; fifties hold 7%; sixties hold 1% and others hold 3%. In 4,741 cases among the 4,898 cases, the results of cytological and pathological diagnosis were provided by carrying out HPV examination as well as cervical screening and/or biopsy. Cervical cells were sampled by inserting Pap brush (Sanga Medical; songpaku Seoul Korea) or cotton stick into cervix, and rolling the brush or stick to gather well cervical cell. And then, the tip of the Pap brush or the cotton stick was introduced in the tube with screw cap containing sterilized transferring buffer and store. 3 ml of CytoLyt Solution (CYTYC Corporation, Mass. 01719, USA) was primarily used as transferring buffer.

TABLE 1

Specification of control cell line

| Cell line | HPV infection | Infected HPV type |
| --- | --- | --- |
| ATCC 45022 | + | HPV-2a |
| ATCC 45150 | + | HPV-6b |
| ATCC 45151 | + | HPV-11 |
| ATCC 45113 | + | HPV-16 |
| ATCC CRL-1550(CaSki) | + | HPV-16 |
| ATCC 45152 | + | HPV-18 |
| ATCC CCL-2(HeLa) | + | HPV-18 |
| ATCC 65446 | + | HPV-31 |
| ATCC 40331 | + | HPV-35 |
| ATCC 40338 | + | HPV-43 |
| ATCC 45353 | + | HPV-44 |
| ATCC 45548 | + | HPV-56 |
| KCLB-10243* | − | |

Example 2

DNA Isolation

DNA is isolated from the various specimens sampled in the example with suitable methods as follows:

To isolate DNA from cell lines, monolayer cultured cell lines were isolated, introduced into 50 ml centrifugal tube, centrifuged at 3500 rpm for 30 min, decanted to remove supernatants, unpacked pellets with 500 µl of PBS, transferred into 1.5 ml centrifugal tube, and centrifuged at 12,000 rpm for 2 min to remove remaining liquid of medium. Afterwards, 200 µl of PBS liquid and 20 µl, of proteinase K (20 µg/µl) were added to cell pellets, and mixed with shaking magnetic stirrer. 200 µl of GC solution was added, mixed and soublized on 60° C. heating block for 20 min. After completion of reaction, to sample was added to 100 µl of isopropanol and mixed thoroughly. All the solutions were added to filtering column, centrifuged at 10,000 rpm for 1 min. After discarding the filtrates which are passed through the column, added 500 µl of W1 buffer and centrifuged. And then, 500 µl of W2 buffer was added and centrifuged again. The empty column was centrifuged at 12,000 rpm for 2 min to remove ethanol perfectly. Afterwards, 60 µl of sterilized distilled water was added, stood for 10 min and centrifuged at 1,200 rpm for 2 min to obtain DNA.

Also, to isolate DNA from paraffin-embedded cervical tissues, the only cancer cells were dissected from the cervical tissues which were attached on microscopic glass slide at 10 µm of thickness with Pin point Slide DNA Isolation System (Zymo Research, Calif., USA). For each slides, about 1,000 to 2,000 of cells were obtained in liquid form, all the cells were transferred into microcentrifugal tube, treated with 1 ml of xylene twice to remove paraffin, treated with dry ethanol excess xylene, treated with 100 µl of DNA extraction and cell lysis buffer (50 mM KCl, 10 mM Tris-HCl [pH 8.3], 2.5 mM MgCl$_2$, gelatin, 0.45% IGEPAL, 0.45% tween 20, proteinase K [60 µg/ml]), reacted at 55° C. for 3 hours, and heated to 95° C. for 10 min to inactivate proteinase K. After centrifuge, supernatants were used in PCR.

To isolate DNA from cervical swab specimens, DNA was concentrated and purificated with Accuprep Genomic DNA extraction kit (Cat. No. K-3032, Bioneer co., Ltd. Korea). The procedures are as follows: 1.5 ml of cervical cell smear specimens was centri-precipitated at 12,000 rpm for 2 min, added 1.5 ml of phosphate buffered solution (PBS), washed, add suitable amount of proteinase K and cell lysis buffer, and cultured at 60° C. for 20 min. After completion of reaction, the reaction liquid was passed through DNA binding column by centrifugal machine, and washed with washing buffer 1 and 2 by centrifugal machine to harvest DNA.

Example 3

PCR Amplification

To examine genotypes of HPV, firstly E6/E7 genes and L1 gene of HPV were amplified were PCR, and human beta-globulin gene as an internal control was amplified were PCR.

Firstly, for these PCR amplification, oligonucleotide primers were selected and designed. The primers consist of HPCF/HPCR primer that can detect E6/E7 genes of HPV, MY11 and GP6-1 primer (SEQ ID NO. 1) that can detect L1 gene and HBBF/HBBR primer of human beta-globulin gene that is used to confirm efficiency of DNA extraction and PCR. GP6-1 primer is newly designed and the other two primers are selected from known primers. PCR of E6/E7 genes of HPV amplifies products of about 225 bp length, PCR of L1 gene of HPV amplifies products of 182 bp length, and PCR of beta-globulin gene amplifies products of 182 bp length. The base sequences of PCR primer for each genes are summarized in Table 2, and conditions of PCR are as follows:

Each suitable PCR condition was established for single PCR, duplex PCR and triplex PCR. Accordingly, PCR of E6/E7 genes and HPV L1 gene of HPV, and human beta-globulin were carried out by using DNA isolated in the example 2 as an template. The procedures of PCR are as follows:

1. Single PCR

A PCR reaction composition for detecting HPV infection was prepared by, as described in table 2, adding 1 µl (10 pmoles/µl) of each of MY11/GP6-1, HPCF/HPCR and HBBF/HBBR primer to 15 µl of SuperTaq plus pre-mix (10× buffer 2.5 µl, 10 mM MgCl2 3.75 µl, 10 mM dNTP 0.5 µl, Taq polymerase 0.5 µl) purchased from Super Bio Co., Ltd, (Seoul, Korea), further adding 4.0 µl (150 ng/µl) of template DNA of the specimen and finally adding distilled water to adjust the volume of total reaction liquid to 30 µl.

PCR of human beta-globulin was carried out by predenaturing the reaction liquid containing HBB primer at 95° C. for 5 min, repeating 40 cycles at 95° C. for 30 sec, at 50° C. for 30 sec, and at 72° C. for 30 sec, and extending at 72° C. at 5 min.

PCR of E6/E7 of HPV was carried out by predenaturing the reaction liquid containing HPCF/HPCR primer at 95° C. for 5 min, repeating 40 cycles at 95° C. for 30 sec, at 56° C. for 30 sec, and at 72° C. for 30 sec, and extending at 72° C. at 5 min.

PCR of L1 of HPV was carried out by predenaturing the reaction liquid containing MY11 and GP6-1 primer at 95° C. for 5 min, repeating 40 cycles at 95° C. for 30 sec, at 56° C. for 30 sec, and at 72° C. for 30 sec, and extending at 72° C. at 5 min.

2. Duplex PCR

The primer combination of duplex PCR for confirming HPV infection consists of (1) the combination of HPCF/

HPCR primer that detects E6/E7 gene of HPV and HBBF/ HBBR primer that detects beta-globulin gene and (2) the combination of MY11/GP6-1 primer which detects L1 gene of HPV and beta-globulin primer.

Duplex PCR of HPV E6/E7 and HBB genes were carried out as follows: A PCR reaction composition for detecting HPV infection was prepared by adding 1 µl (10 pmoles/µl) of each of HPCF/HPCR and HBBF/HBBR primer to 15 µl of SuperTaq plus pre-mix, further adding 4.0 µl (150 ng/µl) of template DNA of the specimen and finally adding distilled water to adjust the volume of total reaction liquid to 30 µl. PCR was carried out by predenaturing the reaction liquid at 95° C. for 5 min, repeating 30 cycles at 95° C. for 1 min, at 72° C. for 1 min, and at 72° C. for 1 min, and extending at 72° C. at 5 min.

Duplex PCR of HPV L1 and HBB genes were carried out as follows: A PCR reaction composition for detecting HPV infection was prepared by adding 1 µl (10 pmoles/µl) of each of MY11/GPG-1 and HBBF/HBBR primer to 15 µl of Super-Taq plus pre-mix, further adding 4.0 µl (150 ng/µl) of template DNA of the specimen and finally adding distilled water to adjust the volume of total reaction liquid to 30 µl. PCR was carried out by predenaturing the reaction liquid at 95° C. for 5 min, repeating 10 cycles at 95° C. for 1 min, at 72° C. for 1 min, and at 72° C. for 1 min, repeating again 30 cycles at 95° C. for 1 min, at 50° C. for 1 min, and at 72° C. for 1 min and extending at 72° C. at 5 min.

3. Triplex PCR

Triplex PCR of HPV E6/E7, L1 and HBB genes was carried out as follows:

A PCR reaction composition for detecting HPV infection was prepared by adding 1 µl, (10 pmoles/µl) of each of MY11/ GPG-1, HPCF/HPCR and HBBF/HBBR primer to 15 µl of SuperTaq plus pre-mix, further adding 4.0 µl (150 ng/µl) of template DNA of the specimen and finally adding distilled water eo adjust the volume of total reaction liquid to 30 µl. PCR was carried out by predenaturing the reaction liquid at 95° C. for 5 min, repeating 10 cycles at 95° C. for 1 min, at 72° C. for 1 min, and at 72° C. for 1 min, repeating again 30 cycles at 95° C. for 1 min, at 50° C. for 1 min, and at 72° C. for 1 min and extending at 72° C. at 5 min.

The results of the experiments are represented in FIG. 1 to FIG. 5. As shown in FIGS. 1 to 5, the conditions for single, duplex and triplex PCR of HPV were established suitably, and also PCR of both cervical swab specimen and paraffin-embedded cervical cancer tissue was carried out well.

The results of PCR carried out on the 4,898 clinical specimens of cervical cell of L1 and E6/E7 genes of HPV were represented in Table 3. The results of 1,414 cases were positive. Particularly, among them, the cases detected by L1 was about 50%, the cases detected by E6/E7 was about 66%, and the case detected by either L1 or E6/E7 was 50.2% and 34.7%, respectively. It is greatly suggested that when examining cervical cells for HPV detection in clinical test and if the examination is to examine only L1, as in commercialized HPV reverse line hybridization kit and equivalent DNA chips, a majority of HPV will be missed. Also, it is indicated that it is necessary to amplify L1 as well as E6/E7 and confirm their base sequences to screen HPV accurately. This is a important basis for designing characteristic HPV genotype DNA chip of the present invention.

TABLE 2

Primers for PCR

| Gene | SEQ. ID. No. | Name | Base sequence (5'-3') | Length |
|---|---|---|---|---|
| HPV L1 | 1 | MY11 (forward) | GCMCAGGGWCATAAYAATGG | 20 mer |
|  | 2 | GP6-1 (reverse) | AATAAACTGTAAATCATATTCCTC | 24 mer |
| HPV E6/E7 | 3 | HPCF (forward) | TGTCAAAAACCGTTTGTGTTC | 21 mer |
|  | 4 | HPCR (reverse) | GAGCTGTCGCTTAATTGTCC | 20 mer |
| Beta-globulin | 5 | HBBF (forward) | ACACAACTTGTGTTCACTAGC | 21 mer |
|  | 6 | HBBR (reverse) | CAAACTTCATCCACGTTCACC | 21 mer |

TABLE 3

Results of HPV PCR of Korean cervical cell specimens (total 4,898 cases)

| Infection DNA | PCR result positive (%) | Sequencing result positive (%) |
|---|---|---|
| HPV-E6/E7 | 924(65.3) | 649(64.1) |
| HPV-L1 | 704(49.8) | 553(54.6) |
| Both | 214(15.1) | 96(9.5) |
| Either L1 of E6/E7 | 1200(84.9) | 917(90.5) |
| Total | 1414(100) | 1013(100) |

Example 4

Sequencing Analysis and Database Built-up

After the PCR of the example 3, automated sequencing analysis of the PCR products were carried out to analyze base sequence of HPV-E6/E7 and HPV L1, and database was built by sorting out the analyzed information. In addition, clinical DNA specimens which their HPV genotype is confirmed were stored, and then used for analyzing degree of accuracy of the DNA chip of the present invention The procedures of sequencing reaction are as follow:

After sequencing reaction of PCR products was carried out by ABI Prism BigDye Terminator Cycle Sequencing Ready Reaction kit (Perkin Elmer Biosystems, USA), base sequences was analyzed by ABI Prism 377 automated sequencer (Perkin Elmer, USA). The procedures are as follow:

(1) To use the PCR products obtained from each specimens in example 4 as a template of sequencing reaction, the concentration of the PCR products is adjusted suitably. For example, if the length is 100-200 bp, 1-3 ng/µl is needed, and if the length is 200-500 bp, 3-10 ng/µl is needed.

(2) To thin wall microcentrifuge tube is added each PCR products and primer 3.2 pmole, 8 µl of terminator ready reaction mix and sterilized distilled water (up to 20 µl), and mixing it slightly and thoroughly.

(3) Cycle sequencing is carried out with GeneAmp 2700 (PE Biosystems, USA) on the mixture obtained in (2) at 96° C. for 10 sec, at 50° C. for 5 sec, and at 60° C. for 6 min at 25 cycles.

(4) The resulting reactants are precipitated with ethanol and are centrifuged to remove free primer and fluorescence labeled ddNTPs in the terminator ready reaction mix, and dried.

(5) The DNA obtained in (4) are mixed with formamide:25 mM EDTA (pH 8.0):bluedextran mix and 10 µl of loading buffer. After the resulting mixture is denatured in boiling water for 5 min, specimens are stored in refrigerator.

(6) The denatured DNA specimens are loaded into the each well of plate which 5.5% Long Ranger gel (BMA, Cat No. 50611, USA) is casted in advance, electrophoresed for 2-4 hours and sequenced with the sequencer.

According to the analysis results, HPV was found in all 68 cases of total 68 cases. Found types were all, so called, high-risk types. Among them, HPV 16 type was 33 cases; 58 type was 12 cases; 31 type was 11 cases; 18 type and 35 type were 4 cases, respectively; 33 type was 3 cases, and these 7 types hold 99%. Complex infection could not be found by PCR-sequencing.

The types of HPV and the results of base sequence analysis obtained from 1,414 cervical swab specimens which exhibit positive response after PCR in 4,898 cervical swab specimens sampled from Korean women who went to the obstetrics and gynecology clinic for early medical examination of cervical cancer, summarized in the Table 4, and their substantial examples presented in FIG. 7 to 27.

Finally, HPV infection was found in 1,013 cases among 4,898 cases of cervical cell specimens sampled from Korean general adult women, and the frequency was 20.6%. Found HPV types include 35 types, among them 15 types were high-risk type; 11 types were low-risk type; 4 types were middle-risk type; and 5 cases were unknown. High-risk types, which were found, were 838 cases (82.7%), and the frequency was 17.1% as a whole. The results tended to high-risk type of HPV. The reason is why all women received the HPV test for early medical examination of cervical cancer and majority in these women were high-risk type having cervical lesion. It is believed that this conditions corresponds well with the study which primary purpose is to recognize accurately high-risk type of HPV. Regarding the types of HPV that are found, the appearance frequency was HPV-16, HPV-58, HPV-31, HPV-52, HPV-33, HPV-53, HPV-35, and HPV-18 order. HPV-16 was most common. This appearance order is quite different that of America and Europe. In America and Europe, the appearance frequency is HPV-16, HPV-18, HPV-45, HPV-52, HPV-31, HPV-33 and HPV-58 order (Murinoz N et al., *N Engl J Med,* 2003, 348:518-27).

Also one being unique is that there are numerous mutant base sequences which are different from wild type base sequence of American and European database, and are not reported until now in Korea, among base sequence of HPV E6/E7 which are found in the study. It is believed that these type of HPV play a important role to outbreak of cervical cancer.

In addition, as described in the example 3, it is understood that when analyzing the cervical cell swab specimens by sequencing after PCR, the possibility to find HPV infection by analysis with only HPV L1 was 50% or less, and in case of reminder, it was possible to fine HPV infection by combinational analysis of HPV L1 and HPV E6/E7. Also, unique base sequence of Korean women should be considered. These results of detailed prestudy about HPV genotype of Korean women become important basis of (1) combinational analysis of L1 and E6/E7 of HPV, (2) indigenous idea of the DNA chip of the present invention considering base sequence of Korean women HPV.

TABLE 4

| Total specimens | | 4898 | |
|---|---|---|---|
| Specimens found HPV (%) | | 1414 (28.9%) | |
| HPV type and specimens found HPV (%) | | 1013(20.7%) | |
| Risk | HPV type | Case | % |
| High-risk | 16 | 351 | 35 |
| | 18 | 27 | 3 |
| | 31 | 83 | 8 |
| | 33 | 52 | 5 |
| | 34 | 1 | 0 |
| | 35 | 35 | 3 |
| | 39 | 8 | 1 |
| | 52 | 52 | 6 |
| | 53 | 40 | 4 |
| | 56 | 5 | 0 |
| | 58 | 131 | 13 |
| | 66 | 22 | 2 |
| | 67 | 8 | 1 |
| | 68 | 10 | 1 |
| | 70 | 6 | 1 |
| Low-risk | 6 | 25 | 2 |
| | 11 | 15 | 1 |
| | 54 | 2 | 0 |
| | 61 | 28 | 3 |
| | 62 | 13 | 1 |
| | 63 | 1 | 0 |
| | 64 | 1 | 0 |
| | 72 | 3 | 0 |
| | 74 | 1 | 0 |
| | 83/MM7 | 6 | 1 |
| | LVX160 | 19 | 2 |
| Middle-risk | 82/MM4 | 2 | 0 |
| | 84/MM8 | 14 | 1 |
| | CP4173 | 6 | 1 |
| | CP8304 | 19 | 2 |
| Unknown | 71 | 8 | 1 |
| | 87 | 1 | 0 |
| | CP8061 | 6 | 1 |
| | IS887 | 4 | 0 |
| | JC9710 | 1 | 0 |
| Total | | 1013 | 100 |

For FIGS. 26 and 27, peak in the electrophoretic peak pattern was overlapped. It is a phenomenon that appears when analyzing several different template DNA, namely when various types of HPV are mixed. In this case, only portion thereof can be confirmed by blast search. It means that PCR products are cloned and numerous clones should be analyzed by sequencing. In this case, the DNA chip, which can analyze complex HPV infection, is very useful. Actually, for the above case, the presence of the complex infection of HPV-18 and HPV-70 (see FIG. 51) and the complex infection of HPV-16 and HPV-52 (see FIG. 52) was found by the DNA chip of the present invention.

Example 5

Establishment of Clones for HPV Analysis

After the PCR of the example 4, PCR products of which their HPV type was confirmed by sequencing method were cloned by using plasmid vector and *E. coli*. Thereafter, these clones were used as standard and control specimens when establishing reaction conditions of DNA chip of the present invention. The cloning method is as follows:

1) After isolating the PCR products obtained by PCR amplifying E6/E7 genes and L1 gene with Gel recovery kit (Zymo Research, USA) in agarose gel, the their concentrations were determined by spectrometer or on agarose gel.

2) pGEM™-T Easy Vector (Promega, A1360, USA) and 2× Rapid Ligation Buffer stored at −20° C. were melted, mixed by shaking the tube slightly with fingers, centrifuged at low speed, mixed with insert DNA to be cloned in the ratio described in Table 5 and introduced into 0.5 ml tube, thereby preparing ligation reaction.

TABLE 5

|  | Standard reaction | Positive control | Background control |
| --- | --- | --- | --- |
| 2× Rapid Ligation Buffer, T4 DNA Ligase | 5 µl | 5 µl | 5 µl |
| pGEM ™-T Easy Vector (50 ng) | 1 µl | 1 µl | 1 µl |
| PCR product | X µl* | — | — |
| Control Insert DNA | — | 2 µl | — |
| T4 DNA Ligase(3 Wess units/µl) | 1 µl | 1 µl | 1 µl |
| Final volume | 10 µl | 10 µl | 10 µl |

*PCR products and plasmid vector are controlled in ratio of 3:1. That is, 3.0 kb of vector 50 ng of vector (size 3.0 kb) is mixed with 12.4 ng of PCR product (size 0.25 kb) and 22.5 ng of PCR product (size 0.45 kb) respectively.

3) After mixing each reaction liquid thoroughly with pipette, ligation reaction was carried out at room temperature for about an hour. If numerous products are required, ligation reaction is carried out at 4° C. overnight.

4) Such ligated samples were transformed with 50 µl of JM109 competent cell ($\geq 1 \times 10^8$ cfu/µg DNA) stored at −70° C.

5) Firstly, to 1.5 ml tube was added 2 µl of the ligated products and competent cell 50 µl of competent cell melted in ice bath immediately before adding. The mixture was mixed thoroughly, and reaction was carried out in ice for 20 min.

6) The tube was stood in ice bath for 2 min immediately after heat shock in 42° C. of incubating water bath for 45-50 sec.

7) After adding 950 µl of SOC medium set to room temperature to the tube, it was incubated in shaker at 37° C. for about one and half hour.

8) About 100 µl of the culture was applied to LB/ampicillin/IPTG/X-Gal plate. After reversing the plate and incubating in shaker at 37° C. for 16-24 hours, colony counting was carried out. And then only white colony was selected and cultured in 3 ml of LB/ampicillin broth. Plasmid DNA was mini prepared. Correct insertion of insert DNA into the vector was confirmed by PCR or restriction enzymes. For more accurate analysis, all clones obtained by such procedures were analyzed by automated sequencer.

Example 6

Probe Design of DNA Chip

The example explains the design process of oligonucleotide probes to be positioned on the DNA chip. It is the core of the present invention.

After analyzing the huge database containing the information regarding base sequence of E6/E7 and L1 of HPV in the 1,013 clinical specimens obtained by isolation of DNA from benign and malignant cervical specimens of Korean women and confirmation by PCR as described in the examples 4 and 5, and HPV-related database of USA, intra variants which are presented in each genes were also analyzed according to HPV genotypes and the frequency thereof in each human races. By such procedures, 40 genital types of HPV invading cervix were selected; oligonucleotide probes for analyzing genotypes of the HPV types, and the base sequences were summarized in the Table 5.

Probes were designed to make oligonucleotide probes as genotype specific probe, which can bind specifically to DNA of L1 gene and E6/E7 genes, according to the object of the present invention.

Firstly, putting all database together, that is (1) HPV database of National Center for Biotechnology Information (NCIB) in USA, (2) HPV database of LOS ALAMOS in USA, and (3) database of 35 types of HPV found in the cervix of Korean women in the example 4, base sequences of genome DNA obtained from total 76 types of HPV including HPV-1a, -2a, -3, -4, -5, -6b, -7, -8, -9, -10, -11, -12, -13, -15, -16, -16r, -17, -18, -19, -20, -21, -22, -23, -24, -25, -26, -27, -28, -29, -30, -31, -32, -33, -34, -35, -35h, -36, -37, -38, -39, -40, -41, -42, -44, -45, -47, -48, -49, -50, -51, -52, -53, -54, -55, -56, -57, -58, -59, -60, -61, -63, -65, -66, -67, -68, -70, -72, -73, -75, -76, -77, -80, MM4, MM7, MM8, and CP8304, were established. After executing the computer program DNASTAR (MegAlign™ 5, DNASTAR Inc.) on the obtained DNA sequences (pairwise alignment and multiple sequence alignment) with ClustalW method, phylogenetic tree was drawn up. After screening genotype specific base sequence for each group, genotype specific probes were designed with computer program, primer premier 5 (PREMIER Biosoft International Co.). In this case, setting 20 Ap and 18 Ap bb of oligonucleotide of probe length, 110 genotype specific probes were designed primarily. The DNA chip and diagnosis kit for diagnosing genotypes of HPV are characterized in that the analysis targets of the DNA probes are total 40 types of L1 genes including 8 high-risk HPV E6/E7 genes, 20 high-risk HPV L1 genes, 17 low-risk HPV L1 genes, and 3 middle-risk HPV L1 genes, wherein high-risk HPV types include HPV-16, HPV-18, HPV-31, HPV-33, HPV-35, HPV-52, HPV-58, HPV-67, HPV-26, HPV-30, HPV-34, HPV-39, HPV-45, HPV-51, HPV-53, HPV-56, HPV-57, HPV-66, HPV-68, and HPV-70; low-risk HPV types include HPV-6, HPV-7, HPV-10, HPV-11, HPV-27, HPV-32, HPV-40, HPV-42, HPV-44, HPV-54, HPV-55, HPV-59, HPV-61, HPV-62, HPV-72, HPV-73 and HPV-83; middle-risk HPV types include HPV-MM4/82, HPV-MM8/84 and HPV-CP8304/81.

Virtual binding ability of total 110 probes designed by the procedures above to the obtained total 76 different types of HPV was analyzed by means of computer program Amplify 1.2 (University of Wisconsin). In the example, probes of HPV-16, HPV-58, HPV-31 and HPV-33 that are common to Korean and are closely related to cervical cancer were designed. Next, probes were selected according to its ability to genotype specifically bind to HPV-39, HPV-45, HPV-51, HPV-56, HPV-59, HPV-61, HPV-68, HPV-70, HPV-73, HPV-74, HPV-6, HPV-7, HPV-11, HPV-32, HPV-34, HPV-40, HPV-42, HPV-44, HPV-55 and HPV-66. Names, SEQ ID Nos. and types are summarized in Table 6 and 7.

TABLE 6

Base sequence of oligonucleotide probes

| SEQ. ID. No. | Name | Sequences (5'-3') | Length |
| --- | --- | --- | --- |
| 7 | 16W | TTGTTGCAGATCATCAAGAA | 20 mer |
| 8 | 18W | CACGACAGGAACGACTCC | 18 mer |
| 9 | 31W | CAAGTGTAAACATGCGTGG | 19 mer |
| 10 | 33W | CTGTGACGTGTAAAAACGCC | 20 mer |
| 11 | 35W | GTCCTGTTGGAAACCAAC | 18 mer |

TABLE 6-continued

Base sequence of oligonucleotide probes

| SEQ. ID. No. | Name | Sequences (5'-3') | Length |
|---|---|---|---|
| 12 | 52W | GACCCCGACCTGTGACC | 17 mer |
| 13 | 58W | CCGACGTAGACAAACAC | 17 mer |
| 14 | 67W | GAAGCCATGCGTGGAG | 16 mer |
| 15 | 16L1 | TGCCATATCTACTTCAGAAACT | 22 mer |
| 16 | 18L1 | TGTTTGCTGGCATAATCAATTA | 22 mer |
| 17 | 31L1 | GTCTGTTTGTGCTGCAATT | 19 mer |
| 18 | 33L1 | CAGTACTAATATGACTTTATGCACA | 25 mer |
| 19 | 35L1 | TCTGCTGTGTCTTCTAGTGACAGTA | 25 mer |
| 20 | 52L1 | TGACTTTATGTGCTGAGGTTAAA | 23 mer |
| 21 | 58L1 | GCACTGAAGTAACTAAGGAAGGTAC | 25 mer |
| 22 | 67L1 | AAAATCAGAGGCTACATACAAAA | 23 mer |
| 23 | 26L1 | CCTTACCATTAGTACATTATCTGCA | 25 mer |
| 24 | 30L1 | AACCACACAAACGTTATCCA | 20 mer |
| 25 | 34L1 | CCACAAGTACAACTGCACC | 19 mer |
| 26 | 39L1 | ACCTCTATAGAGTCTTCCATACCTTCTAC | 29 mer |
| 27 | 45L1 | CACAAAATCCTGTGCCAAG | 19 mer |
| 28 | 51L1 | GGTTTCCCCAACATTTACTC | 20 mer |
| 29 | 53L1 | GCAACCACACAGTCTATGTCTACA | 24 mer |
| 30 | 56L1 | GACTATTAGTACTGCTACAGAACAGTTAAGTAAA | 34 mer |

TABLE 7

Base sequence of oligonucleotide probes

| SEQ. ID. No. | Name | Sequences (5'-3') | Length |
|---|---|---|---|
| 31 | 57L1 | CCACTGTAACCACAGAAACTAATT | 24mer |
| 32 | 66L1 | AATGCAGCTAAAAGCACATTAACTAA | 26mer |
| 33 | 68L1 | CTACTACTACTGAATCAGCTGTACCAAATAT | 31mer |
| 34 | 70L1 | CCGAAACGGCCATACCT | 17mer |
| 35 | MM4L1/82 | CATTTGCTGGAATAATCAGC | 20mer |
| 36 | MM8L1/84 | TATATGCTGGTTTAATCAATTGTT | 24mer |
| 37 | CP8304L1/81 | GCTACATCTGCTGCTGCAGA | 20mer |
| 38 | 6L1 | TTTGTTGGGGTAATCAACTG | 20mer |
| 39 | 7L1 | ACACCAACACCATATGACAATA | 22mer |
| 40 | 10L1 | GCAGTACCAATATGTGCTGTG | 21mer |
| 41 | 11L1 | ATTTGCTGGGGAACCAC | 18mer |

TABLE 7-continued

Base sequence of oligonucleotide probes

| SEQ. ID. No. | Name | Sequences (5'-3') | Length |
|---|---|---|---|
| 42 | 27L1 | CAGCTGAGGTGTCTGATAATACTAAT | 26mer |
| 43 | 32L1 | GACACATACAAGTCTACTAACTTTA | 25mer |
| 44 | 40L1 | AGTCCCCCACACCAAC | 16mer |
| 45 | 42L1 | CACTGCAACATCTGGTGA | 18mer |
| 46 | 44L1 | TACACAGTCCCCTCCGTC | 18mer |
| 47 | 54L1 | TACAGCATCCACGCAGG | 17mer |
| 48 | 55L1 | CTACAACTCAGTCTCCATCTACAA | 24mer |
| 49 | 59L1 | TCTATTCCTAATGTATACACACCTACCAG | 29mer |
| 50 | 61L1 | TGCTACATCCCCCCCTGTAT | 20mer |
| 51 | 62L1 | ACTATTTGTACCGCCTCCAC | 20mer |
| 52 | 72L1 | CACAGCGTCCTCTGTATCAGA | 21mer |
| 53 | 73L1 | AGGTACACAGGCTAGTAGCTCTACTAC | 27mer |
| 54 | MM7L1/83 | TGCTGCTACACAGGCTAATGA | 21mer |
| 55 | HBB | GAGGAGAAGTCTGCCG | 16mer |

Example 7

Production of DNA Chip

After contriving grid according to the probes designed in the example 6, probes mixed with suitable buffer were spotted to microscopic glass slide. And then, the slide was stabilized with suitable treatments, quality controlled and stored until examination.

The process for producing DNA chip is as follows: Preparation of order grid to be positioned on the DNA chip In the present invention, to determine rapidly and easily whether the analyzed genotype is high-risk types, middle-risk types or low-risk types, grouping grid was prepared. The order of the grip was shown in FIG. 28. According to FIG. 28, 8 types of E6/E7 probes of HPV high-risk types and 20 types of L1 probes of HPV high-risk types were spotted on the left, L1 probes of HPV middle-risk types were spotted on the center and 17 types of L1 probes of HPV low-risk types were spotted on the right. Also, corner marker and oligonucleotide probes which are specific for human beta-globulin gene to confirm suitability of DNA isolation and PCR amplification were spotted on the top of left (2 probes), the top and bottom of center (2 probes) and the bottom of right (1 probe).

In addition to the human beta-globulin gene, actin, glyceraldehydes-3-phosphate dehydrogenase gene and the like can be used as standard marker probe.

Each oligonucleotide probe was spotted with arrayer. In this case, same probes were spotted in duplicate in order that each genotypes of HPV is exhibited two times in minimum and four times in maximum. In the present invention, the reasons that oligonucleotide probes of 8 HPV E6/E7 gene were added are as follows. At First, The 8 genotypes exists at most high frequency in worldwide including Korean. At Second, the 8 types of HPV are representative high-risk type and are closely related to outbreak of cervical cancer. At Third, it is important to recognize accurate genotype of E6/E7 in case of administrating vaccines against high-risk types of HPV. At Fourth, since in case of these types, L1 gene can not be amplified by means of PCR due to intragenic variation during PCR process, it is necessary to address such problems and compensate the results by means of amplification of E6/E7 genes. These viewpoints become the important basis of the DNA chip of the present invention, and play important roles to improve analysis accuracy of HPV genotypes in the DNA chip of the present invention.

It is one of important characteristics of the DNA chip of the present invention that grid illustrated in FIG. 28 exists repetitively on the 6 to 8 compartments divided on the one DNA chip (See FIG. 29). Accordingly, the DNA chip can analyze 6 to 8 different specimens on the only one chip, and is very useful for saving time, labor and cost.

2. Preparation of Solution for Spotting Synthesized Oligonucleotide Probes and Dispensation into Master Plate Oligonucleotides which amine is attached to C6 moiety, synthesized according to the example were purified with HPLC, and solublized in third distilled water to adjust final concentration of 200 pmole/μl. Such prepared oligonucleotide probes were mixed with spotting solution, micro spotting solution Plus (Telechem, TC-MSP, USA) to adjust concentration of 38 pmole/μl. That is, 7.7 μl of 200 pmole/μl oligonucleotide probe was mixed with 32.4 μl of spotting solution to make final volume of 40 μl. The resulting mixtures were dispended into 96-wel master plate in order.

3. Spotting of Oligonucleotide Probes on Glass Slide with Arrayer

Spotting solution containing oligonucleotide probes was spotted (arrayed) in duplicate (double hit) from the 96-well master plate on specially coated glass slide with arrayer. One spot contained average about 0.005 μl of probe solution. A slide which is a base material of the DNA chip, such as BMT aldehyde glass slide (Biometrix technology, Korea) which super aldehyde is coated, is preferable. Arrayer such as GMS 417 arrayer (Pin-Ring Type, Affymetrix, USA)꽃 MGII (Biorobotics Inc, Mass. 01801, USA), or equivalents, is preferable.

4. Induction of Schiff Base Reaction of Spotted Oligonucleotide Probes with Aldehyde Group of Glass Slide and Post-Treatment The DNA chip produced by spotting the probes to glass slide as described above was placed into glass jar which humidity is maintained to 80%, and reacted at room temperature for 15 min. After completion of the reaction, the immobilized slide was placed into dry oven, baked at 120° C. for 1 hour and 30 min, washed with sodium dodecyl sulfate (SDS) solution for 2 min twice, dipped into third distilled water at 95° C. for 3 min to denature immobilized oligonucleotide probes, and washed again with third distilled water for 1 min. After washing, the slide was reduced in blocking solution (1 g of NaBH4, 300 ml of phosphate buffered solution (PBS), 100 ml of ethanol) for 15 min, washed in 0.2% sodium dodecyl sulfate solution for 2 min twice, washed in third distilled water for 2 min twice, centrifuged at 800 rpm for 1 min and 30 sec to remove moisture, placed into slide box and stored in desiccator.

The resulting DNA chip of the present invention was quality controlled by means of the method such as the following example 8.

Example 8

Hybridization Reaction on the DNA Chip and Establishment of Analytic Conditions

HPV E6/E7 and HPV L1 genes and betaglobulin gene were amplified by multiplex PCR using 100 artificial standard specimens produced by various combinations and concentrations of one, two or three clones of each HPV type established in the example 5. Suitable conditions were established by positioning the PCR products on the DNA chip, carrying out hybridization reaction more than three times, and then analyzing by fluorescent scanner. The procedures are as follow:

1. PCR

PCR of E6/E7 and L1 genes of HPV, and human betaglobulin gene was carried out by using the procedures described in the example 3, with provided that for a reverse primer among the combination of primers, namely GP6-1, HPCR and HBBR, oligonucleotides labeled by Cy-5 fluorescent was used.

Cy-3, biotin-binding material, 5-2'-(aminoethyl)amino-1-naphalene sulfate (EDANS), tetramethylrhodamine (TMR), tetramethylrhodamine isocyanate (TMRITC), x-rhodamine and TEXAS RED can be used as the labeling marker.

2. Hybridization Reaction

Hybridization reaction was carried out by positioning HPV PCR products amplified by PCR on the slide substrate which various oligonucleotide probes were immobilized thereon. 100 μl perfusion 8 wells chamber (Schleicher & Schuell BioScience, German) was used as hybridization reaction chamber.

10 μl of each amplified products of E6/E7 genes, HBB gene and L1 gene were mixed, and tertiary distilled water was added to the mixture to make 50 μl of final volume. After denaturing at 95° C. for 5 min, the mixture was stood in ice for 3 min immediately. And then, after adding 50 μl of hybridization reaction liquid (2 ml of 20×SSC, 1.7 ml of 90% glycerol, and 6.3 ml of 50 mM PBS was mixed and adjusted final volume to 10 ml) to make 100 μl of final volume, reacting it with probes immobilized on slide at 45° C. for 30 min.

3. Washing

After hybridization reaction, removing well cover from the DNA chip, washing the slide with 3×SSPE solution at ambient temperature for 2 min, and washing the slide again with 1×SSPE solution at ambient temperature for 2 min, and then centrifuging the slide at ambient temperature and 800 rpm for 1 min and 30 sec to dry it.

4. Scanning

After hybridization, the dried slide which nonspecific signals were removed by washing and centrifuging was scanned with confocal laser fluorescence scanner to analyze fluorescent signals and images. Scanner used in the scanning includes Affymetrix 428 Array Scanner (Affymetrix, USA) or ScanArray Lite (Packard Bioscience, USA), or equivalents thereof.

Example 9

Analysis of Clinical Specimens on the DNA Chip

Multiplex PCR amplification was carried out on the DNA of clinical specimens which presence or absence of HPV and if any, genotype thereof were found by sequencing after PCR.

And then, after the PCR products were positioned on the DNA chip produce in the examples 6 and 7, hybridization reaction was carried out by procedures of example 8. After washing, fluorescent scanner analysis was carried out. Sensitivity, specificity and reproducibility of the DNA chip could be analyzed by such procedures. Also, optimum conditions for the DNA chip of the present invention for diagnosing genotypes of HPV were established again. The results were shown in FIG. 30 to FIG. 53.

FIGS. 30 to 32 is a photography of DNA microarray hybridization reaction results using 30 pairs of HPV type probes synthesized with Caski, HeLa and K-562, respectively. In these Figures, circles represent a position depending on the kind of probe. As shown in these figures, cross-hybridization among the different probes was not occurred, and hybridization reaction was occurred in HPV-16 and HPV-18 specifically, respectively.

FIGS. 33 to 52 is a photography of DNA microarray hybridization reaction results using 48 pairs of oligonucleotide probes spotted on the DNA chip of the present invention respectively. In these Figures, circles represent a position depending on the kind of probe. As shown in these figures, the results of hybridization reaction caused by the plasmid DNA amplification products illustrates that there was no cross-hybridization, and type-specific expression was occurred in only inherent probes, respectively.

Namely, 48 pairs of each HPV type probes in the DNA chip produced in the present invention were bound to certain type of HPV DNA specifically and there was no cross-hybridization. In addition, complex infected specimens mixed with at least one type of HPV were diagnosed accurately. That is, for diagnosing genotype of single or complex infection HPV, the DNA chip of the present invention exhibited 100% of sensitivity and 100% of specificity. In addition, regarding that the same results of the 3 or more repetitive tests that are carried out by different inspectors with time intervals, the reproducibility of the DNA chip was 100%. Regarding the results, it is believed that the 48 pairs of the probes synthesized in the present invention can analyze accurately numerous combinations of HPV types that were not considered in the examples of DNA microarray hybridization reaction.

Particularly, FIG. 51 is a photography taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 51, the complex infection of HPV-18 and HPV-70 was found. In this case, only HPV-70 was found in the first direct sequencing assay, and HPV-18 was found additionally in the second sequencing assay after cloning. However, the DNA chip for analyzing genotypes of HPV of the present invention can analyze complex infection of HPV-18 and HPV-70 readily and rapidly in only one assay.

Also, FIG. 52 is case proving that the presence of cervical carcinoma in situ was confirmed by biopsy afterward, and is a photograph taken by fluorescent scanner showing that the results of amplified L1 gene, E6/E7 genes and HBB gene analyzed with the DNA chip for diagnosing genotype of HPV according to an embodiment of the present invention. The amplified L1 gene, E6/E7 genes and HBB gene were obtained by triplex PCR amplifying L1 gene, E6/E7 genes and HBB gene using the DNA extracted from cervical swab specimen of Korean women showing HSIL in cervical screening. As shown in FIG. 52, the complex infection of HPV-16 and HPV-52 was found. In this case, it was not able to recognizing in the first direct sequencing assay, and HPV-18 and HPV-52 were found together in the second sequencing assay after cloning. However, the DNA chip for analyzing genotypes of HPV of the present invention can analyze complex infection of HPV-18 and HPV-70 readily and rapidly in only one assay.

Namely, it can be recognized that the DNA chip produced in the present invention can discriminate accurately each type of HPV from cervical swab specimens in clinical test. Each HPV type probes were bound to certain type of HPV DNA specifically and there was no cross-hybridization. In addition, complex infected specimens mixed with at least one type of HPV, which were difficult in diagnosis by direct sequencing and were able to recognizing by many sequencing assays after cloning, were diagnosed accurately. That is, for diagnosing genotype of single or complex infection HPV, the DNA chip of the present invention exhibited 100% of sensitivity and 100% of specificity. In addition, regarding that the same results of the 3 or more repetitive tests that are carried out by different inspectors with time intervals, the reproducibility of the DNA chip was 100%.

Example 10

Correlation Analysis with Clinical Data after Analyzing Clinical Specimens on the DNA Chip Comparing the results obtained by analysis using the DNA chip after PCR in the example 9 with clinical data obtained by cervical screening and the like, to analyze the correlation and whether the DNA chip is useful for predicting cervical cancer or precancerous lesion. It was proved that the DNA chip was useful for analyzing genotypes of HPV as well as screening cervical cancer. The procedures are as follow:

First, HPV types were analyzed by the DNA chip of the present invention and sequencing method in paraffin-embedded 68 cervical cancer tissues and 49 normal cervix tissue specimens. The results indicated that high-risk type of HPV was found in all 68 cervical cancer tissues. On the contrary, there was no any high-risk type of HPV, and were low risk type of HPV in low frequency (5 cases; 10.2%) in normal cervix tissues. Such results proved that the DNA chip can predict conditions of cervical cancer, and particularly is useful for selective analysis of cervical cancer and cervix carcinoma in situ. Additionally, the analytic study (prospective blind study) using the DNA chip of the present invention and sequencing method was performed in concurrent with cervical colposcopy, cervical scanning, cervical smear screening and cervical biopsy on cervical swab specimens obtained from 20 adult women who went to domestic obstetrics via cooperation of Korean Genecologic Cancer Foundation (KGCF), and the results of the study were analyzed. The correlation of the results obtained by cervical screening and biopsy of volunteers with the results obtained by HPV DNA chip assay and sequencing method was shown in Table 8.

The results indicated that high-risk type of HPV was found in the form of single or complex infection in cervical cancer as well as precancerous lesion, both HSIL and LSIL. On the contrary, there was no any high-risk type of HPV in normal cervix tissues. Such results also proved that the DNA chip can predict conditions of cervical cancer, and particularly is useful for selective analysis of cervical cancer and precancerous lesion, both HSIL and LSIL. In addition, it was reconfirmed that the DNA chip assay can recognize complex HPV infection that was not able to recognizing by sequencing method.

While the present invention has been particularly shown and described with reference to exemplary embodiments thereof, it will be understood by those of ordinary skill in the art that various changes in form and details may be made therein without departing from the spirit and scope of the present invention as defined by the following claims.

TABLE 8

Comparison the results of antegrade blind test with the results of DNA chip diagnosis

| Specimen | Pathological readout | DNA chip readout | Sequencing readout |
|---|---|---|---|
| 1 | Carcinoma in situ | HPV-16 | HPV-16 |
| 2 | High-grade squamous intraepithelial lesion (HSIL) | HPV-31 | HPV-31 |
| 3 | HSIL | HPV-58 | HPV-58 |
| 4 | HSIL | HPV-34 | HPV-34 |
| 5 | Carcinoma in situ | HPV-68 | HPV-68 |
| 6 | HSIL | HPV-56 | HPV-56 |
| 7 | Low-grade squamous intraepithelial lesion (LSIL) | HPV-35 | HPV-35 |
| 8 | HSIL | HPV-18 & 70 | HPV-18 |
| 9 | Squamous cell carcinoma | HPV-16 & 52 | Unknown |
| 10 | HSIL | HPV-18 | HPV-18 |
| 11 | Normal | Negative | Negative |
| 12 | Normal | Negative | Negative |
| 13 | Normal | Negative | Negative |
| 14 | Normal | Negative | Negative |
| 15 | Normal | Negative | Negative |
| 16 | Normal | Negative | Negative |
| 17 | Normal | Negative | Negative |
| 18 | Normal | Negative | Negative |
| 19 | Normal | Negative | Negative |
| 20 | Normal | Negative | Negative |

INDUSTRIAL APPLICABILITY

Oligonucleotide probes, DNA chip and diagnosis kit comprising the same, and method for analyzing genotype of HPV using the same can diagnose accurately 40 types of HPV which are found in cervix and are major cause of various conditions such as cervical cancer, genital wart and the like and predict the risk thereof. The accuracy of diagnosis can be improved significantly, since diagnosis according to the present invention is carried out by analyzing L1 gene of HPV as well as E6/E7 genes of HPV to address the problems caused by analyzing the only L1 gene of HPV. Also, DNA chip and the diagnosis method of the present invention can analyze complex infection by various types of HPV, has approximately 100% of diagnosis sensitivity, diagnosis specificity and reproducibility. Finally, examination procedures and analysis of the result are very simple, and cost of examination is inexpensive.

Particularly, it is believed that the HPV genotype diagnosis DNA chip and the diagnosis kit using the same can analyze automatically presence or absence of HPV infection and genotype thereof rapidly, accurately and massively in specimens such as cervical cells, urine and the like. Also, the DNA chip can be used alone, or together with Pap cervical screening to screen cervical cancer and precancerous lesion, substituted for existing HPV examination and save examination time, labor and cost. Also, the DNA chip is useful for applying fitted type vaccines by analyzing accurate genotypes of E6/E7 on HPV infection. Accordingly, the present invention has very useful industrial availability due to contributing greatly improvements of national health and welfare by reducing incidence and mortality of cervical cancer.

While the present invention has been particularly shown and described with reference to exemplary embodiments thereof, it will be understood by those of ordinary skill in the art that various changes in form and details may be made therein without departing from the spirit and scope of the present invention as defined by the following claims.

Sequence List Text

SEQ ID Nos. 1 to 6 consist of primer base sequence for amplifying nucleic acid of HPV or beta-globulin, and SEQ ID NO. 7 to 55 consist of probe base sequence of HPV or beta-globulin. The sequence listing is attached to the present application.

The invention claimed is:

1. A DNA chip for probing and genotype analysis of HPV, comprising oligonucleotide probes of the base sequences of SEQ ID NO. 7 to SEQ ID NO. 54.

2. The DNA chip according to claim 1, wherein the DNA chip comprises a standard marker probe selected from group consisting of beta-globulin, actin and glyceraldehyde-3-phosphate dehydrogenase gene.

3. The DNA chip according to claim 2, wherein the beta-globulin probe has base sequence of SEQ ID NO. 55.

4. The DNA chip according to claim 1, wherein a 5' terminal amine group of the probe DNA is immobilized by Schiff base reaction with aldehyde group on the solid surface of the DNA chip.

5. A kit for probing and genotype analysis of HPV, comprising the DNA chip for probing and genotype analysis of HPV according to claim 1, a primer set for amplifying HPV DNA sample by PCR method, and a labeling agent for probing amplified DNA hybridized with the DNA chip.

6. The kit according to claim 5, wherein the labeling agent is selected from the group consisting of Cy-5, Cy-3, biotin binding material, 5-2'-aminoethylamino-1-naphthalene sulfate (EDANS), tetramethyirhodamine (TMR), tetramethyirhodamine isocyanate (TMRITC), x-rhodamine and TEXAS RED.

7. The kit according to claim 5, wherein the primer set comprises a primer set for amplifying HPV L1 DNA comprising base sequences of SEQ ID NO. 1 and SEQ ID NO. 2.

8. The kit according to claim 7, wherein the primer set further comprises a primer set for amplifying HPV E6/E7 DNA comprising base sequences of SEQ ID NO. 3 and SEQ ID NO. 4 and a primer set for amplifying beta-globulin DNA comprising base sequences SEQ ID NO. 5 and SEQ ID NO. 6.

9. A method for probing HPV or analyzing genotype of HPV using the DNA chip of claim 1, comprising (a) performing multiplex PCR amplifying a DNA sample by using a primer for amplifying DNA of HPV; (b) hybridizing the amplified DNA to the DNA chip; and (c) detecting the amplified DNA hybridized to the probe.

10. The method according to claim 9, wherein the multiplex PCR amplification uses a primer for amplifying HPV L1 DNA having base sequence of SEQ ID NO. 2.

11. The method according to claim 10, wherein the multiplex PCR amplification uses primer sets for amplifying HPV L1 DNA having base sequences of SEQ ID NO. 1 and SEQ ID NO. 2, SEQ ID NO. 3 and SEQ ID NO. 4, and SEQ ID NO. 5 and SEQ ID NO. 6.

12. The method according to claim 9, wherein the detection, when the gene is labeled with Cy-5, is carried out by analyzing fluorescent signal with confocal laser.

13. The method according to claim 12, wherein the Cy-5 fluorescent material is included in a reverse primer.

14. The method according to claim 12, further comprising step of washing with SSPE solution after the hybridization reaction.

15. The DNA chip according to claim 1, wherein the DNA chip has 6 to 8 compartments and each compartment is capable of integrating one sample.

* * * * *

SEQUENCE LISTING

```
<160> NUMBER OF SEQ ID NOS: 55

<210> SEQ ID NO 1
<211> LENGTH: 20
<212> TYPE: DNA
<213> ORGANISM: Artificial Sequence
<220> FEATURE:
<223> OTHER INFORMATION: primer for cloning Human papillovirus L1
      gene(forward)

<400> SEQUENCE: 1
gcmcagggwc ataayaatgg                                              20

<210> SEQ ID NO 2
<211> LENGTH: 24
<212> TYPE: DNA
<213> ORGANISM: Artificial Sequence
<220> FEATURE:
<223> OTHER INFORMATION: primer for cloning Human papillovirus L1
      gene(reverse)

<400> SEQUENCE: 2
```

-continued

```
aataaactgt aaatcatatt cctc                                    24
```

<210> SEQ ID NO 3
<211> LENGTH: 21
<212> TYPE: DNA
<213> ORGANISM: Artificial Sequence
<220> FEATURE:
<223> OTHER INFORMATION: primer for cloning Human papillovirus E6/E7
      gene(forward)

<400> SEQUENCE: 3

```
tgtcaaaaac cgtttgtgtt c                                       21
```

<210> SEQ ID NO 4
<211> LENGTH: 20
<212> TYPE: DNA
<213> ORGANISM: Artificial Sequence
<220> FEATURE:
<223> OTHER INFORMATION: primer for cloning Human papillovirus E6/E7
      gene(reverse)

<400> SEQUENCE: 4

```
gagctgtcgc ttaattgtcc                                         20
```

<210> SEQ ID NO 5
<211> LENGTH: 21
<212> TYPE: DNA
<213> ORGANISM: Artificial Sequence
<220> FEATURE:
<223> OTHER INFORMATION: primer for cloning Human beta-globulin
      gene(forward)

<400> SEQUENCE: 5

```
acacaacttg tgttcactag c                                       21
```

<210> SEQ ID NO 6
<211> LENGTH: 21
<212> TYPE: DNA
<213> ORGANISM: Artificial Sequence
<220> FEATURE:
<223> OTHER INFORMATION: primer for cloning Human beta-globulin
      gene(reverse)

<400> SEQUENCE: 6

```
caaacttcat ccacgttcac c                                       21
```

<210> SEQ ID NO 7
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 7

```
ttgttgcaga tcatcaagaa                                         20
```

<210> SEQ ID NO 8
<211> LENGTH: 18
<212> TYPE: DNA
<213> ORGANISM: Artificial Sequence
<220> FEATURE:
<223> OTHER INFORMATION: probe for searching Human papillovirus gene

<400> SEQUENCE: 8

```
cacgacagga acgactcc                                           18
```

<210> SEQ ID NO 9
<211> LENGTH: 19
<212> TYPE: DNA
<213> ORGANISM: Artificial Sequence
<220> FEATURE:
<223> OTHER INFORMATION: probe for searching Human papillovirus gene

<400> SEQUENCE: 9
caagtgtaaa catgcgtgg                                                  19

<210> SEQ ID NO 10
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 10
ctgtgacgtg taaaaacgcc                                                 20

<210> SEQ ID NO 11
<211> LENGTH: 18
<212> TYPE: DNA
<213> ORGANISM: Artificial Sequence
<220> FEATURE:
<223> OTHER INFORMATION: probe for searching Human papillovirus gene

<400> SEQUENCE: 11
gtcctgttgg aaaccaac                                                   18

<210> SEQ ID NO 12
<211> LENGTH: 17
<212> TYPE: DNA
<213> ORGANISM: Artificial Sequence
<220> FEATURE:
<223> OTHER INFORMATION: probe for searching Human papillovirus gene

<400> SEQUENCE: 12
gaccccgacc tgtgacc                                                    17

<210> SEQ ID NO 13
<211> LENGTH: 17
<212> TYPE: DNA
<213> ORGANISM: Artificial Sequence
<220> FEATURE:
<223> OTHER INFORMATION: probe for searching Human papillovirus gene

<400> SEQUENCE: 13
ccgacgtaga caaacac                                                    17

<210> SEQ ID NO 14
<211> LENGTH: 16
<212> TYPE: DNA
<213> ORGANISM: Artificial Sequence
<220> FEATURE:
<223> OTHER INFORMATION: probe for searching Human papillovirus gene

<400> SEQUENCE: 14
gaagccatgc gtggag                                                     16

<210> SEQ ID NO 15
<211> LENGTH: 22
<212> TYPE: DNA
<213> ORGANISM: Artificial Sequence
<220> FEATURE:
<223> OTHER INFORMATION: probe for searching Human papillovirus gene

```
<400> SEQUENCE: 15
tgccatatct acttcagaaa ct                                           22

<210> SEQ ID NO 16
<211> LENGTH: 22
<212> TYPE: DNA
<213> ORGANISM: Artificial Sequence
<220> FEATURE:
<223> OTHER INFORMATION: probe for searching Human papillovirus gene

<400> SEQUENCE: 16
tgtttgctgg cataatcaat ta                                           22

<210> SEQ ID NO 17
<211> LENGTH: 19
<212> TYPE: DNA
<213> ORGANISM: Artificial Sequence
<220> FEATURE:
<223> OTHER INFORMATION: probe for searching Human papillovirus gene

<400> SEQUENCE: 17
gtctgtttgt gctgcaatt                                               19

<210> SEQ ID NO 18
<211> LENGTH: 25
<212> TYPE: DNA
<213> ORGANISM: Artificial Sequence
<220> FEATURE:
<223> OTHER INFORMATION: probe for searching Human papillovirus gene

<400> SEQUENCE: 18
cagtactaat atgactttat gcaca                                        25

<210> SEQ ID NO 19
<211> LENGTH: 25
<212> TYPE: DNA
<213> ORGANISM: Artificial Sequence
<220> FEATURE:
<223> OTHER INFORMATION: probe for searching Human papillovirus gene

<400> SEQUENCE: 19
tctgctgtgt cttctagtga cagta                                        25

<210> SEQ ID NO 20
<211> LENGTH: 23
<212> TYPE: DNA
<213> ORGANISM: Artificial Sequence
<220> FEATURE:
<223> OTHER INFORMATION: probe for searching Human papillovirus gene

<400> SEQUENCE: 20
tgactttatg tgctgaggtt aaa                                          23

<210> SEQ ID NO 21
<211> LENGTH: 25
<212> TYPE: DNA
<213> ORGANISM: Artificial Sequence
<220> FEATURE:
<223> OTHER INFORMATION: probe for searching Human papillovirus gene

<400> SEQUENCE: 21
gcactgaagt aactaaggaa ggtac                                        25

<210> SEQ ID NO 22
<211> LENGTH: 23
```

```
<212> TYPE: DNA
<213> ORGANISM: Artificial Sequence
<220> FEATURE:
<223> OTHER INFORMATION: probe for searching Human papillovirus gene

<400> SEQUENCE: 22
aaaatcagag gctacataca aaa                                          23

<210> SEQ ID NO 23
<211> LENGTH: 25
<212> TYPE: DNA
<213> ORGANISM: Artificial Sequence
<220> FEATURE:
<223> OTHER INFORMATION: probe for searching Human papillovirus gene

<400> SEQUENCE: 23
ccttaccatt agtacattat ctgca                                        25

<210> SEQ ID NO 24
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 24
aaccacacaa acgttatcca                                              20

<210> SEQ ID NO 25
<211> LENGTH: 19
<212> TYPE: DNA
<213> ORGANISM: Artificial Sequence
<220> FEATURE:
<223> OTHER INFORMATION: probe for searching Human papillovirus gene

<400> SEQUENCE: 25
ccacaagtac aactgcacc                                               19

<210> SEQ ID NO 26
<211> LENGTH: 29
<212> TYPE: DNA
<213> ORGANISM: Artificial Sequence
<220> FEATURE:
<223> OTHER INFORMATION: probe for searching Human papillovirus gene

<400> SEQUENCE: 26
acctctatag agtcttccat accttctac                                    29

<210> SEQ ID NO 27
<211> LENGTH: 19
<212> TYPE: DNA
<213> ORGANISM: Artificial Sequence
<220> FEATURE:
<223> OTHER INFORMATION: probe for searching Human papillovirus gene

<400> SEQUENCE: 27
cacaaaatcc tgtgccaag                                               19

<210> SEQ ID NO 28
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 28
```
ggtttcccca acatttactc                    20

<210> SEQ ID NO 29
<211> LENGTH: 24
<212> TYPE: DNA
<213> ORGANISM: Artificial Sequence
<220> FEATURE:
<223> OTHER INFORMATION: probe for searching Human papillovirus gene

<400> SEQUENCE: 29
gcaaccacac agtctatgtc taca                    24

<210> SEQ ID NO 30
<211> LENGTH: 34
<212> TYPE: DNA
<213> ORGANISM: Artificial Sequence
<220> FEATURE:
<223> OTHER INFORMATION: probe for searching Human papillovirus gene

<400> SEQUENCE: 30
gactattagt actgctacag aacagttaag taaa                    34

<210> SEQ ID NO 31
<211> LENGTH: 24
<212> TYPE: DNA
<213> ORGANISM: Artificial Sequence
<220> FEATURE:
<223> OTHER INFORMATION: probe for searching Human papillovirus gene

<400> SEQUENCE: 31
ccactgtaac cacagaaact aatt                    24

<210> SEQ ID NO 32
<211> LENGTH: 26
<212> TYPE: DNA
<213> ORGANISM: Artificial Sequence
<220> FEATURE:
<223> OTHER INFORMATION: probe for searching Human papillovirus gene

<400> SEQUENCE: 32
aatgcagcta aaagcacatt aactaa                    26

<210> SEQ ID NO 33
<211> LENGTH: 31
<212> TYPE: DNA
<213> ORGANISM: Artificial Sequence
<220> FEATURE:
<223> OTHER INFORMATION: probe for searching Human papillovirus gene

<400> SEQUENCE: 33
ctactactac tgaatcagct gtaccaaata t                    31

<210> SEQ ID NO 34
<211> LENGTH: 17
<212> TYPE: DNA
<213> ORGANISM: Artificial Sequence
<220> FEATURE:
<223> OTHER INFORMATION: probe for searching Human papillovirus gene

<400> SEQUENCE: 34
ccgaaacggc catacct                    17

<210> SEQ ID NO 35
<211> LENGTH: 20
<212> TYPE: DNA
<213> ORGANISM: Artificial Sequence -continued

```
<220> FEATURE:
<223> OTHER INFORMATION: probe for searching Human papillovirus gene

<400> SEQUENCE: 35
catttgctgg aataatcagc                                                    20

<210> SEQ ID NO 36
<211> LENGTH: 24
<212> TYPE: DNA
<213> ORGANISM: Artificial Sequence
<220> FEATURE:
<223> OTHER INFORMATION: probe for searching Human papillovirus gene

<400> SEQUENCE: 36
tatatgctgg tttaatcaat tgtt                                               24

<210> SEQ ID NO 37
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 37
gctacatctg ctgctgcaga                                                    20

<210> SEQ ID NO 38
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 38
tttgttgggg taatcaactg                                                    20

<210> SEQ ID NO 39
<211> LENGTH: 22
<212> TYPE: DNA
<213> ORGANISM: Artificial Sequence
<220> FEATURE:
<223> OTHER INFORMATION: probe for searching Human papillovirus gene

<400> SEQUENCE: 39
acaccaacac catatgacaa ta                                                 22

<210> SEQ ID NO 40
<211> LENGTH: 21
<212> TYPE: DNA
<213> ORGANISM: Artificial Sequence
<220> FEATURE:
<223> OTHER INFORMATION: probe for searching Human papillovirus gene

<400> SEQUENCE: 40
gcagtaccaa tatgtgctgt g                                                  21

<210> SEQ ID NO 41
<211> LENGTH: 18
<212> TYPE: DNA
<213> ORGANISM: Artificial Sequence
<220> FEATURE:
<223> OTHER INFORMATION: probe for searching Human papillovirus gene

<400> SEQUENCE: 41
atttgctggg gaaaccac                                                      18
```

<210> SEQ ID NO 42
<211> LENGTH: 26
<212> TYPE: DNA
<213> ORGANISM: Artificial Sequence
<220> FEATURE:
<223> OTHER INFORMATION: probe for searching Human papillovirus gene

<400> SEQUENCE: 42
cagctgaggt gtctgataat actaat                                   26

<210> SEQ ID NO 43
<211> LENGTH: 25
<212> TYPE: DNA
<213> ORGANISM: Artificial Sequence
<220> FEATURE:
<223> OTHER INFORMATION: probe for searching Human papillovirus gene

<400> SEQUENCE: 43
gacacataca agtctactaa cttta                                    25

<210> SEQ ID NO 44
<211> LENGTH: 16
<212> TYPE: DNA
<213> ORGANISM: Artificial Sequence
<220> FEATURE:
<223> OTHER INFORMATION: probe for searching Human papillovirus gene

<400> SEQUENCE: 44
agtcccccac accaac                                              16

<210> SEQ ID NO 45
<211> LENGTH: 18
<212> TYPE: DNA
<213> ORGANISM: Artificial Sequence
<220> FEATURE:
<223> OTHER INFORMATION: probe for searching Human papillovirus gene

<400> SEQUENCE: 45
cactgcaaca tctggtga                                            18

<210> SEQ ID NO 46
<211> LENGTH: 18
<212> TYPE: DNA
<213> ORGANISM: Artificial Sequence
<220> FEATURE:
<223> OTHER INFORMATION: probe for searching Human papillovirus gene

<400> SEQUENCE: 46
tacacagtcc cctccgtc                                            18

<210> SEQ ID NO 47
<211> LENGTH: 17
<212> TYPE: DNA
<213> ORGANISM: Artificial Sequence
<220> FEATURE:
<223> OTHER INFORMATION: probe for searching Human papillovirus gene

<400> SEQUENCE: 47
tacagcatcc acgcagg                                             17

<210> SEQ ID NO 48
<211> LENGTH: 24
<212> TYPE: DNA
<213> ORGANISM: Artificial Sequence
<220> FEATURE:
<223> OTHER INFORMATION: probe for searching Human papillovirus gene -continued

<400> SEQUENCE: 48
ctacaactca gtctccatct acaa                                              24

<210> SEQ ID NO 49
<211> LENGTH: 29
<212> TYPE: DNA
<213> ORGANISM: Artificial Sequence
<220> FEATURE:
<223> OTHER INFORMATION: probe for searching Human papillovirus gene

<400> SEQUENCE: 49
tctattccta atgtatacac acctaccag                                         29

<210> SEQ ID NO 50
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 50
tgctacatcc cccctgtat                                                    20

<210> SEQ ID NO 51
<211> LENGTH: 20
<212> TYPE: DNA
<213> ORGANISM: Artificial Sequence
<220> FEATURE:
<223> OTHER INFORMATION: probe for searching Human papillovirus gene

<400> SEQUENCE: 51
actatttgta ccgcctccac                                                   20

<210> SEQ ID NO 52
<211> LENGTH: 21
<212> TYPE: DNA
<213> ORGANISM: Artificial Sequence
<220> FEATURE:
<223> OTHER INFORMATION: probe for searching Human papillovirus gene

<400> SEQUENCE: 52
cacagcgtcc tctgtatcag a                                                 21

<210> SEQ ID NO 53
<211> LENGTH: 27
<212> TYPE: DNA
<213> ORGANISM: Artificial Sequence
<220> FEATURE:
<223> OTHER INFORMATION: probe for searching Human papillovirus gene

<400> SEQUENCE: 53
aggtacacag gctagtagct ctactac                                           27

<210> SEQ ID NO 54
<211> LENGTH: 21
<212> TYPE: DNA
<213> ORGANISM: Artificial Sequence
<220> FEATURE:
<223> OTHER INFORMATION: probe for searching Human papillovirus gene

<400> SEQUENCE: 54
tgctgctaca caggctaatg a                                                 21

<210> SEQ ID NO 55

```
-continued

<211> LENGTH: 16
<212> TYPE: DNA
<213> ORGANISM: Artificial Sequence
<220> FEATURE:
<223> OTHER INFORMATION: probe for searching for Human beta-globulin
      gene

<400> SEQUENCE: 55
gaggagaagt ctgccg                                                    16
```